US011571262B2

(12) United States Patent
Wang et al.

(10) Patent No.: US 11,571,262 B2
(45) Date of Patent: Feb. 7, 2023

(54) GRAPHICAL USER INTERFACE FOR PLANNING A PROCEDURE

(71) Applicant: INTUITIVE SURGICAL OPERATIONS, INC., Sunnyvale, CA (US)

(72) Inventors: Bai Wang, Palo Alto, CA (US); Federico Barbagli, San Francisco, CA (US); Energy Cruse, II, Foster City, CA (US); Scott S. Ichikawa, Seattle, WA (US); Pechin Chien Pau Lo, Santa Clara, CA (US); Oscar G. Salazar, Sunnyvale, CA (US); Aaron B. Tinling, Chimacum, WA (US); Oliver J. Wagner, Mountain View, CA (US); Tao Zhao, Sunnyvale, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 223 days.

(21) Appl. No.: 16/496,034

(22) PCT Filed: Apr. 18, 2018

(86) PCT No.: PCT/US2018/028199
§ 371 (c)(1),
(2) Date: Sep. 20, 2019

(87) PCT Pub. No.: WO2018/195221
PCT Pub. Date: Oct. 25, 2018

(65) Prior Publication Data
US 2020/0030044 A1 Jan. 30, 2020

Related U.S. Application Data

(60) Provisional application No. 62/486,896, filed on Apr. 18, 2017, provisional application No. 62/578,189, filed on Oct. 27, 2017.

(51) Int. Cl.
*A61B 34/00* (2016.01)
*A61B 34/10* (2016.01)
(Continued)

(52) U.S. Cl.
CPC .............. *A61B 34/25* (2016.02); *A61B 34/10* (2016.02); *G06F 3/04815* (2013.01);
(Continued)

(58) Field of Classification Search
None
See application file for complete search history.

(56) References Cited

U.S. PATENT DOCUMENTS 6,203,493 B1 * 3/2001 Ben-Haim ......... A61B 1/00135
600/117
6,380,732 B1 4/2002 Gilboa
(Continued)

FOREIGN PATENT DOCUMENTS

CN 106170265 A 11/2016
WO WO-2016018648 A1 2/2016

OTHER PUBLICATIONS

K. Mori, J. Hasegawa, Y. Suenaga and J. Toriwaki, "Automated anatomical labeling of the bronchial branch and its application to the virtual bronchoscopy system," in IEEE Transactions on Medical Imaging, vol. 19, No. 2, pp. 103-114, Feb. 2000, doi: 10.1109/42.836370. (Year: 2000).*
(Continued)

*Primary Examiner* — William L Bashore
*Assistant Examiner* — Nathan K Shrewsbury
(74) *Attorney, Agent, or Firm* — Haynes and Boone, LLP

(57) ABSTRACT

A system and method of planning a procedure includes a planning workstation including: a display system; and a user input device. The planning workstation is configured to: display image data via the display system; receive a first user
(Continued)

input via the user input device; display via the display system a target of a medical procedure within the displayed image data identified based at least on the first user input; display an interactive image via the display system, the interactive image including the image data, a plurality of connected anatomical passageways, and the identified target; receive a second user input via the user input device; display via the display system a trajectory between the target and an exit point along a nearest passageway of the plurality of connected anatomical passageways identified based at least on the second user input; receive a third user input via the user input device; and adjust the interactive image based at least on the defined trajectory and the third user input.

20 Claims, 42 Drawing Sheets

(51) Int. Cl.
G06F 3/04815 (2022.01)
G06F 3/04845 (2022.01)
G06F 3/04883 (2022.01)

(52) U.S. Cl.
CPC ...... *G06F 3/04845* (2013.01); *G06F 3/04883* (2013.01); *A61B 2034/105* (2016.02); *A61B 2034/107* (2016.02)

(56) References Cited

U.S. PATENT DOCUMENTS

| | | | |
|---|---|---|---|
| 6,389,187 B1 | 5/2002 | Greenaway et al. | |
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,259,290 B2* | 2/2016 | Jenkins | A61B 5/415 |
| 9,452,276 B2 | 9/2016 | Duindam et al. | |
| 9,639,666 B2* | 5/2017 | Baker | G16H 50/50 |
| 9,763,745 B2* | 9/2017 | Karmarkar | G01R 33/286 |
| 10,373,719 B2 | 8/2019 | Soper et al. | |
| 10,610,311 B2* | 4/2020 | Herbelin | A61N 1/0534 |
| 11,412,951 B2* | 8/2022 | Piron | A61B 5/0037 |
| 2004/0249267 A1* | 12/2004 | Gilboa | A61B 1/00154 |
| | | | 600/424 |
| 2005/0107679 A1* | 5/2005 | Geiger | G06T 19/003 |
| | | | 600/407 |
| 2005/0182295 A1* | 8/2005 | Soper | A61B 5/08 |
| | | | 600/117 |
| 2006/0013523 A1 | 1/2006 | Childers et al. | |
| 2006/0058647 A1* | 3/2006 | Strommer | A61B 6/12 |
| | | | 600/434 |
| 2007/0167738 A1* | 7/2007 | Timinger | A61B 34/20 |
| | | | 606/1 |
| 2007/0249911 A1* | 10/2007 | Simon | G16H 70/20 |
| | | | 600/300 |
| 2008/0081982 A1* | 4/2008 | Simon | A61B 34/25 |
| | | | 600/407 |
| 2008/0097187 A1* | 4/2008 | Gielen | A61B 34/20 |
| | | | 600/409 |
| 2008/0118135 A1* | 5/2008 | Averbuch | G06T 7/155 |
| | | | 382/131 |
| 2008/0264430 A2 | 10/2008 | Roschak | |
| 2009/0112082 A1* | 4/2009 | Piferi | G01R 33/286 |
| | | | 600/411 |
| 2009/0171184 A1* | 7/2009 | Jenkins | G01R 33/3415 |
| | | | 606/130 |
| 2009/0177077 A1* | 7/2009 | Piferi | G01R 33/285 |
| | | | 600/414 |
| 2009/0248045 A1* | 10/2009 | Trovato | A61M 25/0105 |
| | | | 606/130 |
| 2010/0054525 A1* | 3/2010 | Gong | G06T 7/11 |
| | | | 382/100 |
| 2010/0082692 A1* | 4/2010 | Akinyemi | G06V 10/764 |
| | | | 707/E17.046 |
| 2010/0121316 A1* | 5/2010 | Weese | A61B 90/36 |
| | | | 606/1 |
| 2010/0198402 A1* | 8/2010 | Greer | B25J 3/04 |
| | | | 901/41 |
| 2010/0204567 A1* | 8/2010 | Narouze | A61B 34/10 |
| | | | 600/424 |
| 2010/0204568 A1* | 8/2010 | Narouze | A61B 8/0841 |
| | | | 607/46 |
| 2010/0275145 A1* | 10/2010 | Nijlunsing | G06T 19/00 |
| | | | 715/764 |
| 2010/0310146 A1* | 12/2010 | Higgins | G06T 7/162 |
| | | | 345/419 |
| 2011/0075920 A1* | 3/2011 | Wu | G06V 10/457 |
| | | | 382/160 |
| 2012/0143198 A1 | 6/2012 | Boyer et al. | |
| 2013/0166011 A1* | 6/2013 | Strommer | A61B 8/483 |
| | | | 623/1.11 |
| 2013/0204124 A1* | 8/2013 | Duindam | A61B 5/062 |
| | | | 604/272 |
| 2013/0317351 A1* | 11/2013 | Case | A61B 90/37 |
| | | | 600/424 |
| 2013/0338437 A1* | 12/2013 | Abuzaina | A61B 34/10 |
| | | | 600/109 |
| 2014/0282216 A1* | 9/2014 | Baker | G06T 19/003 |
| | | | 715/781 |
| 2014/0343416 A1* | 11/2014 | Panescu | A61B 34/30 |
| | | | 600/431 |
| 2015/0049081 A1* | 2/2015 | Coffey | G06T 19/006 |
| | | | 345/419 |
| 2015/0257847 A1* | 9/2015 | Higgins | A61B 6/466 |
| | | | 600/429 |
| 2016/0000414 A1* | 1/2016 | Brown | A61B 6/461 |
| | | | 600/567 |
| 2016/0070436 A1* | 3/2016 | Thomas | A61B 8/0808 |
| | | | 715/771 |
| 2016/0070878 A1* | 3/2016 | Soper | A61B 34/10 |
| | | | 703/11 |
| 2016/0092722 A1 | 3/2016 | Soenksen et al. | |
| 2016/0155232 A1* | 6/2016 | Sela | G06T 19/003 |
| | | | 382/103 |
| 2016/0166335 A1 | 6/2016 | Roger et al. | |
| 2016/0183841 A1* | 6/2016 | Duindam | A61B 5/743 |
| | | | 600/424 |
| 2016/0192991 A1* | 7/2016 | Vahala | A61N 7/00 |
| | | | 600/407 |
| 2016/0235492 A1* | 8/2016 | Morard | A61B 17/1757 |
| 2016/0371883 A1* | 12/2016 | Merkine | G06T 19/20 |
| 2017/0020628 A1* | 1/2017 | Averbuch | A61B 5/062 |
| 2017/0035517 A1* | 2/2017 | Geri | A61B 34/20 |
| 2017/0065349 A1* | 3/2017 | Ourselin | A61B 34/10 |
| 2017/0072222 A1* | 3/2017 | Siversson | A61B 6/563 |
| 2017/0084027 A1* | 3/2017 | Mintz | A61B 1/00149 |
| 2017/0189118 A1* | 7/2017 | Chopra | A61B 34/30 |
| 2017/0193160 A1* | 7/2017 | Long | A61B 34/25 |
| 2017/0258526 A1* | 9/2017 | Lang | A61B 17/1764 |
| 2017/0265952 A1* | 9/2017 | Donhowe | A61B 34/37 |
| 2017/0312032 A1* | 11/2017 | Amanatullah | G09B 23/30 |
| 2018/0041685 A1* | 2/2018 | Carbonell | G06T 7/33 |
| 2018/0055574 A1* | 3/2018 | Krimsky | A61B 34/10 |
| 2018/0098716 A1* | 4/2018 | Cohen | A61B 8/0833 |
| 2018/0132946 A1* | 5/2018 | Kao | G06T 7/0014 |
| 2018/0161113 A1* | 6/2018 | Lee | A61B 34/30 |
| 2018/0199999 A1* | 7/2018 | Syverson | A61B 90/00 |
| 2018/0318009 A1* | 11/2018 | Sohlden | A61B 90/96 |
| 2019/0192096 A1* | 6/2019 | Wu | A61B 6/504 |
| 2019/0350659 A1* | 11/2019 | Wang | A61B 8/0841 |
| 2020/0022649 A1* | 1/2020 | Rodriguez | A61B 5/4878 |
| 2020/0030044 A1* | 1/2020 | Wang | G16H 20/40 |
| 2020/0037916 A1* | 2/2020 | Partanen | G01R 33/5602 |
| 2020/0051274 A1* | 2/2020 | Siemionow | A61B 34/10 |
| 2020/0054399 A1 | 2/2020 | Duindam et al. | |
| 2020/0078103 A1 | 3/2020 | Duindam et al. | |
| 2020/0100851 A1* | 4/2020 | Marcuk | A61B 34/25 |

(56) References Cited

U.S. PATENT DOCUMENTS

2020/0129239 A1    4/2020    Bianchi et al.
2020/0297442 A1*  9/2020    Adebar .................. A61B 34/20
2021/0177299 A1*  6/2021    Prisco .................. A61B 1/0051

OTHER PUBLICATIONS

Extended European Search Report for Application No. EP18787521.6 dated Mar. 24, 2021, 12 pages.
Partial Supplementary European Search Report for Application No. 18787521.6 dated Dec. 22, 2020, 14 pages.
International Search Report and Written Opinion for Application No. PCT/US2018/028199, dated Aug. 6, 2018, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
International Preliminary Report on Patentability for Application No. PCT/US2018/028199, dated Oct. 31, 2019, 11 pages.

\* cited by examiner

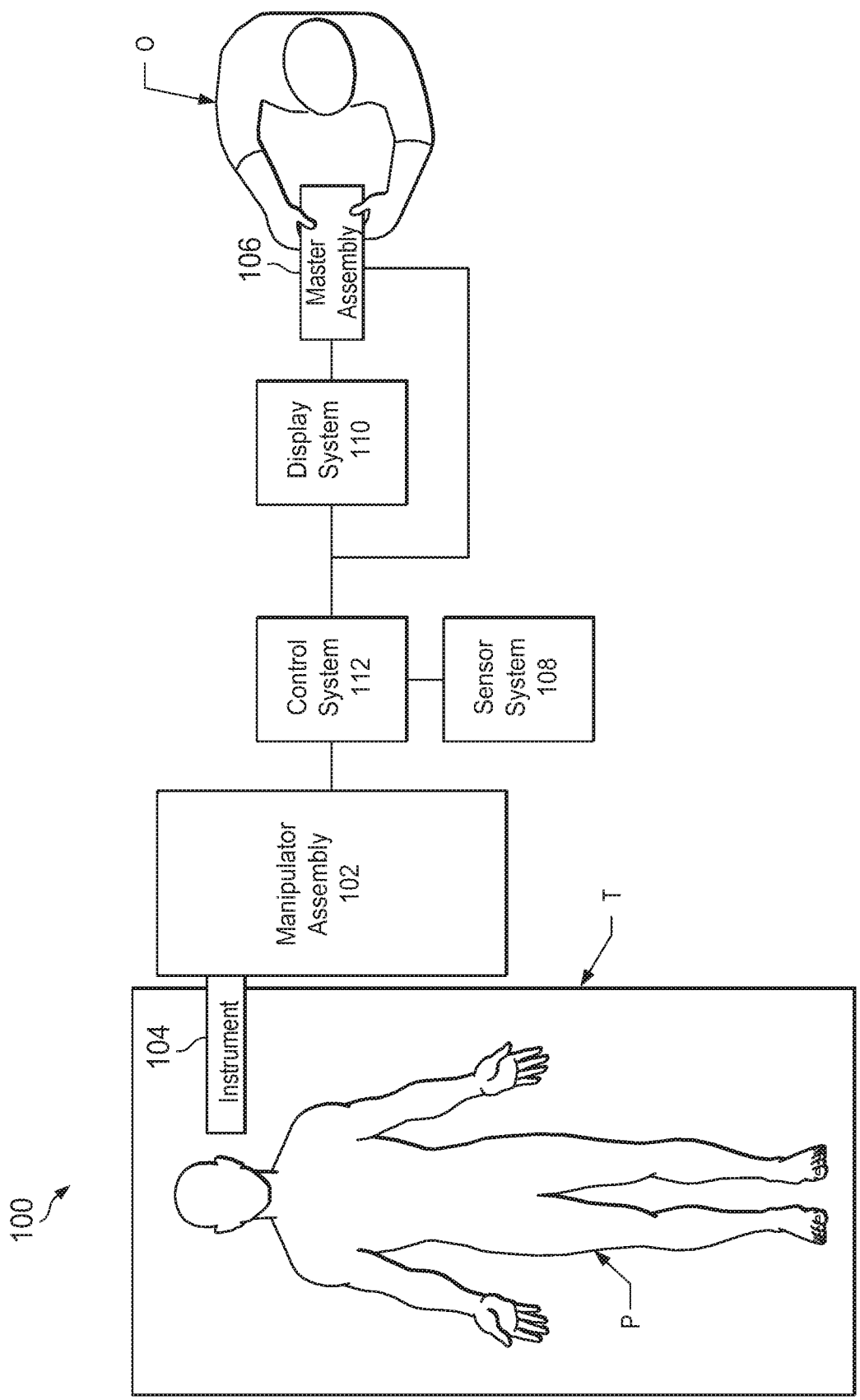

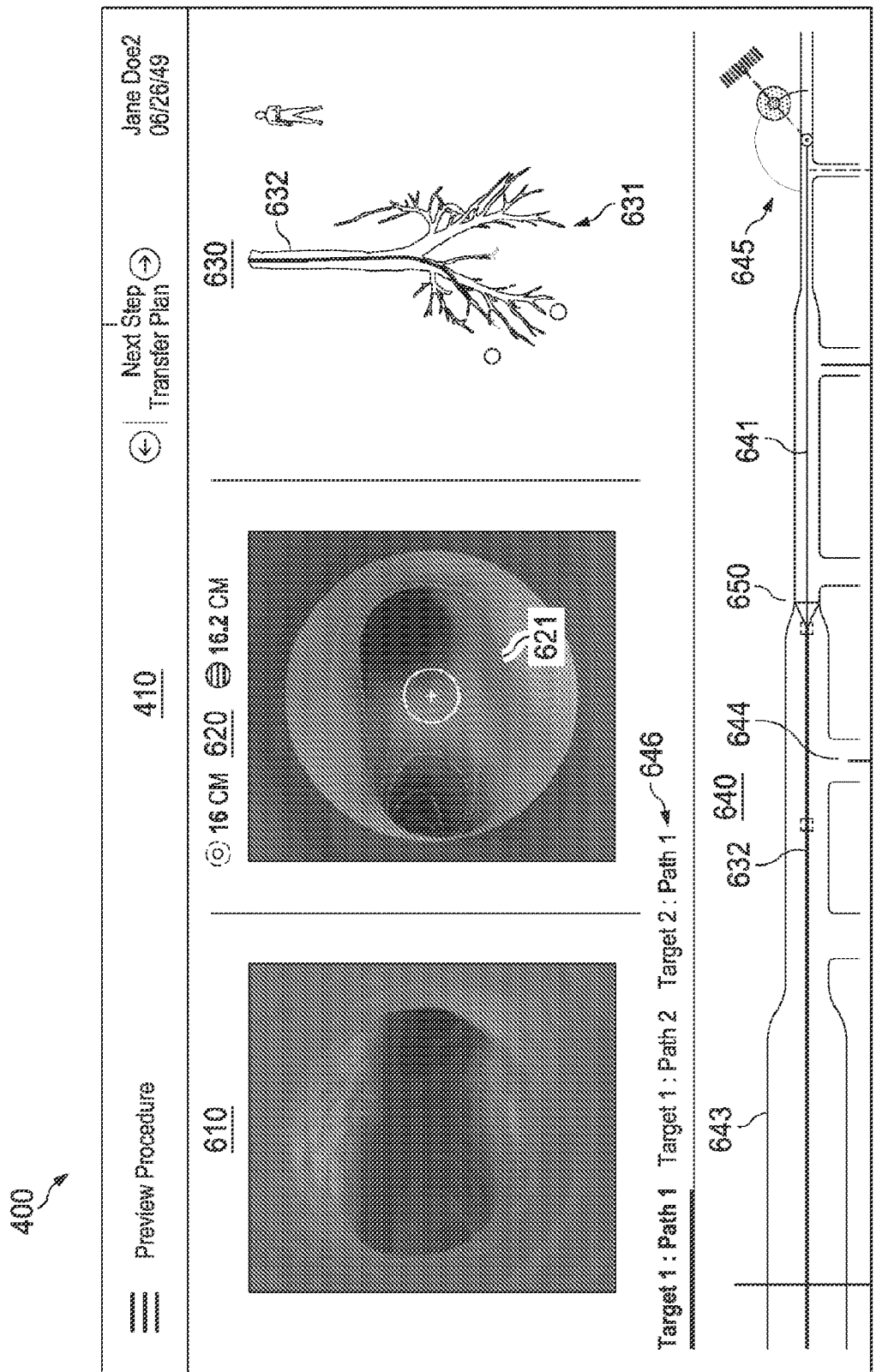

Fig. 8

GRAPHICAL USER INTERFACE FOR PLANNING A PROCEDURE

RELATED APPLICATIONS

This patent application is the U.S. national phase of International Application No. PCT/US2018/028199, filed Apr. 18, 2018, which designated the U.S. and claims priority to and benefit of the filing date of U.S. Provisional Patent Application No. 62/486,896, filed Apr. 18, 2017, entitled "Graphical User Interface for Planning a Procedure," and U.S. Provisional Patent Application No. 62/578,189, filed Oct. 27, 2017, entitled "Graphical User Interface for Labeling Anatomy," which are hereby incorporated by reference herein in their entirety.

TECHNICAL FIELD

The present disclosure is directed to systems and methods for performing an image-guided procedure and more particularly to systems and methods for analyzing, identifying, and/or labeling anatomy using a graphical user interface.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible elongate device, such as a catheter, which may be steerable, that can be inserted into anatomic passageways and navigated toward a region of interest within the patient anatomy. Control of such an elongate device by medical personnel during an image-guided procedure involves the management of several degrees of freedom including at least the management of insertion and retraction of the elongate device as well as steering or bend radius of the device. In addition, different modes of operation may also be supported.

Accordingly, it would be advantageous to provide a graphical user interface that supports intuitive planning of medical procedures including minimally invasive medical techniques.

SUMMARY

The embodiments of the invention are best summarized by the claims that follow the description.

According to some embodiments, a method for planning a medical procedure using a graphical user interface may include displaying image data via the graphical user interface and receiving a first user input defining a target of the medical procedure within the displayed image data. The method may further include displaying an interactive image via the graphical user interface, the interactive image comprising the image data, a plurality of connected anatomical passageways detected by segmentation of the image data, and the defined target. The method may further include receiving a second user input defining a trajectory between the target and an exit point along a nearest passageway of the plurality of connected anatomical passageways and receiving a third user input adjusting the interactive image based on the defined trajectory.

According to some embodiments, a method for planning a medical procedure using a graphical user interface may include displaying image data via the graphical user interface, receiving a first user input defining a hazard within the displayed image data, and displaying an interactive image. The interactive image includes the image data, a plurality of connected anatomical passageways detected by segmentation of the image data, and the defined hazard.

According to some embodiments, a method for previewing a plan for a medical procedure using a graphical user interface may include providing a plurality of interactive windows for a user to view the plan for the medical procedure. Each of the plurality of interactive windows may display a different rendering of a model of anatomical passageways. The method may further include displaying a path through the anatomical passageways to a target of the medical procedure, displaying a virtual image of an instrument within the anatomical passageways, displaying a control point corresponding to a distal end of the instrument in at least one of the plurality of interactive windows, receiving a user input defining a position of the control point, and in response to receiving the user input, dynamically updating a position of the instrument in each of the plurality of interactive windows to match the position of the control point.

According to some embodiments, a planning workstation may include a display system and a user input device. The planning workstation may be configured to display image data via the display system, receive a first user input via the user input device, the first user input defining a target of the medical procedure within the displayed image data, display an interactive image via the display system, the interactive image comprising the image data, a plurality of connected anatomical passageways detected by segmentation of the image data, and the defined target, receive a second user input via the user input device, the second user input defining a trajectory between the target and an exit point along a nearest passageway of the plurality of connected anatomical passageways, and receive a third user input via the user input device, the third user input adjusting the interactive image based on the defined trajectory.

According to some embodiments, a non-transitory machine readable medium may include a plurality of machine readable instructions which when executed by one or more processors associated with a planning workstation are adapted to cause the one or more processors to perform a method. The method may include displaying image data via the graphical user interface, receiving a first user input defining a hazard within the displayed image data, and displaying an interactive image. The interactive image may comprise the image data, a plurality of connected anatomical passageways detected by segmentation of the image data, and the defined hazard.

According to some embodiments, a non-transitory machine readable medium may include a plurality of machine readable instructions which when executed by one or more processors associated with a planning workstation are adapted to cause the one or more processors to perform a method. The method may include providing a plurality of interactive windows for a user to view the plan for the medical procedure, displaying a path through the anatomical passageways to a target of the medical procedure, displaying a virtual image of an instrument within the anatomical passageways, displaying a control point corresponding to a distal end of the instrument in at least one of the plurality of interactive windows, receiving a user input defining a position of the control point, and in response to receiving the user input, dynamically updating a position of the instrument in each of the plurality of interactive windows to match the position of the control point. Each of the plurality of interactive windows displays a different rendering of a model of anatomical passageways.

According to some embodiments, a method of planning a medical procedure may include receiving imaging data and rendering a model of anatomical passageways based on the imaging data, the anatomical passageways including a plurality of branches. An image of the model may be displayed via a graphical user interface. A first user input representing selection of a first label may be received, and a second user input representing selection of a first branch of the plurality of branches may be received. In response to the first user input and the second user input, the first branch may be labeled with the first label, and a representation of the first label applied to the first branch may be displayed via the graphical user interface.

According to some embodiments, a non-transitory machine readable medium may include a plurality of machine readable instructions. The instructions may cause the one or more processors to display, via a graphical user interface, a model of anatomical passageways including a plurality of branches; display, via the graphical user interface, a list of anatomical labels; receive a first user input that selects a first label from the list of anatomical labels; receive a second user input that selects a first branch of the plurality of branches; and/or apply the first label to the first branch.

According to some embodiments, a planning workstation may include a display system and a user input device. The planning workstation may be configured to display anatomical passageways that include a plurality of branches, display a list of labels, receive a first user input via the user input device selecting a first branch of the plurality of branches, receive a second user input via the user input device selecting a first label from the list of labels, and in response to the first user input and the second user input, display a representation of the first label applied to the first branch via the display system.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee.

FIG. 1 is a simplified diagram of a teleoperated medical system according to some embodiments.

FIG. 6 is a simplified diagram of a graphical user interface in a preview mode according to some embodiments.

FIG. 8 is a simplified diagram of a graphical user interface in a management mode according to some embodiments.

Figure 17A:
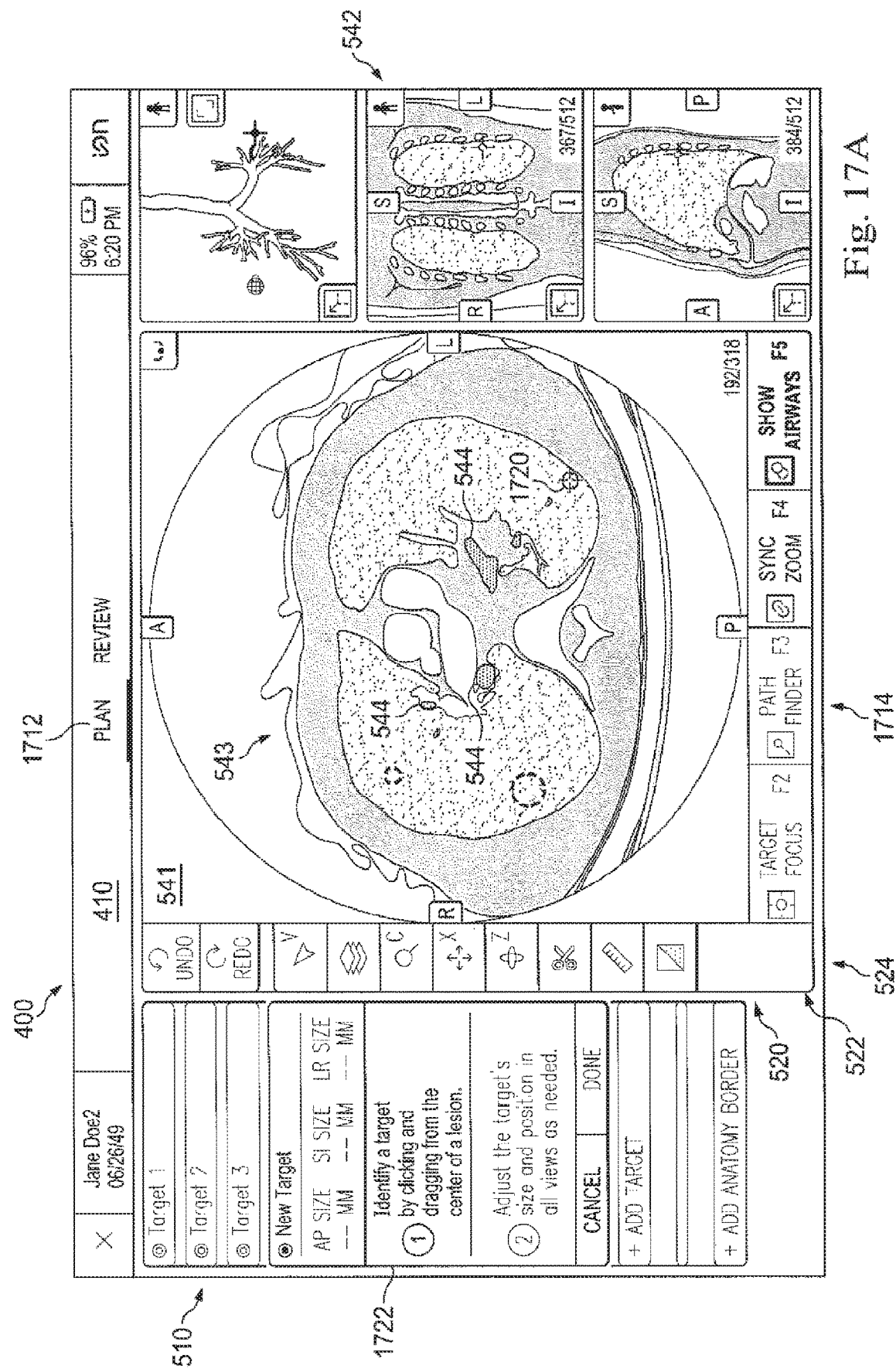
Figure 17B:
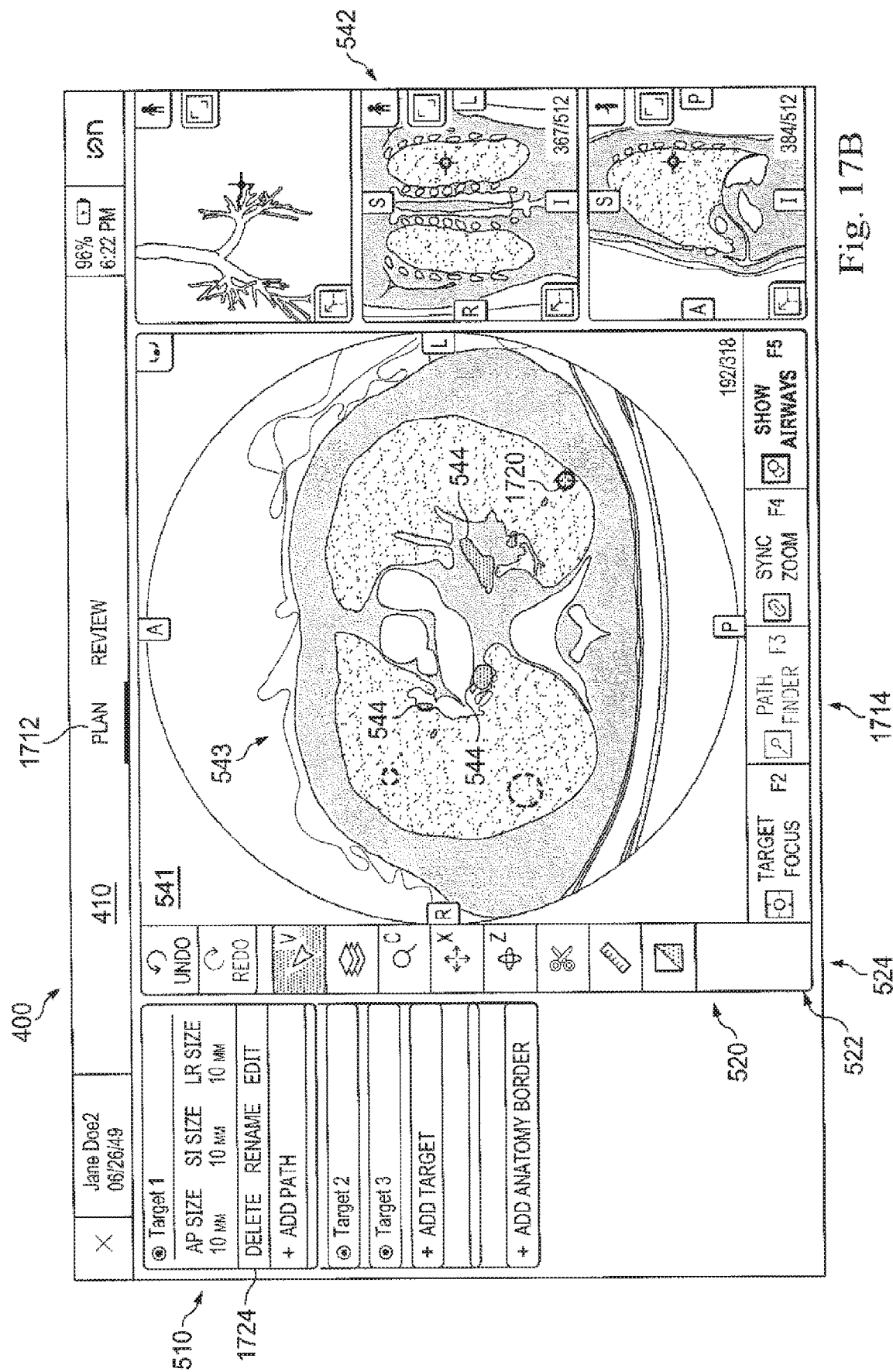
Figure 17C:
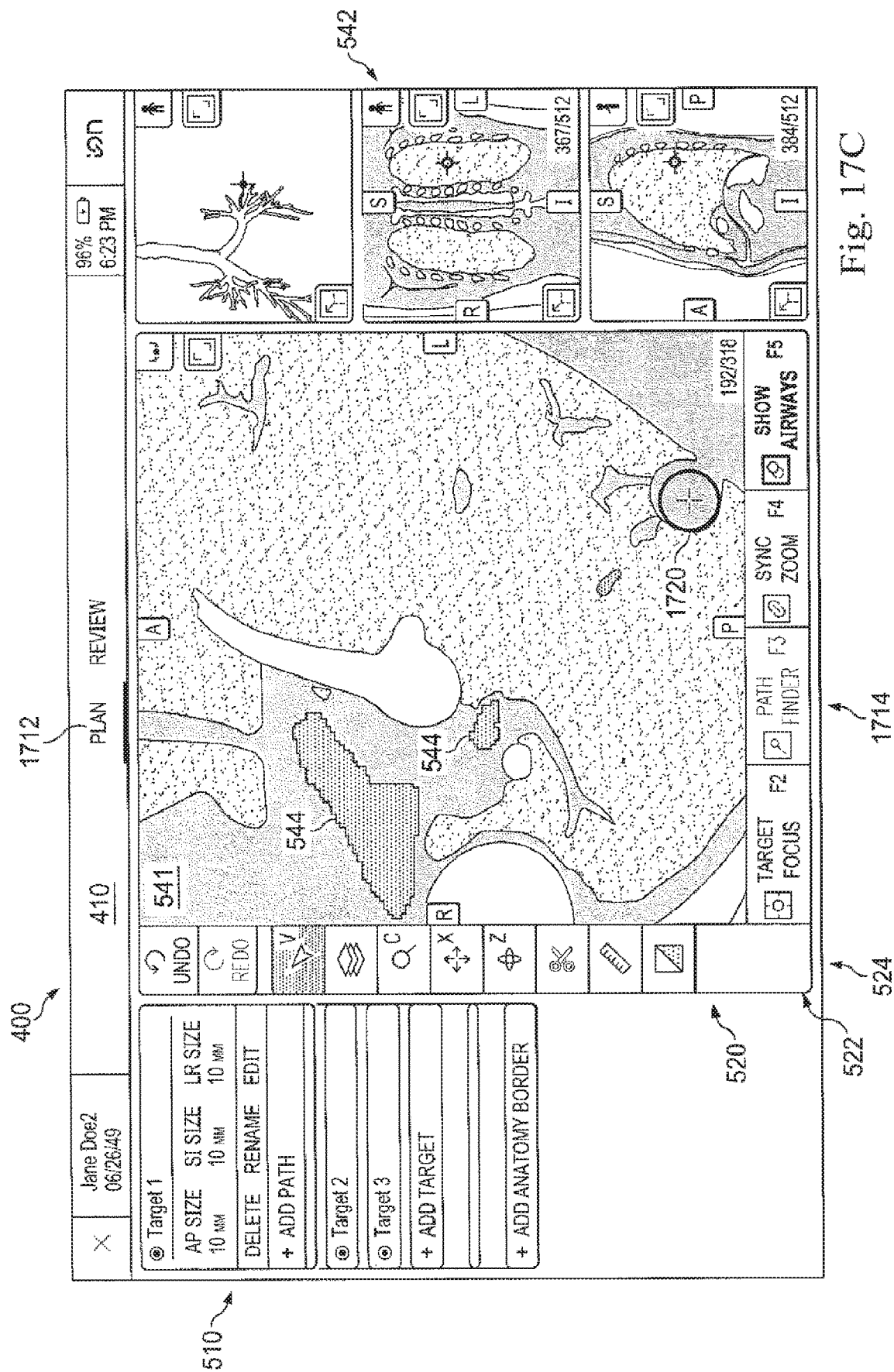
Figure 17D:
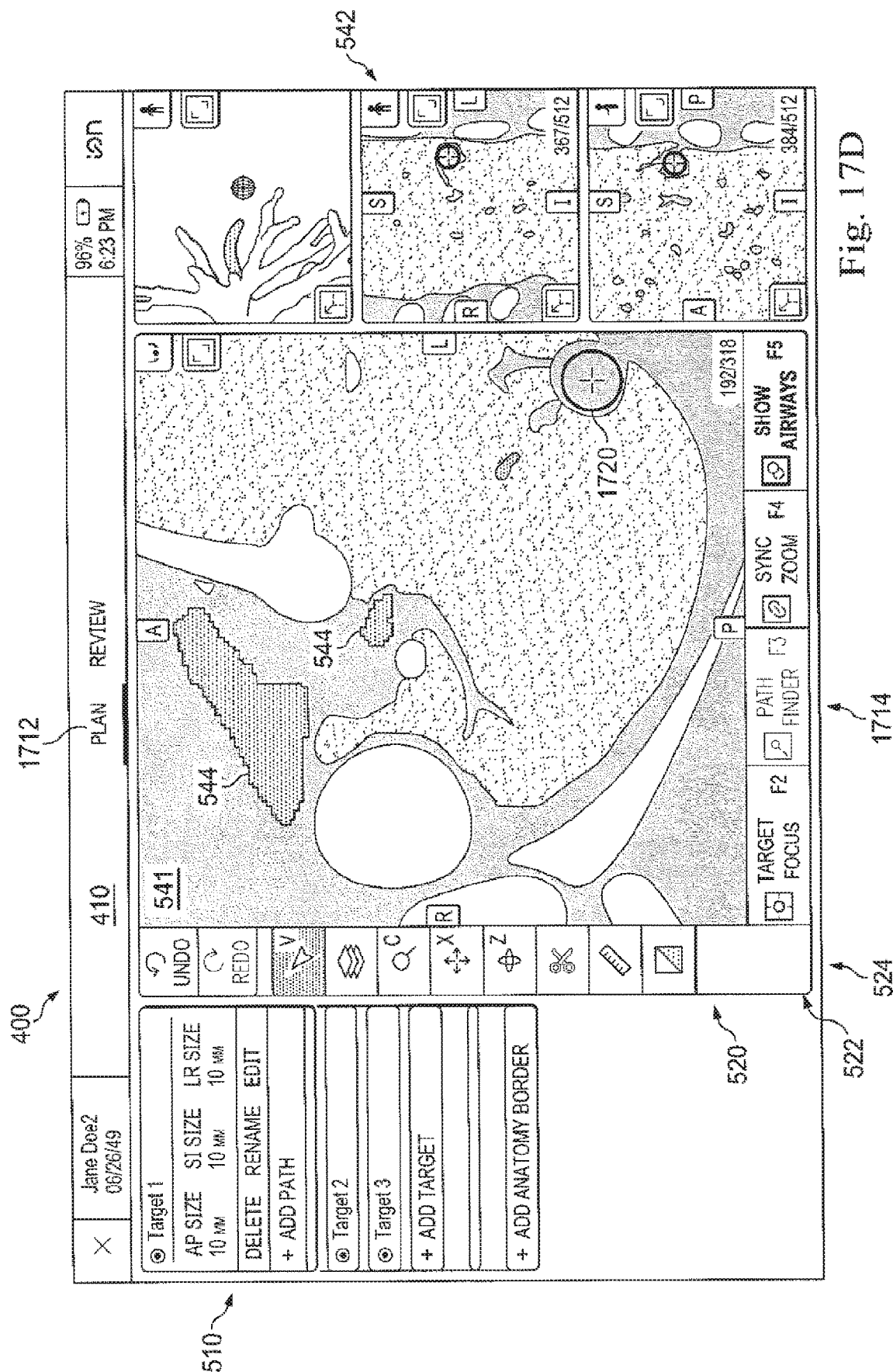
Figure 17E:
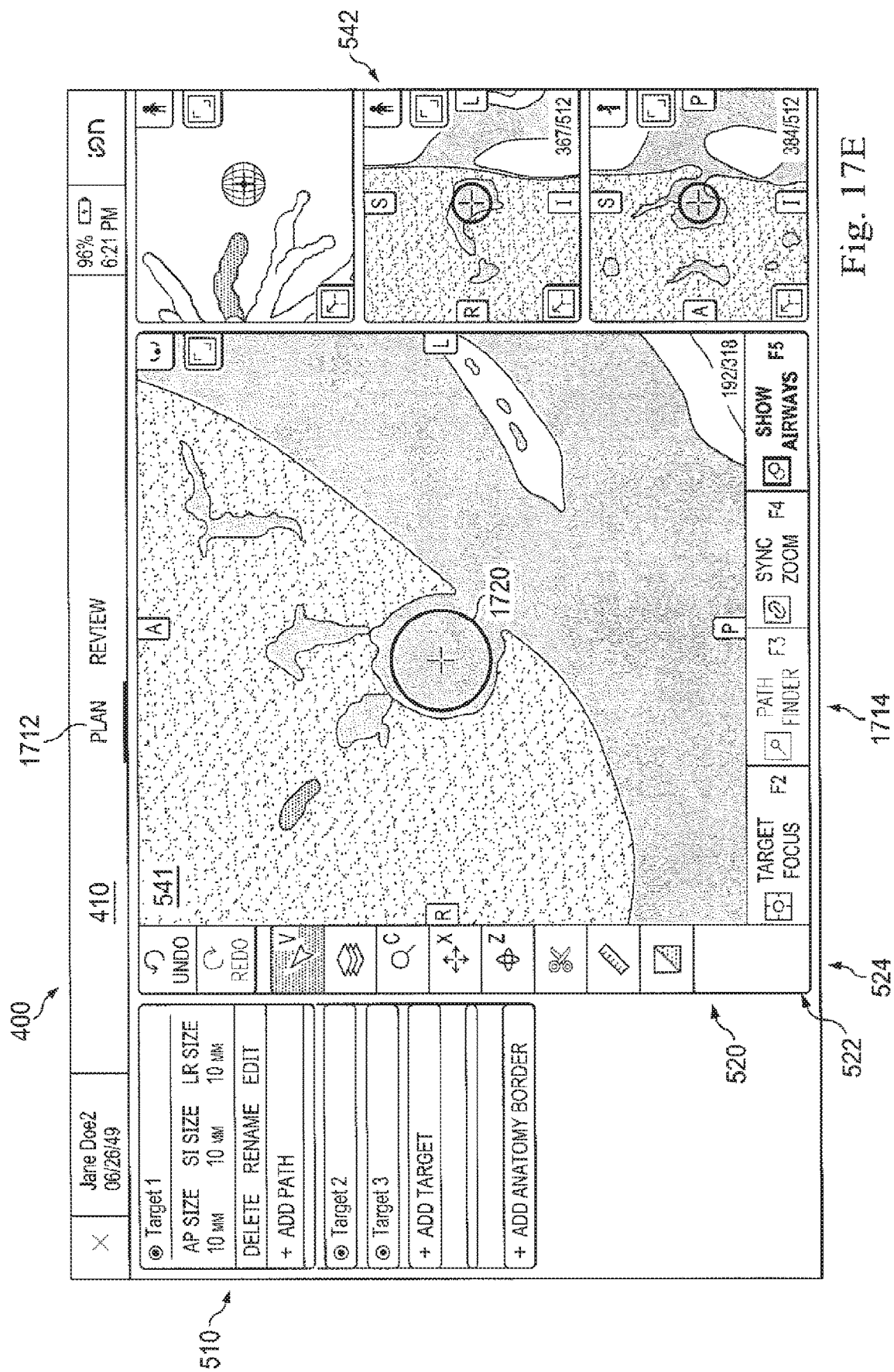
Figure 17F:
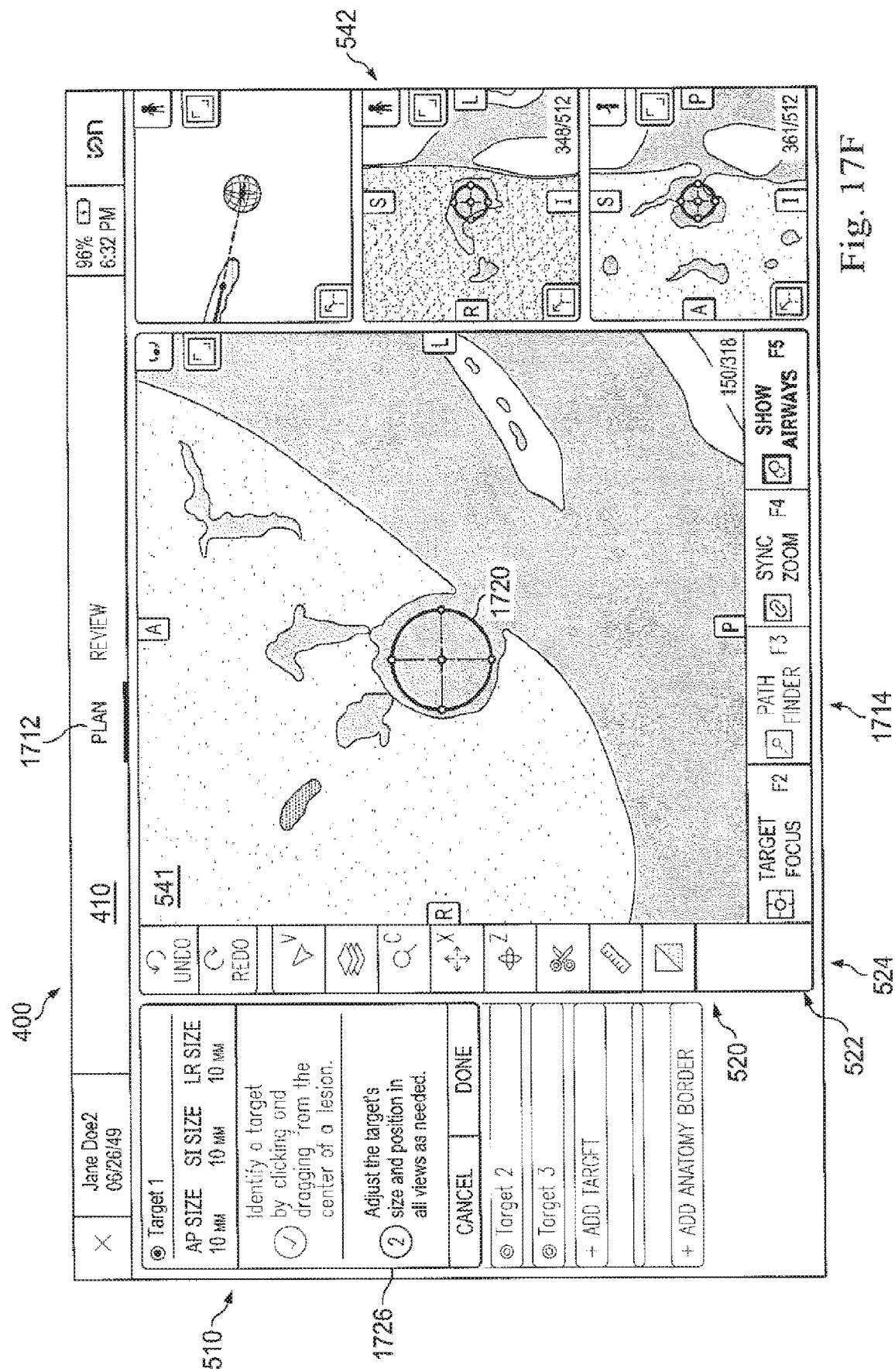
Figure 17G:
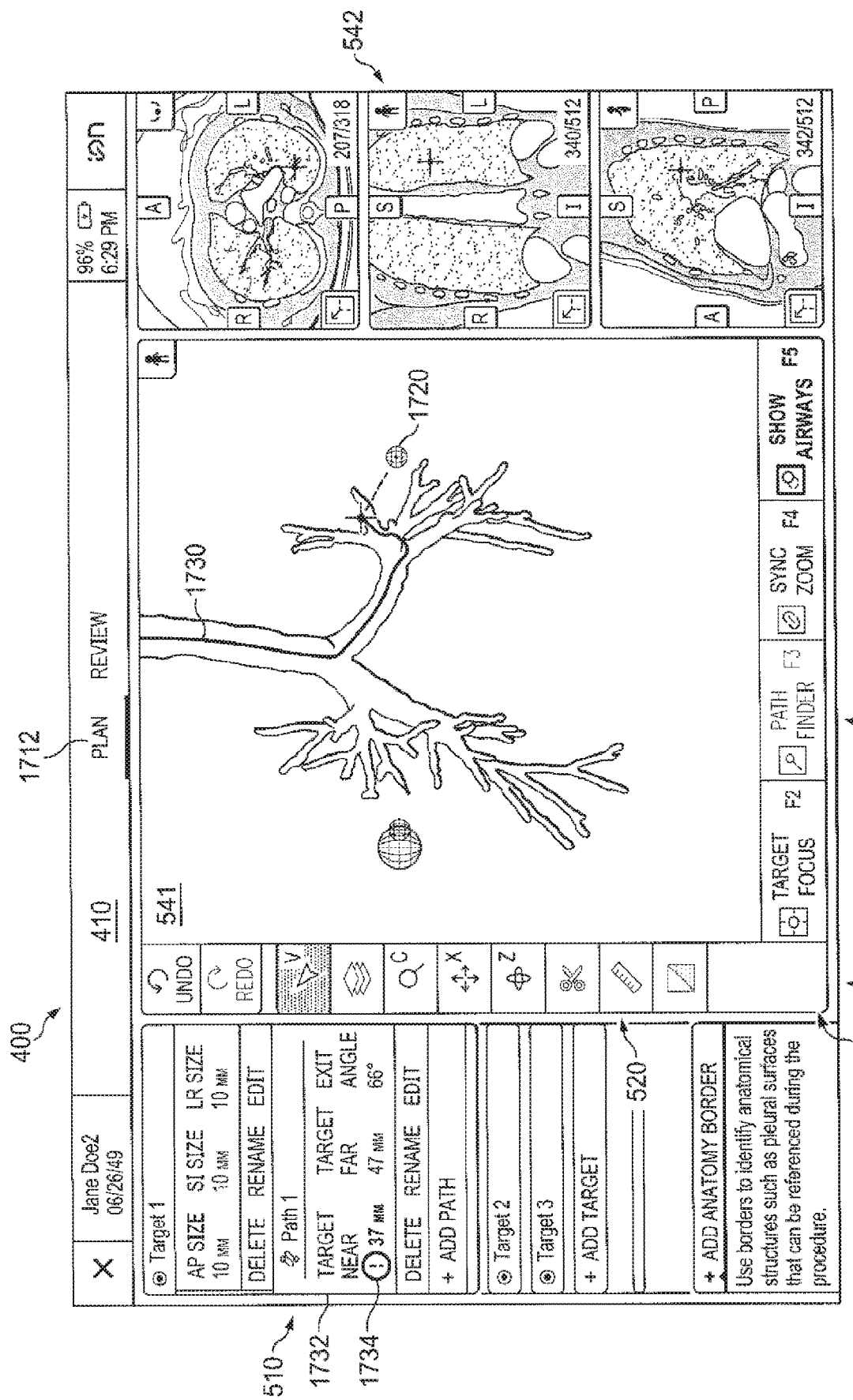
Figure 17I:
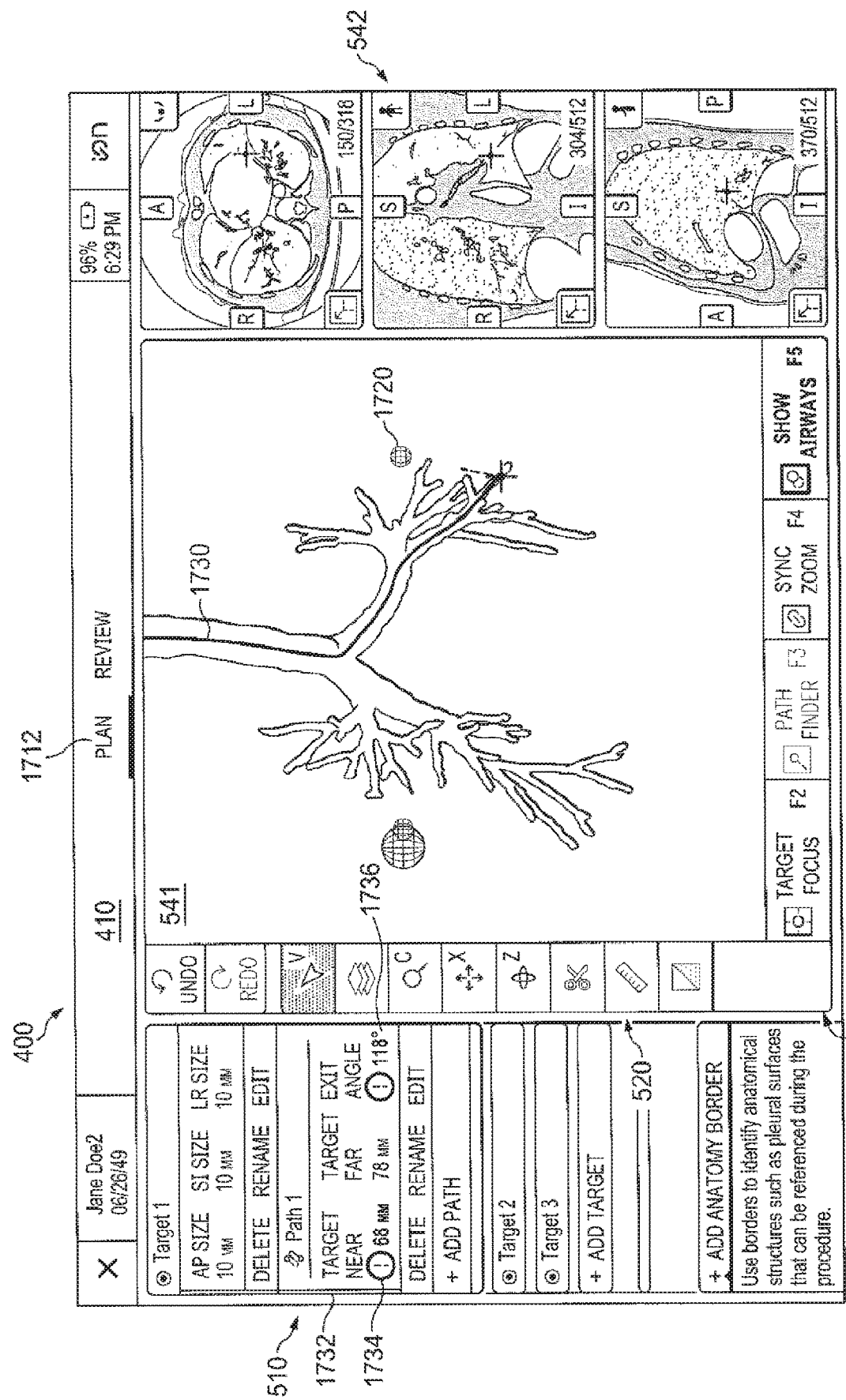
Figure 17I:
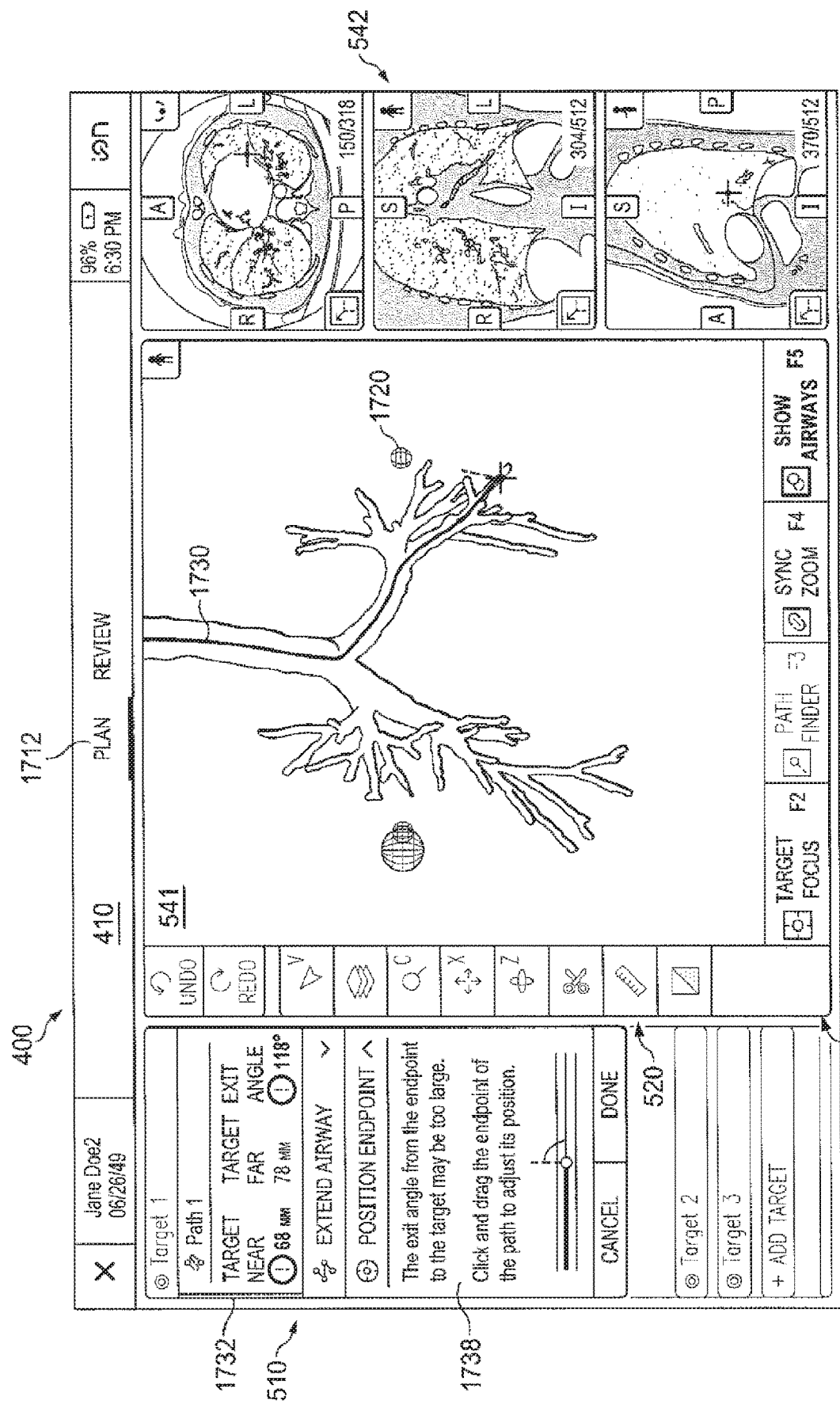
Figure 17J:
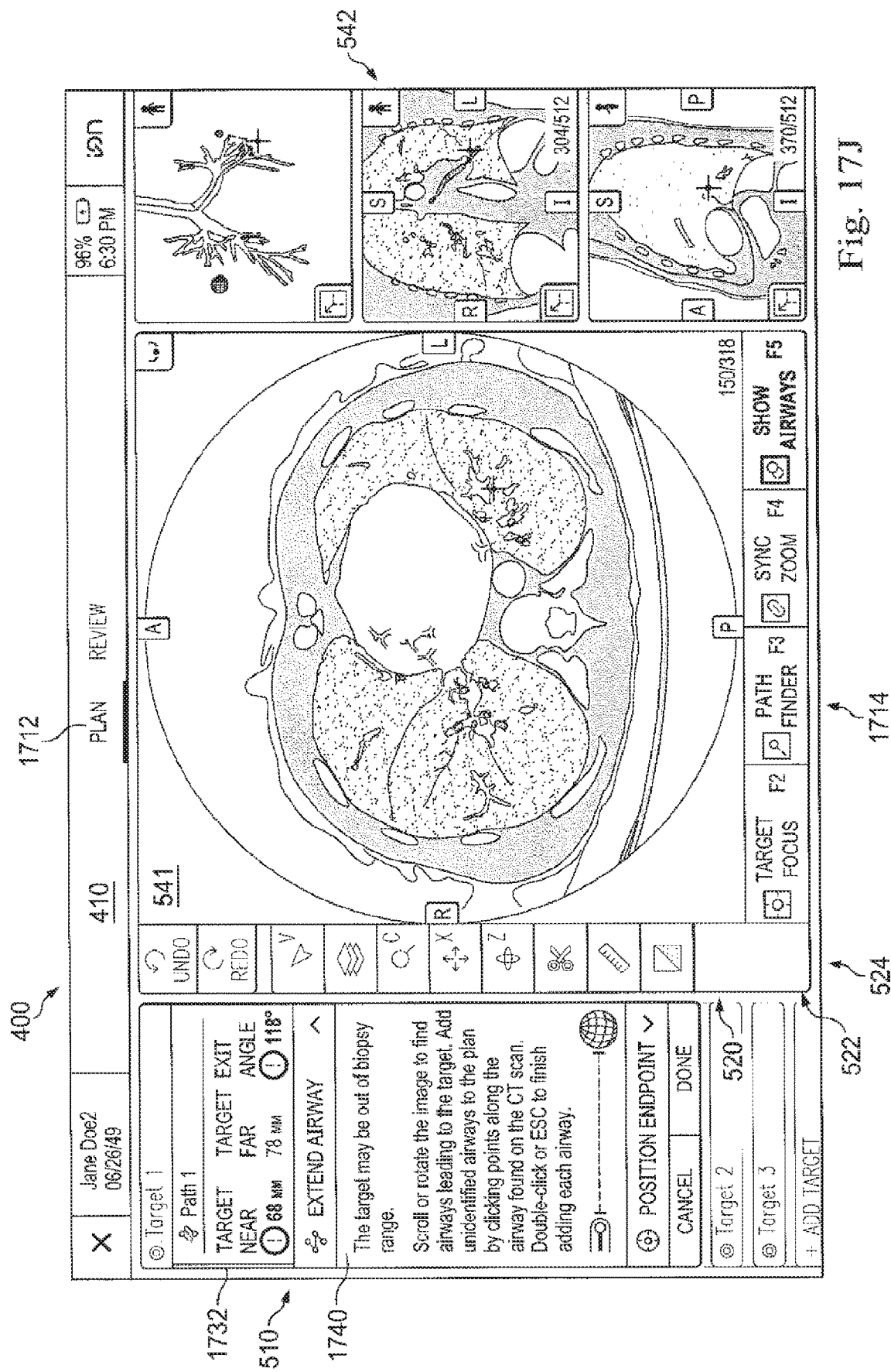
Figure 17K:
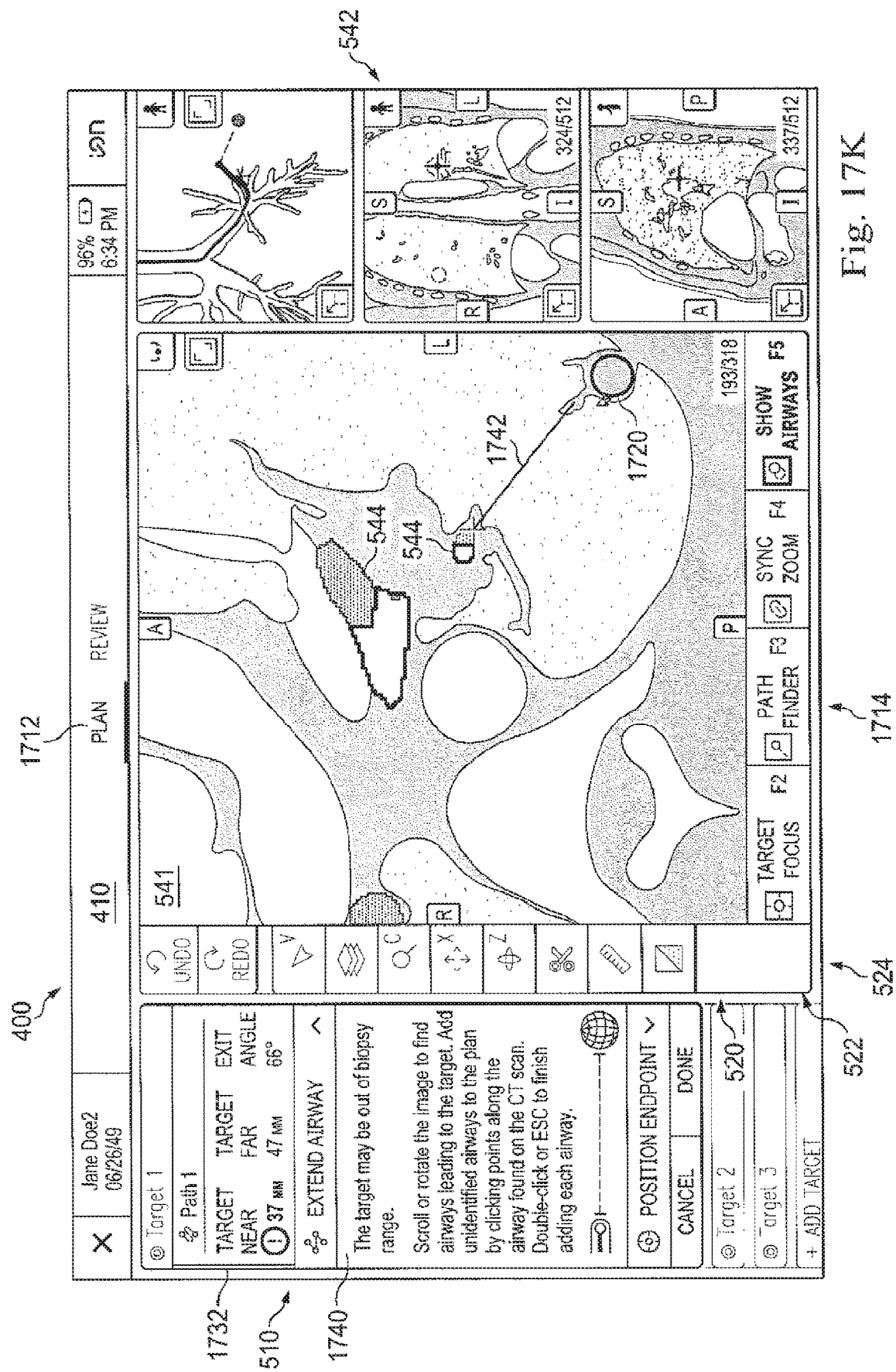
Figure 17L:
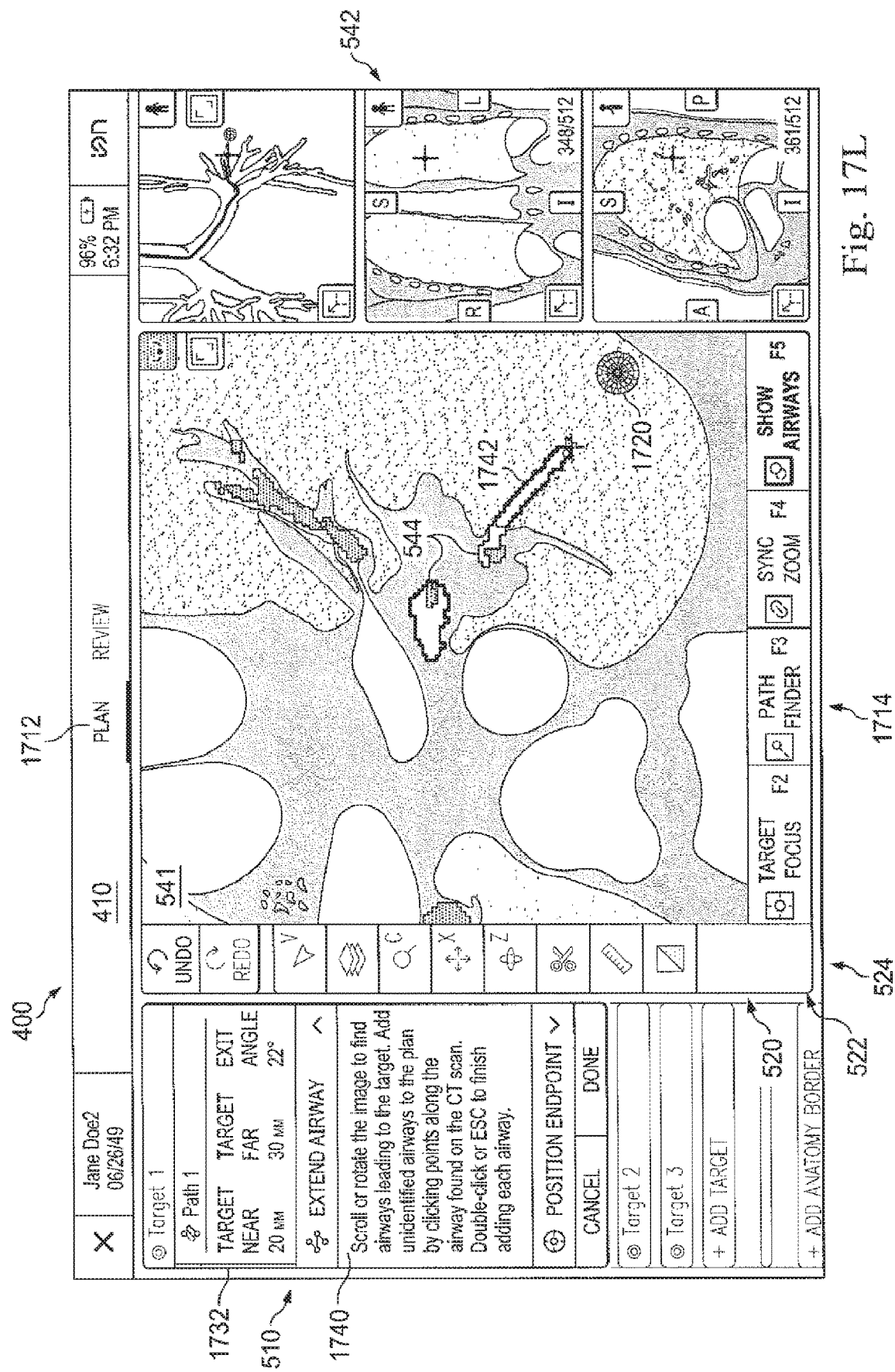
Figure 17M:
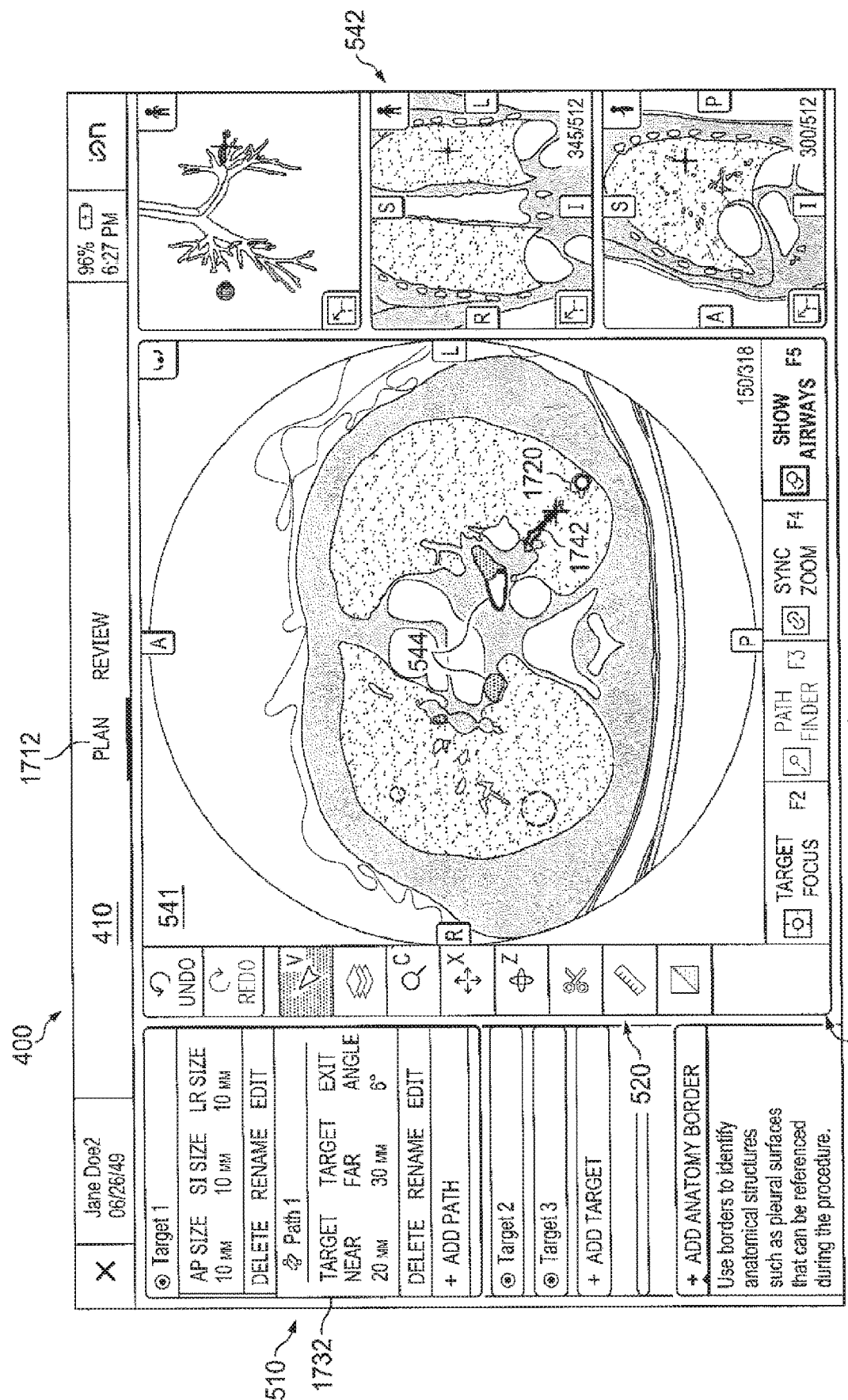
Figure 17N:
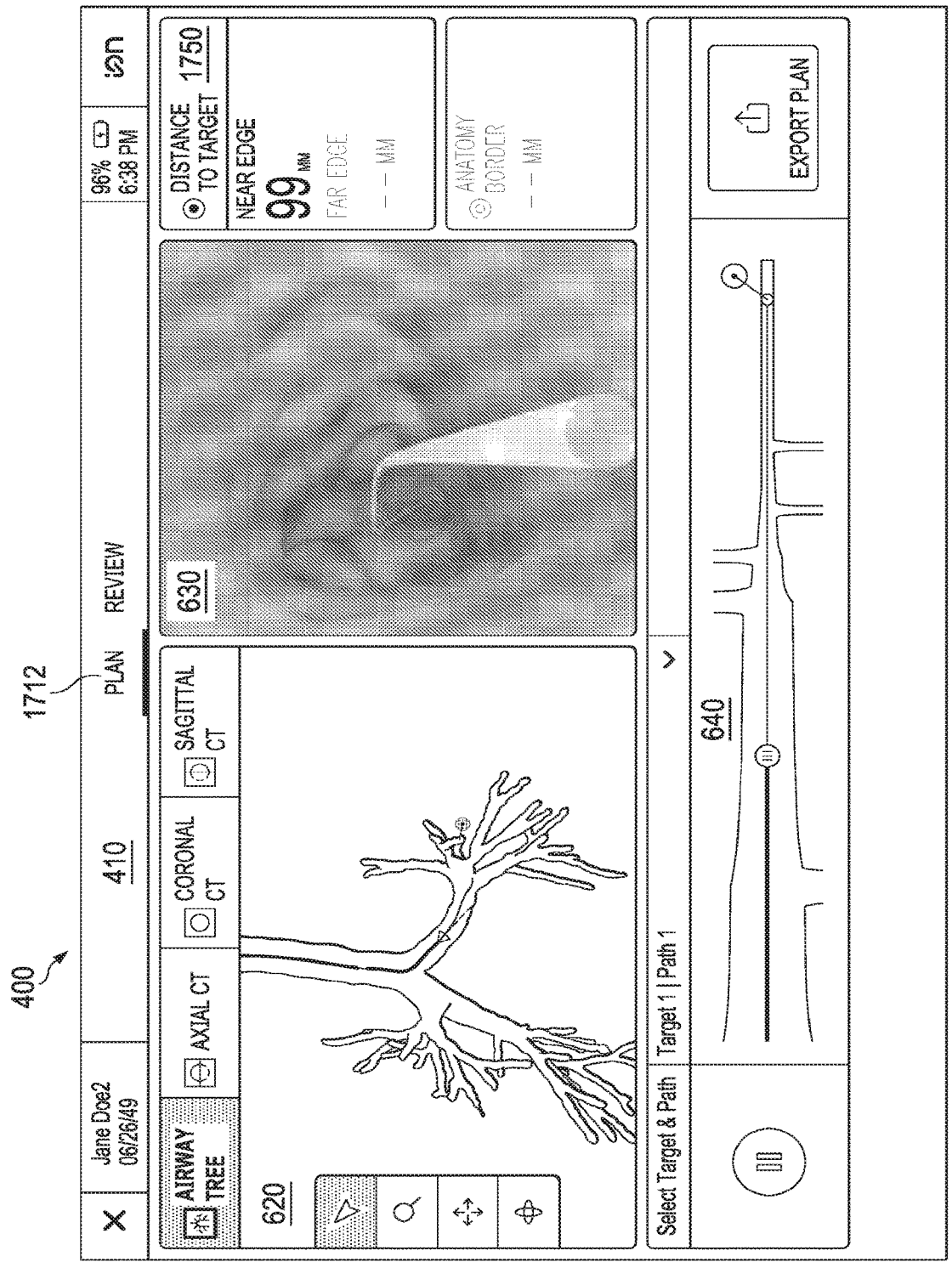

FIGS. 17A-17N are diagrams of graphical user interface corresponding to the performance of the method for planning a medical procedure according to some embodiments Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

One general aspect of the present disclosure includes a method for planning a medical procedure, the method including: displaying image data via a graphical user interface; receiving, by the graphical user interface, a first user input; identifying at least a portion of a target within the displayed image data using the first user input; displaying an interactive image via the graphical user interface, the interactive image including the image data, a plurality of connected anatomical passageways associated with the image data, and the identified target; receiving a second user input; identifying at least a portion of a trajectory between the target and an exit point along a nearest connected passageway of the plurality of connected anatomical passageways using the second user input; receiving a third user input; and adjusting the interactive image based at least on the identified trajectory and using the third user input. Implementations may include one or more of the following features. The method including providing a line tool via the graphical user interface to receive the second user input. The method where adjusting the interactive image includes: determining a distance represented by the trajectory; determining whether the distance is greater than a predetermined threshold; receiving a fourth user input; identifying at least a portion of an unconnected passageway that is closer to the target than the nearest connected passageway using the fourth user input; and connecting the unconnected passageway to the plurality of connected passageways. The method where identifying the unconnected passageway includes receiving a fifth user input and iteratively rotating the interactive image to identify the unconnected passageway in the interactive image using the fifth user input. The method where the interactive image is iteratively rotated about one or more user-defined rotation points. The method further including identifying an axis of rotation based at least on the one or more user-defined rotation points. The method where the interactive image is iteratively rotated about the axis of rotation. The method where adjusting the interactive image includes: determining an exit angle based on the trajectory; and adjusting the exit angle by altering a position of the exit point along the nearest connected passageway. The method including providing a slider via the graphical user interface and receiving user input via the slider that alters the exit point. The method further including receiving a fourth user input and identifying a hazard of the medical procedure within the displayed image data using the sixth user input. The method where the hazard corresponds to a vulnerable portion of a patient anatomy. The method where the hazard corresponds to an excessive bend in one or more of the plurality of connected anatomical passageways. The method including displaying a hazard fence to represent the hazard. The method where the hazard fence includes at least one of a circular disk, a conic hazard fence, and a hemispherical hazard fence. The method further including receiving a fourth user input and identifying at least a portion of a path within the plurality of connected passageways to the target using the seventh user input. The method where the first user input is received before completing segmentation of the image date. The method where displaying the interactive image includes overlaying the plurality of connected anatomical passageways on the displayed image data, and where the plurality of connected anatomical passageways are dynamically updated to reflect progress of the segmentation of the image data. The method further including receiving a fourth user input and identifying at least a portion of a passageway among the plurality of connected anatomical passageways to be disconnected from the plurality of connected anatomical passageways. The method where the plurality of connected anatomical passageways include lung airways.

One general aspect of the present disclosure includes a method for planning a medical procedure, the method including: providing a graphical user interface; displaying image data via the graphical user interface; receiving a first user input; identifying at least a portion of a hazard within the displayed image data using the first user input; and displaying an interactive image including the image data, a plurality of connected anatomical passageways, and the a representation of the identified hazard. Implementations may include one or more of the following features. The method where the hazard includes a vulnerable portion of a patient anatomy. The method where the hazard includes an excessive bend within the plurality of connected anatomical passageways. The method including displaying a hazard fence to represent the hazard. The method where the hazard fence includes at least one of a circular disk, a conical hazard fence, and a hemispherical hazard fence. The method where the plurality of connected anatomical passageways includes lung airways. The method further including receiving a second user input, identifying at least a portion of a target of the medical procedure within the displayed image data, and where the hazard corresponds to a vulnerable portion of a patient anatomy that is close to the target. The method where the vulnerable portion of the patient anatomy includes at least one of a lung pleura, a blood vessel, large bullae, and a heart. The method where the first user input is received before the segmentation of the image data is complete.

One general aspect of the present disclosure includes a method for previewing a plan for a medical procedure, the method including: providing a graphical user interface including a plurality of interactive windows that display the plan for the medical procedure, where at least two different renderings of a model of anatomical passageways are displayed using the plurality of interactive windows; displaying a path through the anatomical passageways to a target of the medical procedure; displaying a virtual image of an instrument within the anatomical passageways; displaying a control point corresponding to a distal end of the instrument in at least one of the plurality of interactive windows; receiving a user input; identifying a position of the control point using the user input; and in response to receiving the user input, dynamically updating a position of the instrument in at least two of the plurality of interactive windows to match the position of the control point.

One general aspect of the present disclosure includes a planning workstation including: a display system; and a user input device; where the planning workstation is configured to: display image data via the display system; receive a first user input via the user input device; display via the display system a target of a medical procedure within the displayed image data identified based at least on the first user input; display an interactive image via the display system, the interactive image including the image data, a plurality of connected anatomical passageways, and the identified target; receive a second user input via the user input device; display via the display system a trajectory between the target and an exit point along a nearest passageway of the plurality of connected anatomical passageways identified based at least on the second user input; receive a third user input via the user input device; and adjust the interactive image based at least on the defined trajectory and the third user input. Implementations may include one or more of the following features. The planning workstation where the user input device includes a touchscreen of the display system. The planning workstation where the display system adjusts the interactive image including: determine a distance represented by the trajectory; determine whether the distance is greater than a predetermined threshold; receive a fourth user input via the user input; identify an unconnected passageway that is closer to the target than the nearest connected passageway based at least on the fourth user input; and connect the unconnected passageway to the plurality of connected passageways. The planning workstation where the planning workstation is further configured to receive a fifth user input via the user input device, and rotate the interactive image to identify the unconnected passageway in the interactive image based at least on the fifth user input. The planning workstation where the interactive image is rotated about one or more user-defined rotation points. The planning workstation where the planning workstation is further configured to identify an axis of rotation based on the one or more user-defined rotation points. The planning workstation where the display system adjusts the interactive image including: determine an exit angle based on the trajectory; and adjust the exit angle by altering a position of the exit point along the nearest connected passageway. The planning workstation where the planning workstation is further configured to receive a fourth user input via the user input device, and display via the display system a hazard of the medical procedure within the displayed image data based on the fourth user input. The planning workstation where the hazard corresponds to at least one of a vulnerable portion of a patient anatomy and an excessive bend in one or more of the plurality of connected anatomical passageways. The planning workstation where the hazard is displayed using a hazard fence that includes at least one of a circular disk, a conic hazard fence, and a hemispherical hazard fence. The planning workstation where the user input device is configured to receive first user before segmentation of the image date is complete.

One general aspect of the present disclosure includes a non-transitory machine readable medium including a plurality of machine readable instructions which when executed by one or more processors associated with a planning workstation are adapted to cause the one or more processors to perform a method including: displaying image data via a graphical user interface; receiving a first user input; identifying a hazard within the displayed image data based at least on the first user input; and displaying an interactive image including the image data, a plurality of connected anatomical passageways detected by segmentation of the image data, and the identified hazard. Implementations may include one or more of the following features. The non-transitory machine readable medium where the hazard includes a vulnerable portion of a patient anatomy. The non-transitory machine readable medium where the hazard includes an excessive bend within the plurality of connected anatomical passageways. The non-transitory machine readable medium where the hazard is represented using a hazard fence. The non-transitory machine readable medium where the hazard fence includes at least one of a circular disk, a conical hazard fence, and a hemispherical hazard fence. The non-transitory machine readable medium where the plurality of connected anatomical passageways includes lung airways. The non-transitory machine readable medium where the machine readable instructions are adapted to cause the one or more processors to perform the method further including receiving a second user input, identifying a target of a medical procedure within the displayed image data using at least the second user input, and where the hazard corresponds to a vulnerable portion of a patient anatomy that is close to the target. The non-transitory machine readable medium where the vulnerable portion of the patient anatomy includes at least one of a lung pleura, a blood vessel, large bullae, and a heart. The non-transitory machine readable medium where the machine readable instructions are adapted to cause the one or more processors to perform the method including receiving the first user input segmentation of the image data is complete.

One general aspect of the present disclosure includes a non-transitory machine readable medium including a plurality of machine readable instructions which when executed by one or more processors associated with a planning workstation are adapted to cause the one or more processors to perform a method including: providing a plurality of interactive windows for a user to view the plan for a medical procedure, where each of the plurality of interactive windows displays a different rendering of a model of anatomical passageways; displaying a path through the anatomical passageways to a target of the medical procedure; displaying a virtual image of an instrument within the anatomical passageways; displaying a control point corresponding to a distal end of the instrument in at least one of the plurality of interactive windows; receiving a user input; identifying a position of the control point based at least on the user input; and in response to receiving the user input, dynamically updating a position of the instrument in at least one of the plurality of interactive windows to match the position of the control point.

One general aspect of the present disclosure includes a method of planning a medical procedure, the method including: receiving a representation of anatomical passageways including a plurality of branches; displaying, via a graphical user interface, an image of the representation; receiving a first user input representing selection of a first label; receiving a second user input representing selection of a first branch of the plurality of branches; and in response to the first user input and the second user input: labeling the first branch with the first label; and displaying, via the graphical user interface, a representation of the first label applied to the first branch. Implementations may include one or more of the following features. The method further including, based on the labeling of the first branch with the first label: selecting a second label; and displaying, via the graphical user interface, an indication that the second label has been selected. The method where the second label is selected based on an arrangement of the plurality of branches within the anatomical passageways. The method further including: receiving a third user input representing selection of a second branch of the plurality of branches; labeling the second branch with the second label; and displaying, via the graphical user interface, a representation of the second label applied to the second branch. The method further including:

identifying a group of branches from the plurality of branches that includes the first branch; and in response to the first user input and the second user input, labeling the group of branches with the first label. The method where the identifying of the group of branches includes identifying a descendent branch of the first branch and including the descendent branch in the group of branches. The method where the identifying of the group of branches includes identifying an antecedent descendent branch of the first branch and including the antecedent branch in the group of branches. The method further including, displaying via the graphical user interface, an indication of a second branch of the plurality of branches that does not have an assigned label. The method further including: receiving a third user input representing selection of a second label; labeling the second branch with the second label; and displaying, via the graphical user interface, a representation of the second label applied to the second branch. The method where the representation of the anatomical passageways is based on imaging data of a patient. The method where the imaging data includes an anatomical structure and the displaying of the image of the representation of the anatomical passageways displays the anatomical passageways and the anatomical structure. The method further including, in response to the first user input and the second user input: assigning a color to the first branch; and displaying the image of the representation of anatomical passageways with the first branch colored with the assigned color. The method further including: providing, via the graphical user interface, a cursor; detecting that the cursor is aligned with the first branch of the plurality of branches; and based on detecting that the cursor is aligned with the first branch, modifying a representation of the cursor. The method further including: receiving a third user input representing a rotation instruction; in response to the third user input, rotating the representation of anatomical passageways; and displaying, via the graphical user interface, an image of the rotated representation of anatomical passageways.

One general aspect of the present disclosure includes a non-transitory machine readable medium including a plurality of machine readable instructions, which when executed by one or more processors, cause the one or more processors to perform operations including: display, via a graphical user interface, a representation of anatomical passageways, where the anatomical passageways include a plurality of branches; display, via the graphical user interface, a list of anatomical labels; receive a first user input that selects a first label from the list of anatomical labels; receive a second user input that selects a first branch of the plurality of branches; and apply the first label to the first branch. Implementations may include one or more of the following features. The non-transitory machine readable medium where the first branch is included in a group of branches, the non-transitory machine readable medium including further instructions that cause the one or more processors to, based on the second user input that selects the first branch of the plurality of branches, apply the first label to the group of branches. The non-transitory machine readable medium including further instructions that cause the one or more processors to identify the group of branches by identifying a descendant branch of the first branch and adding the descendent branch to the group of branches. The non-transitory machine readable medium including further instructions that cause the one or more processors to perform operations including: upon applying the first label to the first branch, select a second label based on an arrangement of branches within the anatomical passageways. The non-transitory machine readable medium including further instructions that cause the one or more processors to perform operations including: receive a third user input that selects a second branch of the plurality of branches; and apply the second label to the second branch. The non-transitory machine readable medium including further instructions that cause the one or more processors to perform operations including: upon applying each label in the list of anatomical labels: identify a second branch of the plurality of branches that is unlabeled; and display, via the graphical user interface, an indication that the second branch is unlabeled. The non-transitory machine readable medium including further instructions that cause the one or more processors to perform operations including: receive a third user input that selects a second label from the list of anatomical labels; and apply the second label to the second branch. The non-transitory machine readable medium including further instructions that cause the one or more processors to perform operations including: display, via the graphical user interface, a status indicator for the second label that indicates that the second label is assigned to more than one branch. The non-transitory machine readable medium including further instructions that cause the one or more processors to perform operations including: display, via the graphical user interface, a representation of the first label being applied to the first branch. The non-transitory machine readable medium including further instructions that cause the one or more processors to, based on applying the first label to the first branch, perform operations including: assign a color to the first branch; and display, via the graphical user interface, the representation of the anatomical passageways with the first branch colored the assigned color. The non-transitory machine readable medium where the first branch is included in a group of branches, the non-transitory machine readable medium including further instructions that cause the one or more processors to, based on applying the first label to the first branch, perform operations including: assign the color to the group of branches; and display, via the graphical user interface, the representation of the anatomical passageways with the group of branches colored the assigned color. The non-transitory machine readable medium including further instructions that cause the one or more processors to: provide, via the graphical user interface, a cursor; detect that the cursor is aligned with one of the plurality of branches; and based on detecting that the cursor is aligned, modify a representation of the cursor. The non-transitory machine readable medium including further instructions that cause the one or more processors to: based on the first user input that selects the first label and the second user input that selects the first branch of the plurality of branches, compare the first label and the first branch to a second label applied to a second branch to determine whether the first label and the second label conflict; and when determined that the first label and the second label do not conflict, apply the first label to the first branch.

One general aspect of the present disclosure includes a planning workstation including: a display system; and a user input device; where the planning workstation is configured to: display anatomical passageways that include a plurality of branches via the display system; display a list of labels via the display system; receive a first user input via the user input device selecting a first branch of the plurality of branches; receive a second user input via the user input device selecting a first label from the list of labels; and in response to the first user input and the second user input, display a representation of the first label applied to the first branch via the display system. Implementations may include one or more of the following features. The planning workstation where the planning workstation is further configured to, in response to the first label being applied to the first branch, select a second label from the list of labels based on an arrangement of branches within the anatomical passageways. The planning workstation where the planning workstation is further configured to perform operations including: identify a second branch of the plurality of branches that is unlabeled; and display an indication that the second branch is unlabeled via the display system. The planning workstation where the planning workstation is further configured to, in response to the first user input selecting the first branch, perform operations including: identify a group of branches from the plurality of branches that includes the first branch; apply the first label to the group of branches; and display a representation of the first label applied to the group of branches via the display system. The planning workstation where the planning workstation is further configured to, in response to the first user input selecting the first branch, perform operations including: determine whether the first label conflicts with a second label; and when determined that the first label does not conflict with the second label, apply the first label to the first branch.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a surgeon's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by sub-systems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MM), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from representations, such as models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images or representations (e.g., models). This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered representation (e.g., a rendered model), such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
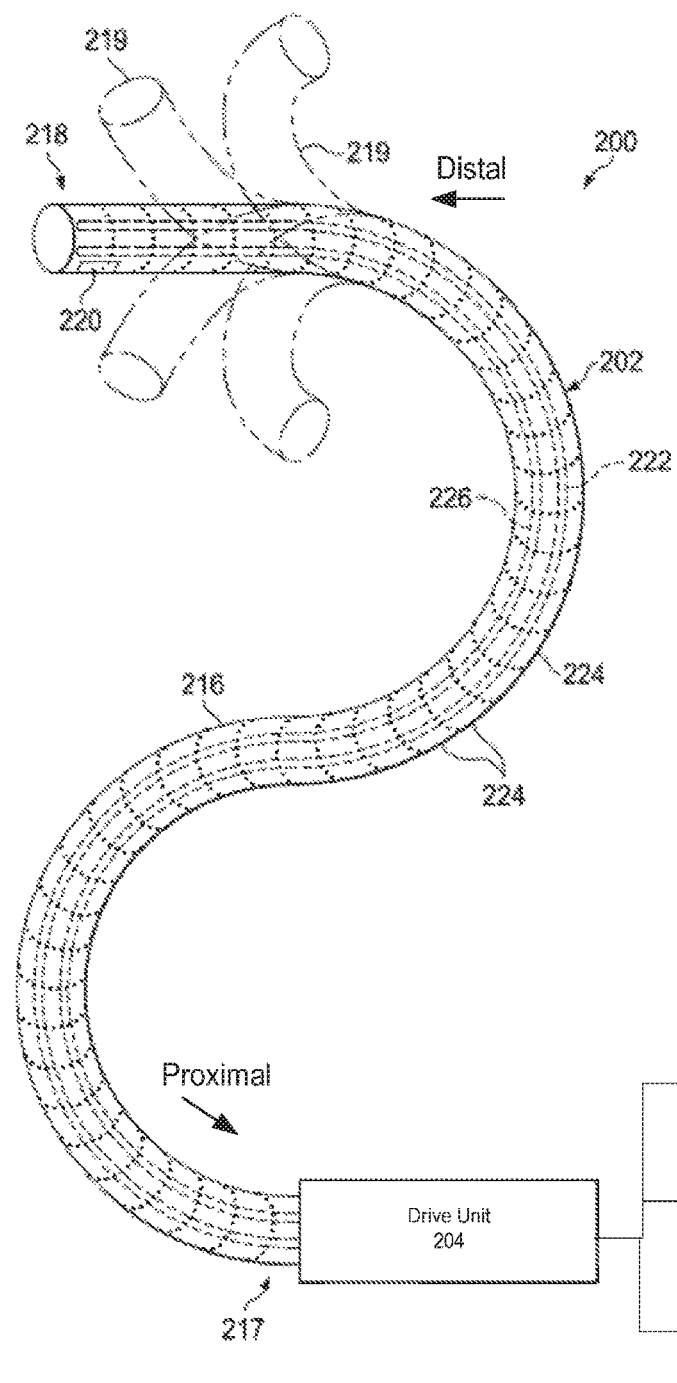
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of flexible body 216 at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 µm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 216 may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may be a component of an EM sensor system with positional sensor system 220 including one or more conductive coils that may be subjected to an externally generated electromagnetic field. Each coil of EM sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
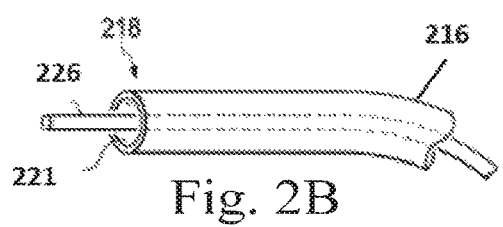
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained representations (e.g., models) to provide the physician, clinician, or surgeon or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
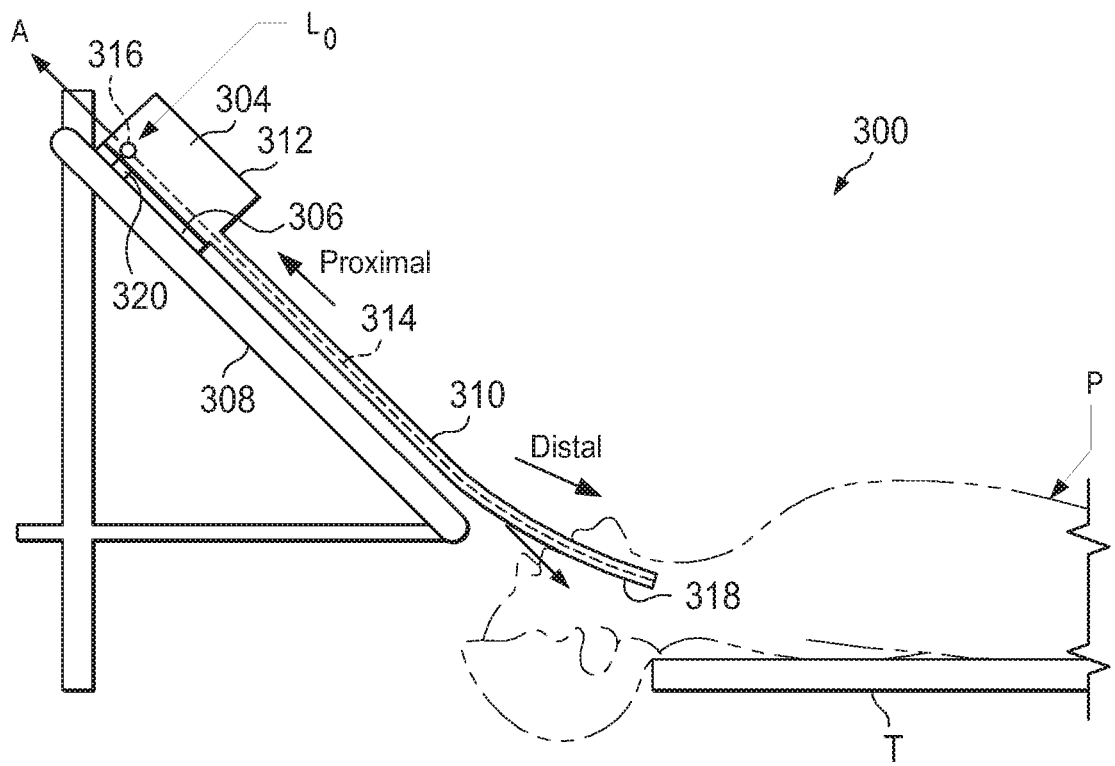
FIGS. 3A and 3B are simplified diagrams of side views of a patient coordinate space including a medical instrument mounted on an insertion assembly according to some embodiments.
Figure 3B:
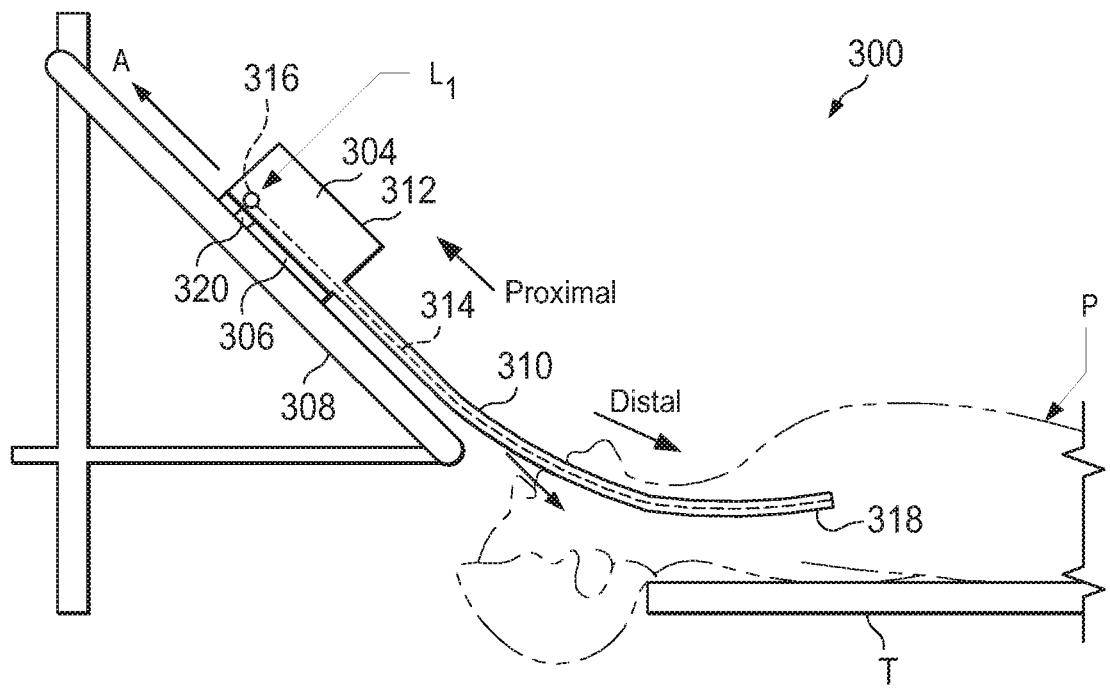

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position LX may further be used as an indicator of the distance or insertion depth to which distal end 318 of elongate device 310 is inserted into the passageways of the anatomy of patient P.

In an illustrative application, a medical instrument system, such as medical instrument system 200, may include a robotic catheter system for use in lung biopsy procedures. A catheter of the robotic catheter system provides a conduit for tools such as endoscopes, endobronchial ultrasound (EBUS) probes, and/or biopsy tools to be delivered to locations within the airways where one or more targets of the lung biopsy, such as lesions, nodules, tumors, and/or the like, are present. When the catheter is driven through anatomy, typically an endoscope is installed such that a clinician, such as surgeon O, can monitor a live camera feed of a distal end of the catheter. The live camera feed and/or other real-time navigation information may be displayed to the clinician via a graphical user interface. An example of a graphical user interface for monitoring the biopsy procedure is covered in U.S. Provisional Patent Application No. 62/486,879, entitled "Graphical User Interface for Monitoring an Image-Guided Procedure and filed Apr. 18, 2017, which is incorporated by reference above.

Before the biopsy procedure is performed using the robotic catheter system, pre-operative planning steps may be performed to plan the biopsy procedure. Pre-operative planning steps may include segmentation of image data, such as a patient CT scan, to create a 3D model of anatomy, selecting targets within the 3D model, determining airways in the model, growing the airways to form a connected tree of airways, and planning trajectories between the targets and the connected tree. One or more of these steps may be performed on the same robotic catheter system used to perform the biopsy. Alternately or additionally, planning may be performed on a different system, such as a workstation dedicated to pre-operative planning. The plan for the biopsy procedure may be saved (e.g., as one or more digital files) and transferred to the robotic catheter system used to perform the biopsy procedure. The saved plan may include the 3D model, identification of airways, target locations, trajectories to target locations, routes through the 3D model, and/or the like.

Illustrative embodiments of a graphical user interface for planning a medical procedure, including but not limited to the lung biopsy procedure described above, are provided below. The graphical user interface may include a plurality of modes including a data selection mode, a hybrid segmentation and planning mode, a preview mode, a save mode, a management mode, and a review mode. Some aspects of the graphical user interface are similar to features described in U.S. Provisional Patent Application No. 62/357,217, entitled "Graphical User Interface for Displaying Guidance Information During and Image-Guided Procedure" and filed Jun. 30, 2016, and U.S. Provisional Patent Application No. 62/357,258, entitled "Graphical User Interface for Displaying Guidance Information in a Plurality of Modes During and Image-Guided Procedure" and filed Jun. 30, 2016, which are hereby incorporated by reference in their entirety.

FIGS. 4-9 are simplified diagrams of a graphical user interface 400 displayable on a display system, such as display system 110 and/or a display system of an independent planning workstation, according to some embodiments. Graphical user interface 400 displays information associated with planning a medical procedure in one or more views that are viewable to a user, such as surgeon O. Although illustrative arrangements of views is depicted in FIG. 4-9, it is to be understood that graphical user interface 400 may display any suitable number of views, in any suitable arrangement, and/or on any suitable number of screens. In some examples, the number of concurrently displayed views may be varied by opening and closing views, minimizing and maximizing views, moving views between a foreground and background of graphical user interface 400, switching between screens, and/or otherwise fully or partially obscuring views. Similarly, the arrangement of the views—including their size, shape, orientation, ordering (in a case of overlapping views), and/or the like—may vary and/or may be user-configurable.

In some examples, graphical user interface 400 may include one or more headers, footers, sidebars, menus, message bars, pop-up windows, and/or the like. As depicted in FIGS. 4-9, graphical user interface 400 includes a dynamic header 410 that is updated based on the mode of graphical user interface 400. In various examples, header 400 may include a drop-down control menu, a page title, navigation controls (e.g., a proceed button and/or a back button), patient information, a search bar, and/or the like.

Figure 4:
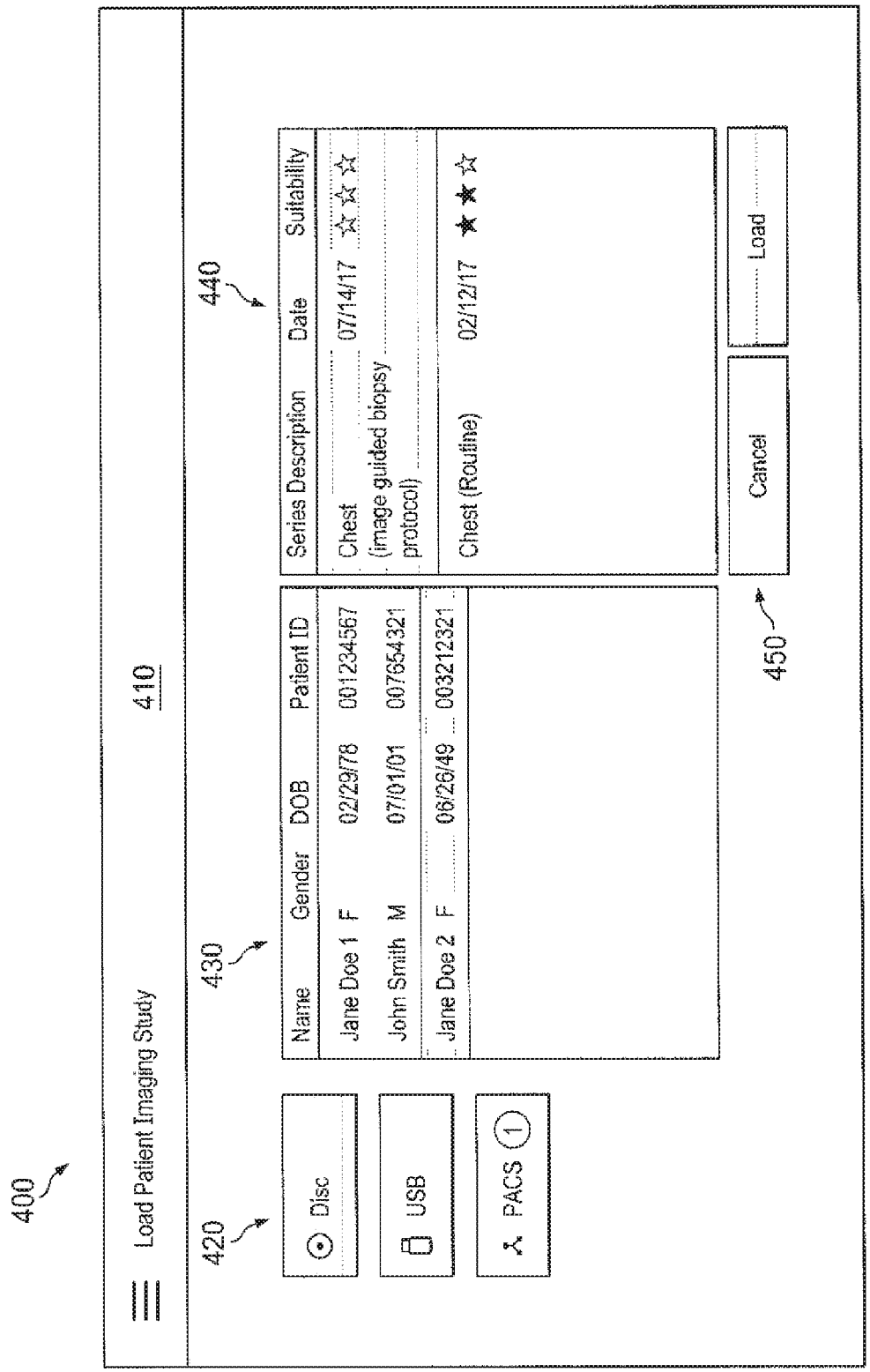
FIG. 4 is a simplified diagram of a graphical user interface in a data selection mode according to some embodiments.

FIG. 4 illustrates graphical user interface 400 in a data selection mode according to some embodiments. The data selection mode is used to select a data source, a patient, and/or image data to use when planning the medical procedure. Accordingly, graphical user interface 400 in the source selection mode may include a data source selector 420, a patient selector 430, and a data selector 440. As depicted in FIG. 4, data source selector 420 includes options to load data from a USB device, a DVD, and/or a network. It is to be understood that data may be loaded from a variety of other sources, including external and/or local sources (e.g., a local hard drive). Patient selector 430 includes a list of patients whose image data is available from the selected data source. Various patient attributes may be displayed in the list, include the patient name, gender, date of birth, unique patient ID, and/or the like. Data selector 440 includes a list of image data available for the selected patient from the selected data source. Various attributes of the data may be displayed in the list, including the data description, the date the data was acquired, and/or a suitability rating indicating the suitability of the image data for planning the medical procedure. The suitability rating may be qualitative and/or quantitative and may be assigned manually and/or automatically. The rating may be presented as a numeric score, a star rating, a percentile, a symbolic representation, and/or the like. In some examples, the suitability rating may be determined based on the quality of imaging technology used to acquire the image data. Once the image data is selected, the user may proceed to plan the medical procedure using the selected image data. For example, the user may click and/or tap a load button of a navigation panel 450 to proceed.

FIGS. 5A-5G illustrate graphical user interface 400 in a hybrid segmentation and planning mode according to some embodiments. Segmentation is a process that analyzes image data, such as the image data selected in the data selection mode, and creates a 3D model from the data. Examples of automated techniques for performing segmentation of CT data are described in U.S. patent application Ser. No. 14/845,031, entitled "Systems and Methods for Pre-Operative Modeling," which is hereby incorporated by reference in its entirety. The segmentation process generally occurs over a period of time, e.g., one to three minutes, which may vary depending on a number of factors including the quality of the CT image data, the size and/or complexity of the CT image data, the level of detail in the 3D model, the available computing resources, and/or the like. In some examples, the hybrid segmentation and planning mode of graphical user interface 400 may allow the user to plan a medical procedure based on the image data and/or the 3D model while the segmentation process is occurring and before the 3D model is complete. Accordingly, the process of planning the medical procedure may be accelerated because the user is able to begin planning the medical procedure without waiting for the potentially lengthy segmentation process to finish.

In some embodiments, graphical user interface 400 in the hybrid segmentation and planning mode may be split into one or more frames. As illustrated in FIGS. 5A-5G, graphical user interface 400 includes a control frame 510 and a canvas frame 520. Control frame 510 provides a set of controls and/or indicators for planning the medical procedure. In some examples, control frame 510 may provide controls for adding, viewing, modifying, and/or deleting one or more features of the model and/or the plan, such as targets, paths, airways, trajectories, and/or hazards. In some examples, control frame 510 may provide controls to undo and/or redo recent changes to the plan. In some examples, control frame 510 may provide a segmentation progress indicator 515 based on how far along the segmentation process is. Segmentation progress indicator 515 may be formatted as a progress bar, an elapsed time indicator, an estimated remaining time indicator, and/or any other suitable indicator of segmentation progress. In some embodiments, segmentation progress indicator 515 may disappear when segmentation is complete.

In some embodiments, graphical user interface 400 in the hybrid segmentation and planning mode may include a canvas frame 520. As illustrated in FIGS. 5A-5G, canvas frame 520 provides a workspace 522 for selecting, viewing, and/or interacting with image data and/or model data. Illustrative functions that may be performed via workspace 522 include adding, modifying, and/or deleting features (e.g., targets, paths, and/or hazards) of the plan, manipulating the 3D model, and/or verifying the accuracy of the segmentation process. To accommodate these functions, workspace 522 may transition among a plurality of interactive views, including a selection view, one or more image views, and one or more model views.

In some examples, canvas frame 520 may include a tool selector 524 that provides a list of available tools. As depicted in FIGS. 5A-5G, the list of tools includes a move tool, a magnifier tool, a window/level tool, an object drawing tool, a line drawing tool, a trimming tool, a hazard tool, an angle and/or distance measurement tool, an undo/redo tool, and/or the like. In some examples, certain tools may be enabled and/or disabled based on the current view displayed in workspace 522. For example, a tool that is not used by the current view may be hidden, grayed out, and/or otherwise not selectable. In some examples, clicking on a tool may cause a menu to appear with a list of sub-tools. For example, the object drawing tool may include sub-tools for drawing various 2D and/or 3D objects, such as freeform objects, predefined 2D shapes (e.g., circles, rectangles, ellipses, etc.), 3D shapes (e.g., spheres, 3D ellipsoids, etc.), and/or the like. In some examples, tool selector 524 may include tools for semi-automatically detecting objects in the underlying image data (e.g., clicking a point in the image data and using edge detection techniques to automatically identify a corresponding object). Although tool selector 524 is depicted as a sidebar, it is to be understood that tool selector 524 may be positioned and/or displayed in a variety of formats, including a palette, header, footer, dropdown menu, auto-hiding menu, and/or the like. In some embodiments, tool selector 524 may be omitted, such as when tool selection is performed using keyboard shortcuts.

Figure 5A:
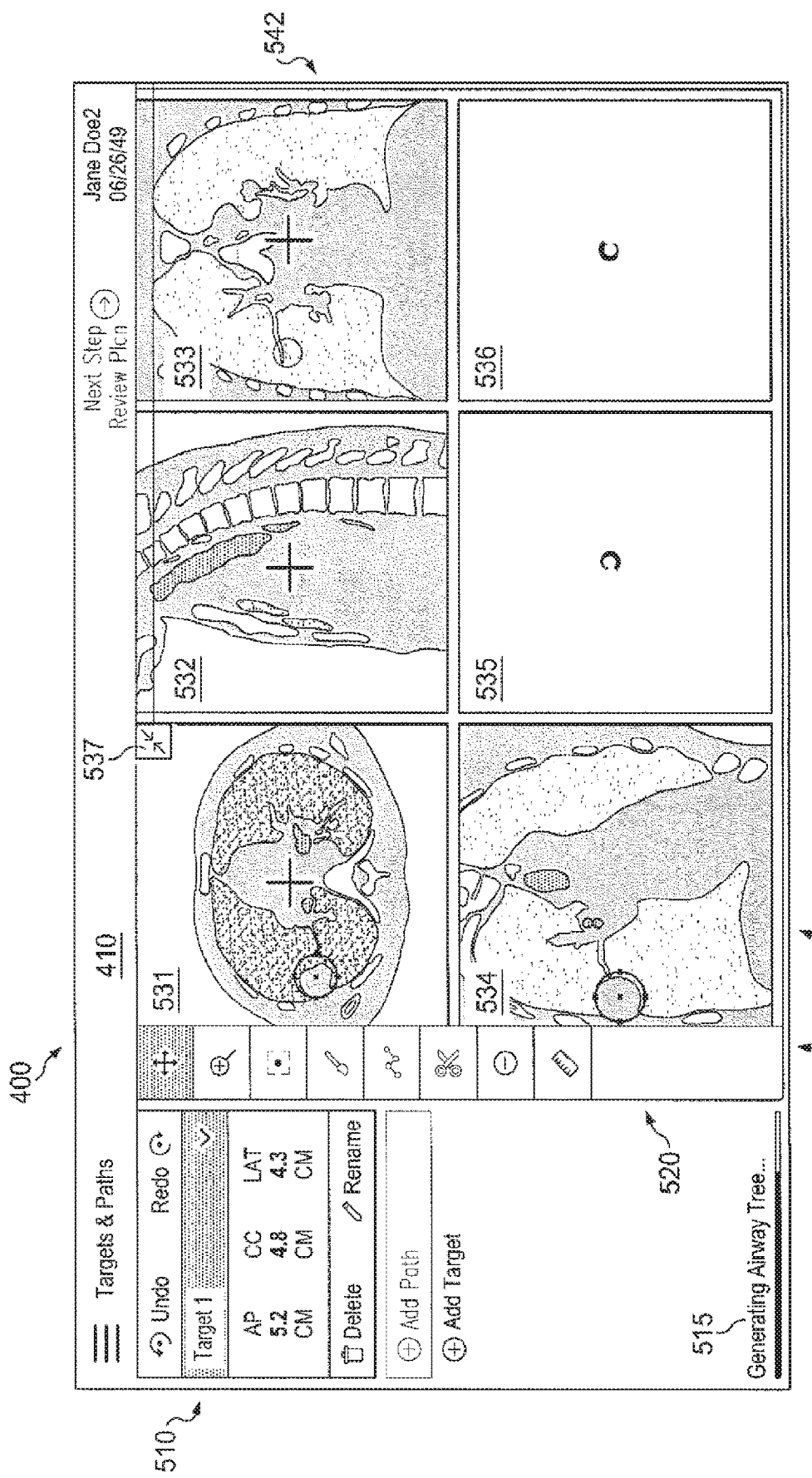
FIGS. 5A-5G are simplified diagrams of a graphical user interface in a hybrid segmentation and planning mode according to some embodiments

FIG. 5A illustrates an example of a selection view displayed in workspace 522. In the selection view, a set of selections 531-536 are presented as a thumbnail grid. Each of selections 531-536 corresponds to a different rendering of image data and/or representation (e.g., model) data. The renderings may vary based on their perspective, zoom level, data type, styles, and/or the like. For example, renderings of image data may be provided from a variety of perspectives including a transverse, sagittal, coronal, and/or virtual endoscopic perspective. In the example depicted in FIG. 5A, selections 535 and 536, which correspond to rendered representation data, display waiting indicators because the segmentation is not yet complete and the representation is not ready to display. On the other hand, selections 531-534, which correspond to renderings of image data, are populated with actual image data because graphical user interface 400 allows can display and/or receive interactive inputs for the image data before segmentation is complete. Once a selection for a rendering is received, the selected rendering can be displayed, interactive inputs received or both via an interactive window. For example, a user input, such as a click or a tap can be receive via an expand view button 537 of the selected rendering to proceed. In some examples, expand view button 537 may appear when detecting the user or an object held by the user hovering over the corresponding selection and may disappear otherwise. Although selections 531-536 are depicted as being arranged in a thumbnail grid, a variety of alternatives are possible, such as a list of selections.

FIGS. 5B-5F illustrate examples of an interactive window 541 displayed in workspace 522. Interactive window 541 displays the rendering that was selected using the selection view. In some examples, a selection sidebar 542 may be displayed alongside interactive window 541 to allow the user to change to a different rendering without returning to the selection view. For example, selection sidebar 542 may display a scrollable column of thumbnail images generally corresponding to selections 531-536, with the current selection being identified by a blue border.

Figure 5B:
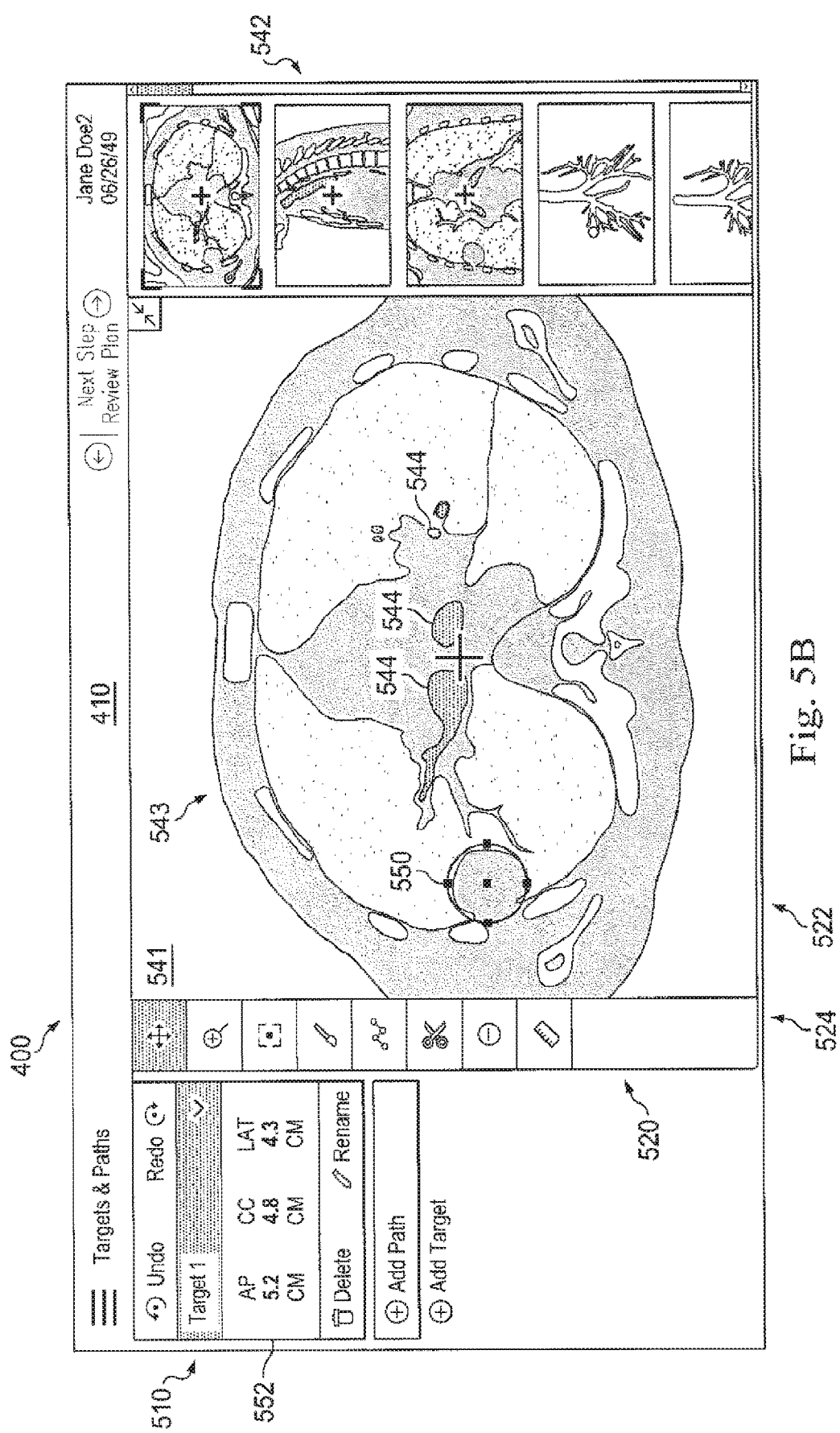

As depicted in FIG. 5B, raw image data 543 (e.g., CT image data) is displayed a first color palette, such as grayscale, and segmentation data 544 (e.g., detected airways) is displayed in a contrasting color or shade, such as pink. In some examples, when segmentation is still in progress, segmentation data 544 may be dynamically updated to reflect segmentation progress. For example, new pink regions may dynamically appear in interactive window 541 as new airways are detected over time.

In some examples, interactive window 541 may display one or more features of the plan of the medical procedure, such as targets, paths, and/or hazards. The features may include user input-based features, automatically extracted features, semi-automatically extracted features and/or the like. According to some embodiments, changes to the one or more features made in a particular rendering may be dynamically propagated to other renderings. For example, a target added in one rendering may automatically appear in the other renderings, including thumbnail images of selection sidebar 542.

As depicted in FIG. 5B, the features include a target 550 identified using a circle tool over a lesion visible in the underlying image data. The size, shape, and/or position target 550 may be adjusted to capture the shape of the lesion with the desired level of accuracy. When the size, shape, and/or position of target 550 is adjusted, statistics 552 corresponding to target 550 of are updated in control frame 510. In some examples, target 550 may be named, renamed, and/or deleted using controls provided in control frame 510. In some examples, controls provided in control frame 510 enable identification of additional targets after the first target has been identified by detecting corresponding user inputs via the control frame 510. Additionally or alternatively, tool selector 524 may include one or more tools for adding, modifying, and/or deleting targets. In some examples, identifying target 550 in one rendering may automatically cause an updated representation of target 550 to appear in other renderings. Consequently, the parameters of target 550 can be adjusted from multiple perspectives based on detecting user inputs from the available renderings that are switchably displayed.

Figure 5C:
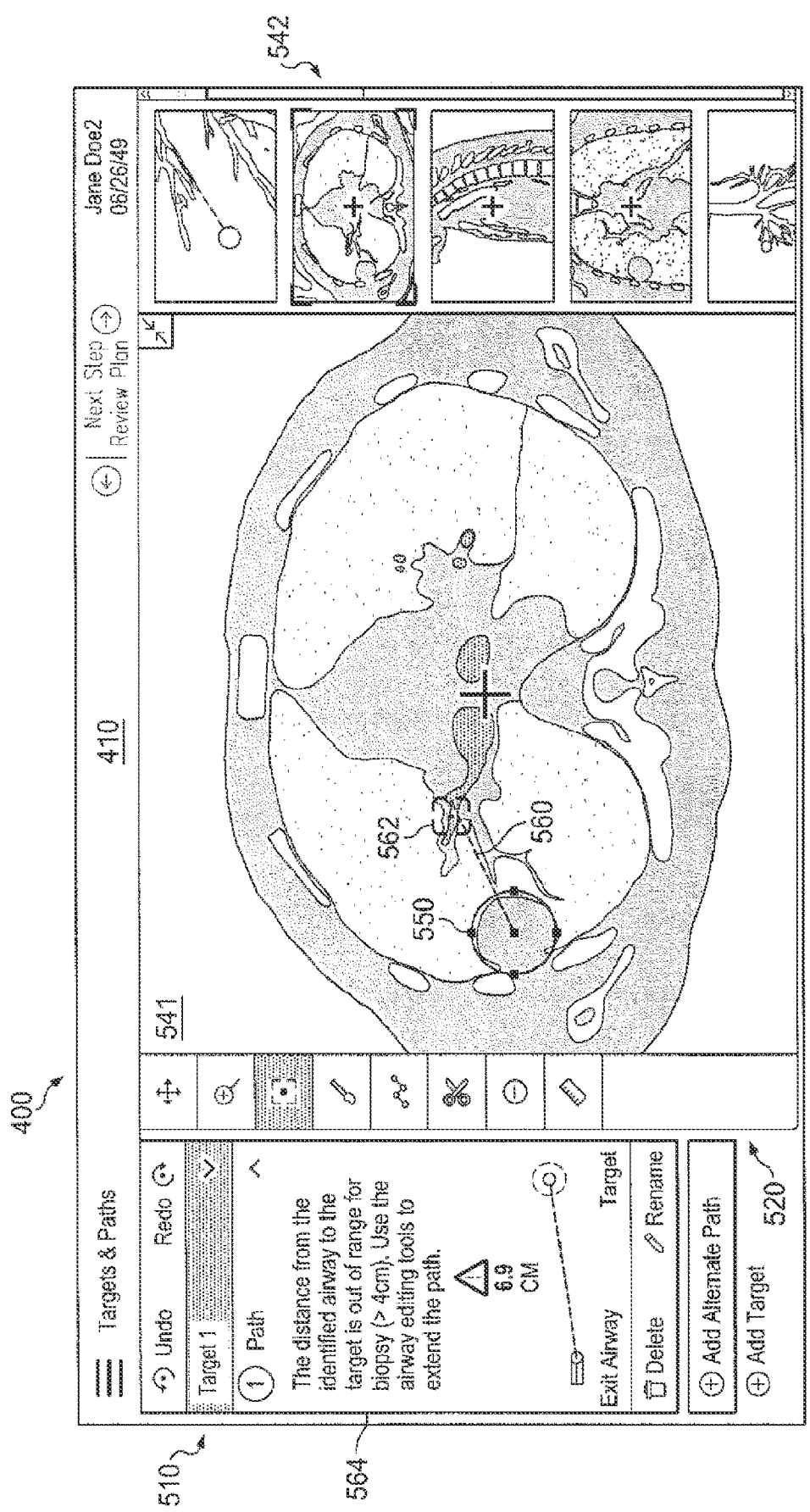

In FIG. 5C, interactive window 541 includes a trajectory 560 between target 550 and an exit location 562. Exit location 562 corresponds to a point where a medical instrument exits the anatomical passageways detected by the segmentation process to reach target 550. In some examples, exit location 562 is a closest point from a closest anatomical passageway to target 550. Trajectory 560 represents the trajectory for a medical instrument positioned at exit location 562 to perform one or more interventional steps at target 550. The instrument may, for example, puncture through the lumen of the anatomical passageway at the exit location. For example, the medical instrument may include a biopsy needle, an ablation tool, a chemical delivery system, an ultrasound probe, and/or the like. In some examples, the medical instrument may have a maximum trajectory length. For example, a biopsy needle may not be able to perform a biopsy at a target that is more than 3 cm from exit location 562. Consequently, when the length of trajectory 560 is greater than 3 cm, graphical user interface 400 may display an out of range warning 564. In some embodiments, out of range warning 564 can be provided based on a threshold, which may include a fixed threshold value and/or a variable threshold that is set based on, e.g., the type of tool which is to be used to access the target. For example, a biopsy needle may provide a different insertion depth than an ablation tool or an imaging probe, in which case the threshold may vary accordingly. In another example, different types of biopsy needles could provide different insertion depths. The user could input the type of tool being used or the tool could be automatically detected by the system. As depicted in FIG. 5C, out of range warning 564 is presented as a message in control frame 510.

In some embodiments, multiple trajectories to a given target may be identified, such as an alternate trajectory to be used when trajectory 560 is found to be unreachable and/or otherwise inadequate for use during the medical procedure. Consistent with such embodiments, control frame 510 may include controls for adding an alternate trajectory to target 550. Additionally or alternatively, tool selector 524 may include one or more tools for adding, modifying, and/or deleting trajectories.

Figure 5D:
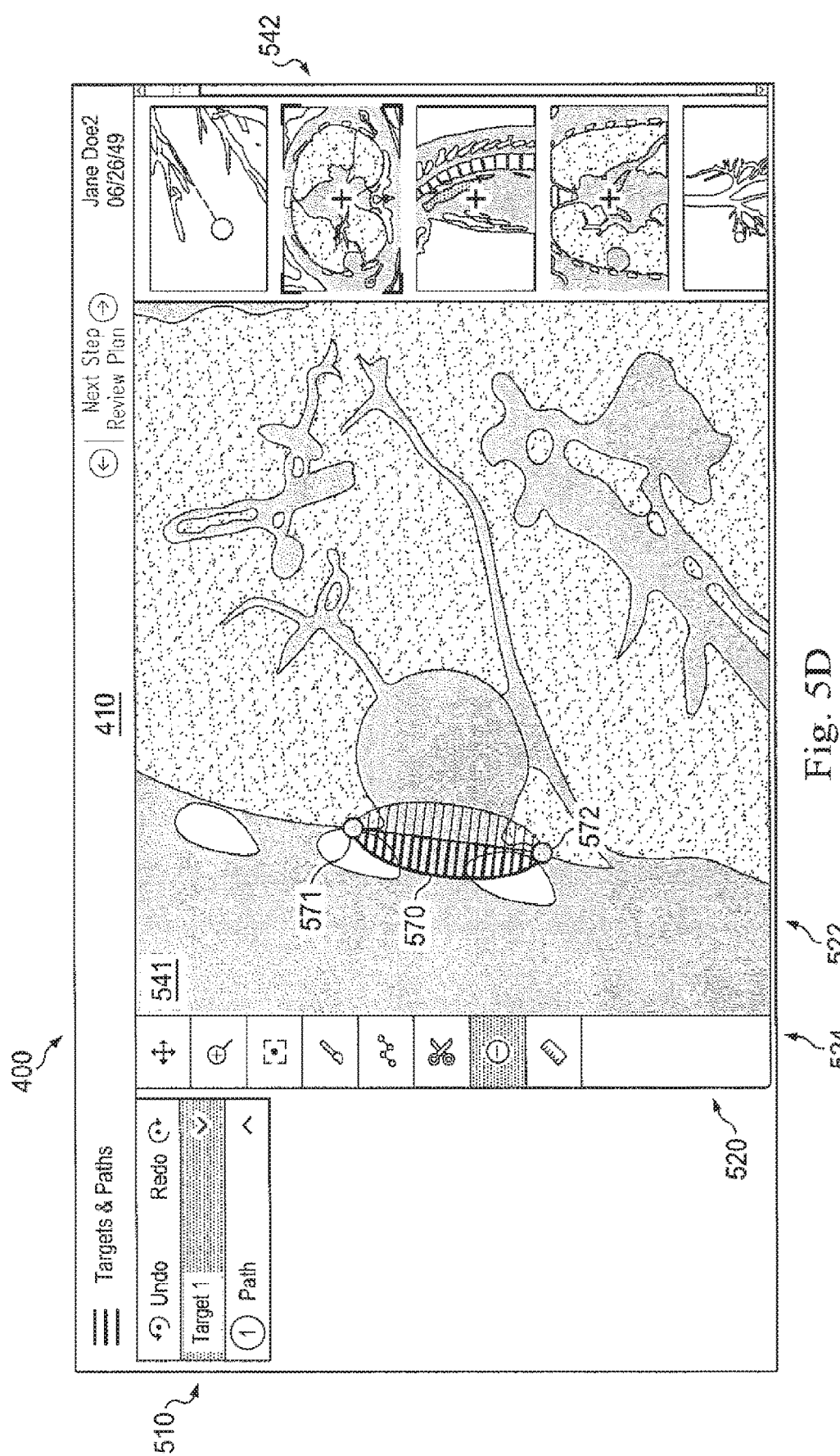
Figure 5E:
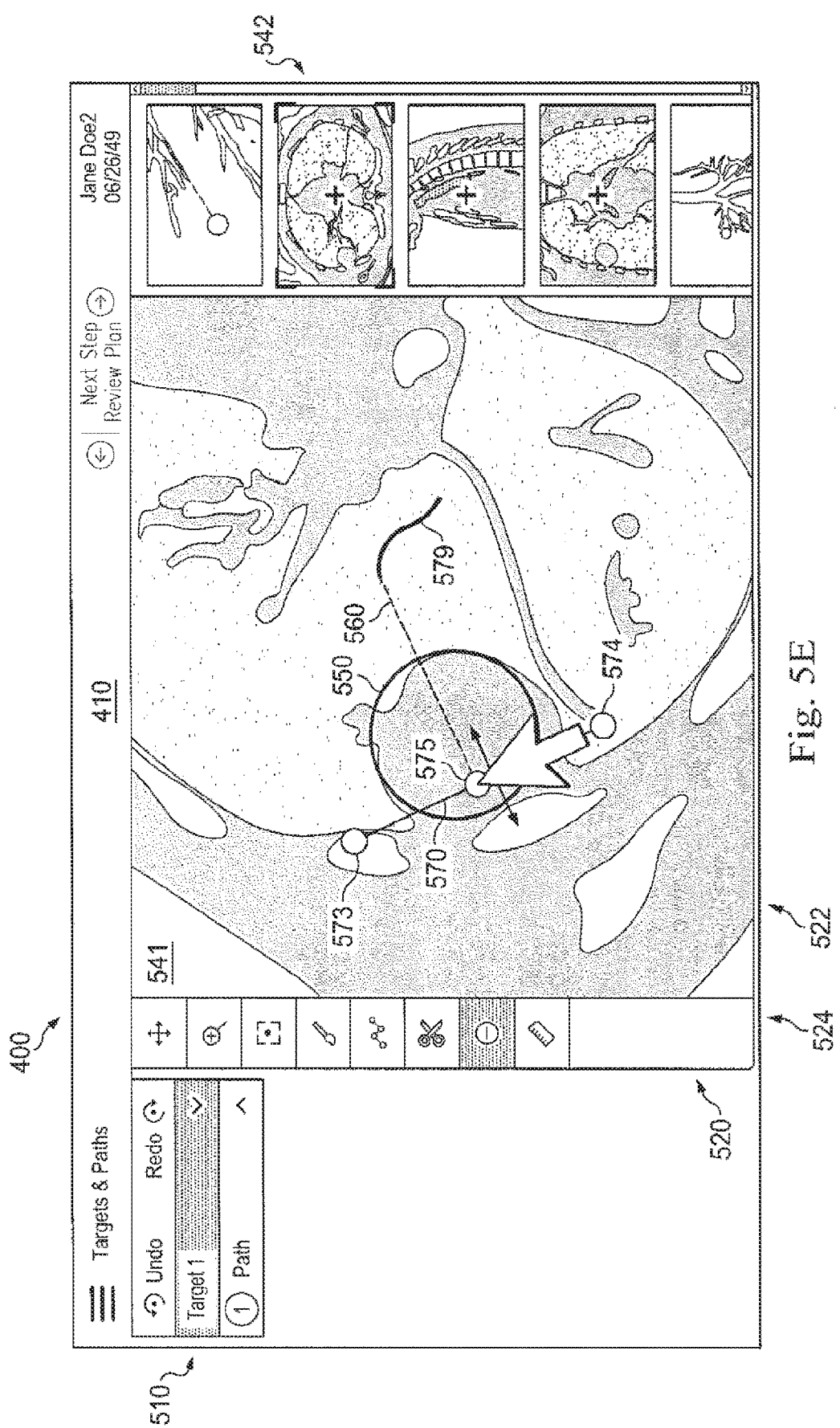
Figure 5F:
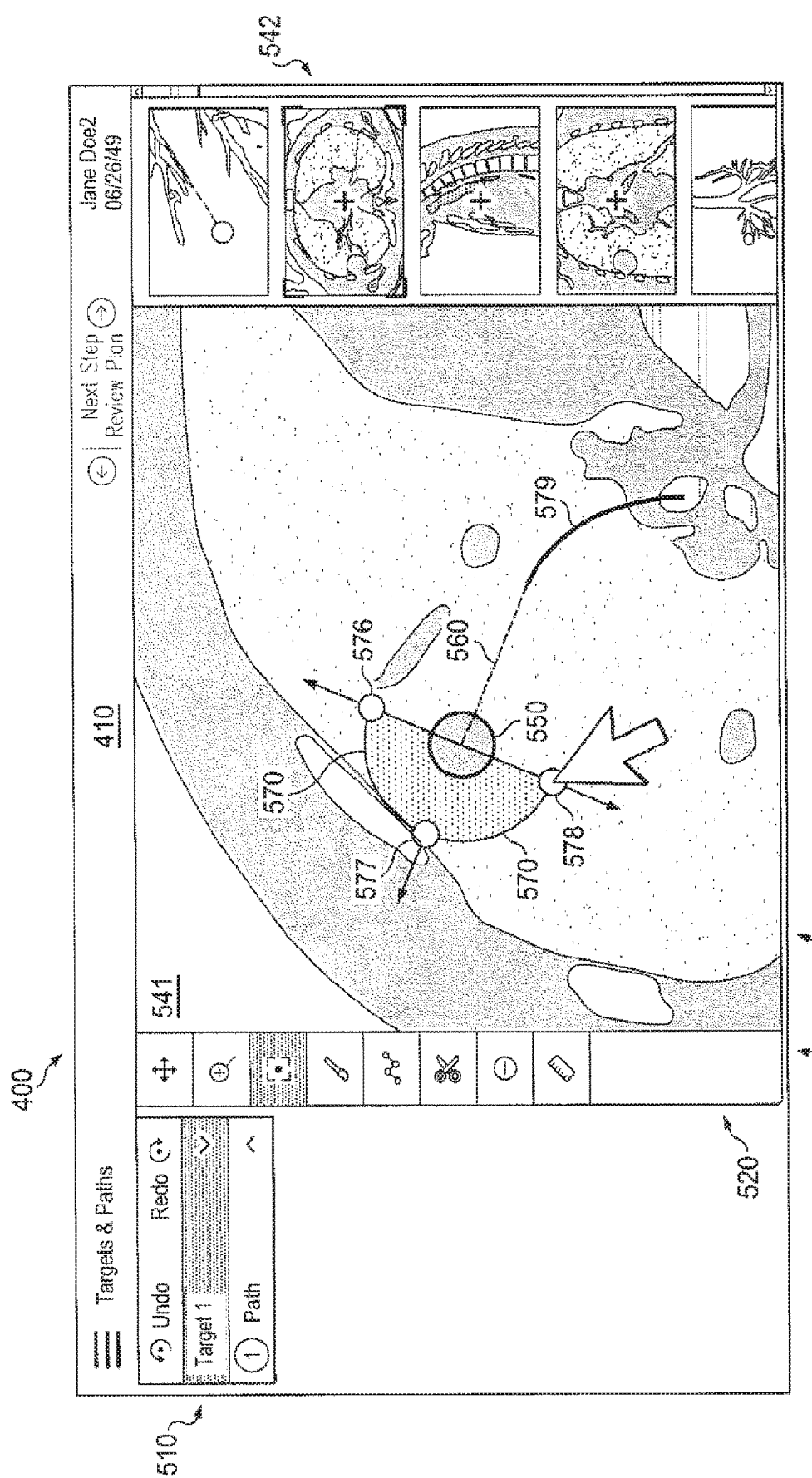

In FIG. 5D-5F, interactive window 541 includes a hazard fence 570. Hazard fence 570 is used to facilitate trajectory planning by identifying vulnerable portions of the anatomy that are in the vicinity of the target location. Examples of vulnerable portions of the anatomy may include blood vessels, lung pleura, large bullae, and/or the like. For example, puncturing the lung pleura during the medical procedure could cause dangerous pneumothorax to the patient. Consistent with such embodiments, the exit location and/or the trajectory between the exit location and the target location may be constrained to avoid the vulnerable portion of the anatomy. For example, a trajectory may be invalid when it passes within a threshold distance of a vulnerable portion of the anatomy, breaches a vulnerable portion of the anatomy, and/or the like. In the examples depicted in FIGS. 5D-5F, hazard fence 570 provides a warning to protect a portion of the lung pleura that is close to the target location from being punctured when using the planned trajectory. As depicted in FIGS. 5D-5F, hazard fence 570 is placed using the hazard tool of tool selector 524. Additionally or alternately, hazard fences may be added, modified, and/or removed using controls presented in control frame 510.

Each of FIGS. 5D-5F illustrates a different style of hazard fence 570. In FIG. 5D, hazard fence 570 is displayed as a planar hazard fence with a pair of control points 571 and 572 used to define a circular disk in three dimensions. To convey the 3-dimensional aspects of the circular disk, portions of the circular disk that project out of interactive window 541 may be rendered in solid color, whereas portions of the circular disc that project into interactive window 541 may be rendered in a faded and/or translucent color. In FIG. 5E, hazard fence 570 is displayed a conic hazard fence with a pair of outer control points 573 and 574 used to define a 3-dimensional circular disk as the base of the cone and a vertex control point 575 used to define the height of a cone. In FIG. 5F, hazard fence 570 is displayed as a hemispherical hazard fence with a triad of control points 576-578 used to define a hemisphere. In FIGS. 5E and 5F, interactive window 541 further includes target 550 and trajectory 560. When trajectory 560 connects to an exit location that is not in the plane of the underlying image (that is, when trajectory 560 projects into and/or out of interactive window 541) a projection 579 is displayed to link trajectory 560 to modeled passageways.

Various other types of hazards may be identified and marked using a suitable indicator, such as hazard fence 570. For example, an anatomical passageway may create a tight bend that cannot be traversed by certain medical instruments, such as a biopsy needle and/or a catheter. Accordingly, the bend may be indicated using a blocking sign such that the user knows to plan a different route to the target that avoids the bend. Automatic, manual, and/or semi-automatic techniques may be used to determine whether a planned route includes any bends that are too tight. For example, given the known physical characteristics of various medical instruments to be used in the medical procedure, a bend radius that is too tight may be automatically identified. Additionally or alternately, a user may visually identify that a bend appears to be too tight, and/or may perform measurements to confirm that a bend is too tight. In some examples, candidate routes may be automatically ranked based on user-defined rules and/or feasibility characteristics of the routes, such as the length of the routes, the tightest bend encountered in the route, the width of the passageways along the route, the length of the trajectory between the end of the route and the target, and/or the like. Accordingly, the user may select among the candidate routes based on the rankings.

Figure 5G:
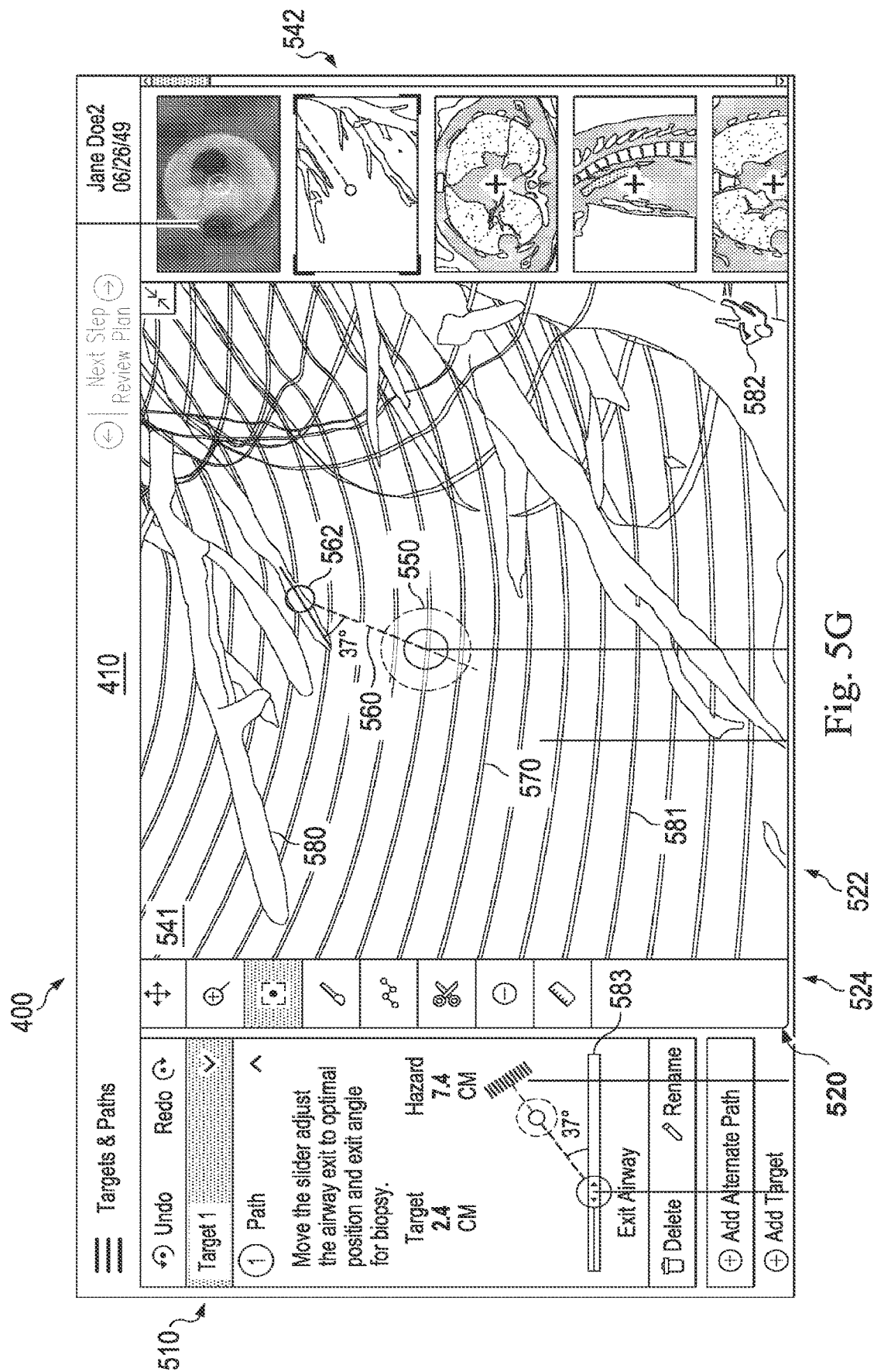

In FIG. 5G, interactive window 541 displays a representation (e.g., a model) 580 corresponding to the 3D model generated by segmentation of the image data. In some examples, representation 580 may not be available until segmentation is complete. In some examples, when segmentation is incomplete, a partial version of model 580 may be displayed and may be updated in real-time to reflect ongoing segmentation progress. In some embodiments, a boundary 581 may be displayed around model 580 as a translucent pattern, wire frame pattern, and/or the like. As depicted in FIG. 5G, boundary 581 corresponds to the lung pleura. The appearance of boundary 581 (e.g., color, size, texture, and/or the like) may vary to identify various features. For example, boundary 581 may be colored red to indicate the position of hazard fence 570. A variety of features, including target 550, trajectory 560, exit location 562, and/or the like, may also be depicted in interactive window 541. According to some embodiments, interactive window 541 may include an orientation icon 582 to identify the viewing perspective of model 580 relative to the patient body. In some examples, the appearance of passageways in model 580 that are along the route to target 550 may be altered to indicate that they are along the route. For example passageways that are on the route may be colored blue, whereas other passageways in model 580 may be colored gray.

In some examples, an exit angle selector 583 may be provided in control frame 510. Exit angle selector 583 provides an adjustment control, such as a slider, to adjust the position of exit location 562 along an anatomical passageway. Adjusting the position of exit location 562 causes a corresponding adjustment to the exit angle of trajectory 560 relative to the anatomical passageway. In some examples, it may be desirable to set the exit angle of trajectory 560 based on a variety of factors and/or metrics, such as a default or 'rule of thumb' exit angle (e.g., 45 degrees), the distance between exit location 562 and target 550, and/or the distance between exit location 562 and hazard fence 570. Accordingly, exit angle selector 583 may accelerate the process of defining trajectory 560 by allowing the user to rapidly test a range of exit angles and confirm that relevant metrics fall within acceptable ranges. For example, exit angle selector 583 may display the value of the exit angle (e.g., 37 degrees in the example provided), the distance from exit location 562 to target 550 (e.g., 2.4 cm in the example provided), and/or the distance from exit location 562 to hazard fence 570 (e.g., 7.4 cm in the example provided). The appearance of exit angle selector 583 (e.g., color, texture, size, font, etc.) may vary to alert the user when one or more of the relevant metrics are not within a predetermined range and/or do not meet a predetermined threshold. In some examples, one or more values of the angle adjustment slider may be disabled when the values are determined to be outside of an acceptable range.

FIG. 6 illustrates graphical user interface 400 in a preview mode according to some embodiments. The preview mode is used to preview the plan of the medical procedure that was prepared in the hybrid segmentation and planning mode. Graphical user interface 400 in a preview mode displays a simulated live endoscopic view 610, a matching virtual endoscopic view 620, a global anatomical representation (e.g., model) view 630, and a reduced anatomical representation (e.g., model) view 640. Simulated live endoscopic view 610 and virtual endoscopic view 620 depict renderings of the representation (e.g., model) from inside the anatomical passages. The renderings are from the perspective of a virtual endoscope that is following the route of the planned medical procedure. Simulated live endoscopic view 610 and virtual endoscopic view 620 are generally similar, except simulated live endoscopic view 610 includes photorealistic details (e.g., blood vessels in the anatomical lumens) to simulate an actual camera feed from an endoscope, whereas virtual endoscopic view 620 is augmented with directional cues towards the target location, such as contour lines 621, a route line, arrows, and/or the like. Where the anatomical passageways branch, the passageways may light up in virtual endoscopic view 620 to indicate the direction that the user should steer. One or more of simulated live endoscopic view 610 and virtual endoscopic view 620 may display various trajectory metrics, such as the remaining distances to the target location and/or hazards.

Global anatomical model view 630 generally corresponds to the 3D perspective view of model 580 described in FIG. 5G. As depicted in FIG. 6, global anatomical model view 630 includes a model rendering 631 that includes the anatomical model, a boundary, multiple target locations, a hazard fence, and an orientation icon. Anatomical model view 630 further includes a depiction of a catheter 632 as a green line. Endoscope views 610 and 620 provide matching views from a distal end of catheter 632.

In some embodiments, graphical user interface 400 in the preview mode may display a reduced anatomical model view 640. Reduced anatomical model view 640 provides a simplified overview of the planned route of the medical procedure that includes key anatomical features of the route. A route path 641 is represented as a straight line. A depiction of catheter 632 is overlaid on route path 641 to indicate the progress of catheter 632 along route path 641. An anatomical passageway 643 is rendered as a 2D tiered projection to provide a simplified indication of the width of passageway 643. Branches 644 are rendered to show the locations where they connect to passageway 643, but other details of branches 644, such as their various sub-branches, are not rendered. A target icon 645 that indicates the exit angle and/or nearby hazards is located at the distal end of route path 641. When the plan of the medical procedure includes multiple targets and/or paths, a selector 646 is included to switch among the multiple targets and/or paths. Embodiments of reduced anatomical representation (e.g., model) views are further discussed in U.S. Provisional Patent Application No. 62/486,879, which is incorporated by reference above.

As depicted in FIG. 6, reduced anatomical model view 640 serves as a controller to allow the user to navigate through a preview of the route. In particular, the distal end of catheter 632 includes a control point 650 that can be dragged back and forth along route path 641. As control point 650 is dragged back and forth, endoscope views 610 and 620 are updated to reflect the viewpoint of catheter 632 at the updated position of control point 650. Furthermore, the depiction of catheter 632 in global anatomical model view 630 is updated to reflect the shape of catheter 632 at the updated position of control point 650. In the example depicted in FIG. 6, control point 650 is displayed as a triangular cone representing the projected view of the endoscope from the distal end of the catheter. In alternative embodiments, control point 650 could be various shapes and sizes.

Once the one or more routes of the plan have been previewed, the clinician may proceed to save the plan. For example, the clinician may click and/or tap a next step button of header 410 to proceed. Alternately, the clinician may revert to an earlier stage of the planning process to make alterations as desired.

Figure 7:
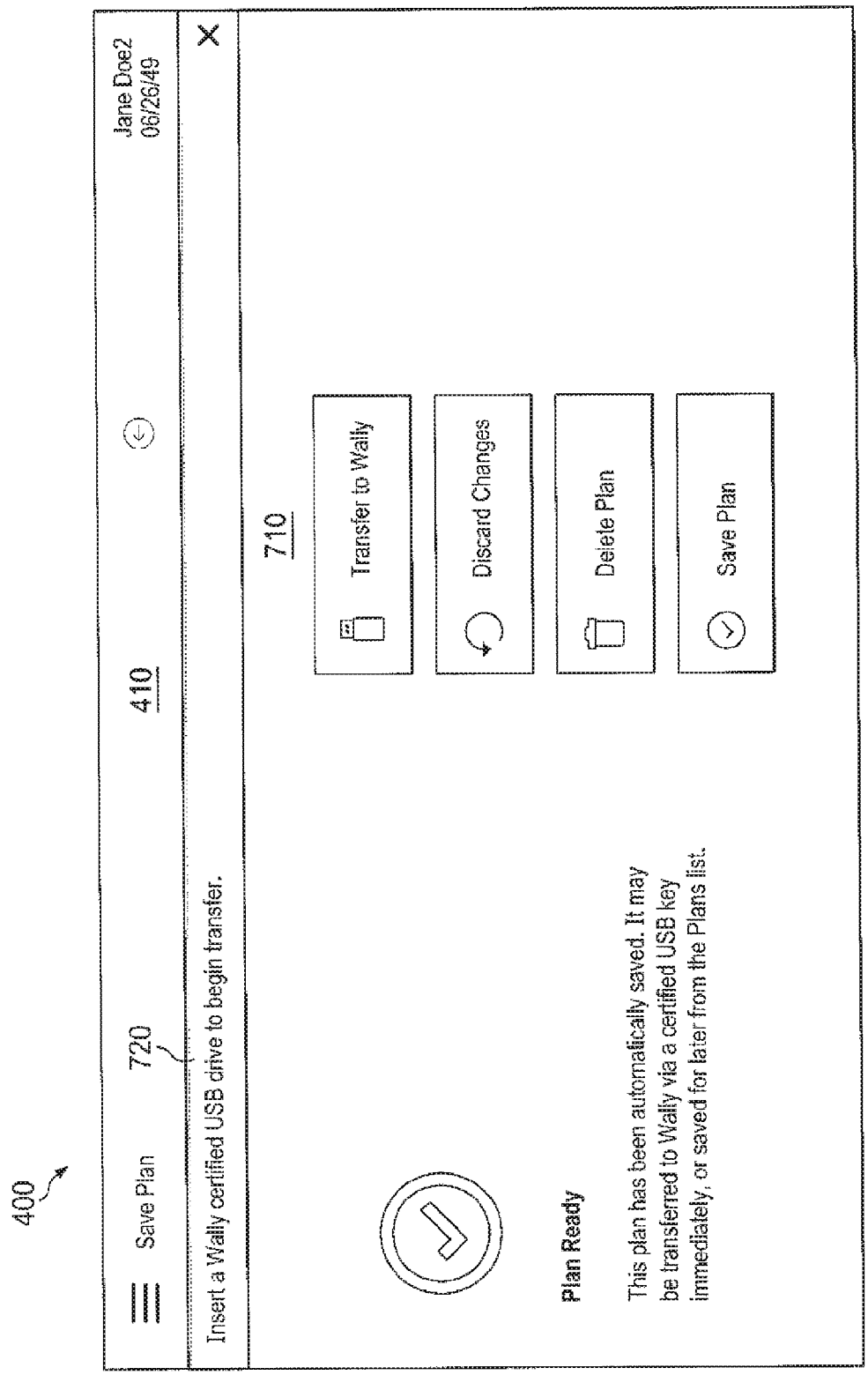
FIG. 7 is a simplified diagram of a graphical user interface in a save mode according to some embodiments.

FIG. 7 illustrates graphical user interface 400 in a save mode according to some embodiments. The save mode is used when the planned medical procedure is complete and/or ready to transfer to a medical instrument to perform the medical procedure. A set of options 710 are presented via graphical user interface 400. Options 710 may include a transfer option, a discard option, a delete option, and/or a save option. The save option may include saving the plan locally, saving to an external device, and/or transmitting the plan over the network, e.g., to a cloud storage facility. One or more options may require an external storage device to be installed. For example, the transfer option may require a storage device (e.g., a USB device) that is compatible with the medical instrument that the plan is to be transferred to. Accordingly, a message 720 may be displayed to inform the user of the applicable storage device requirements.

Figure 8:
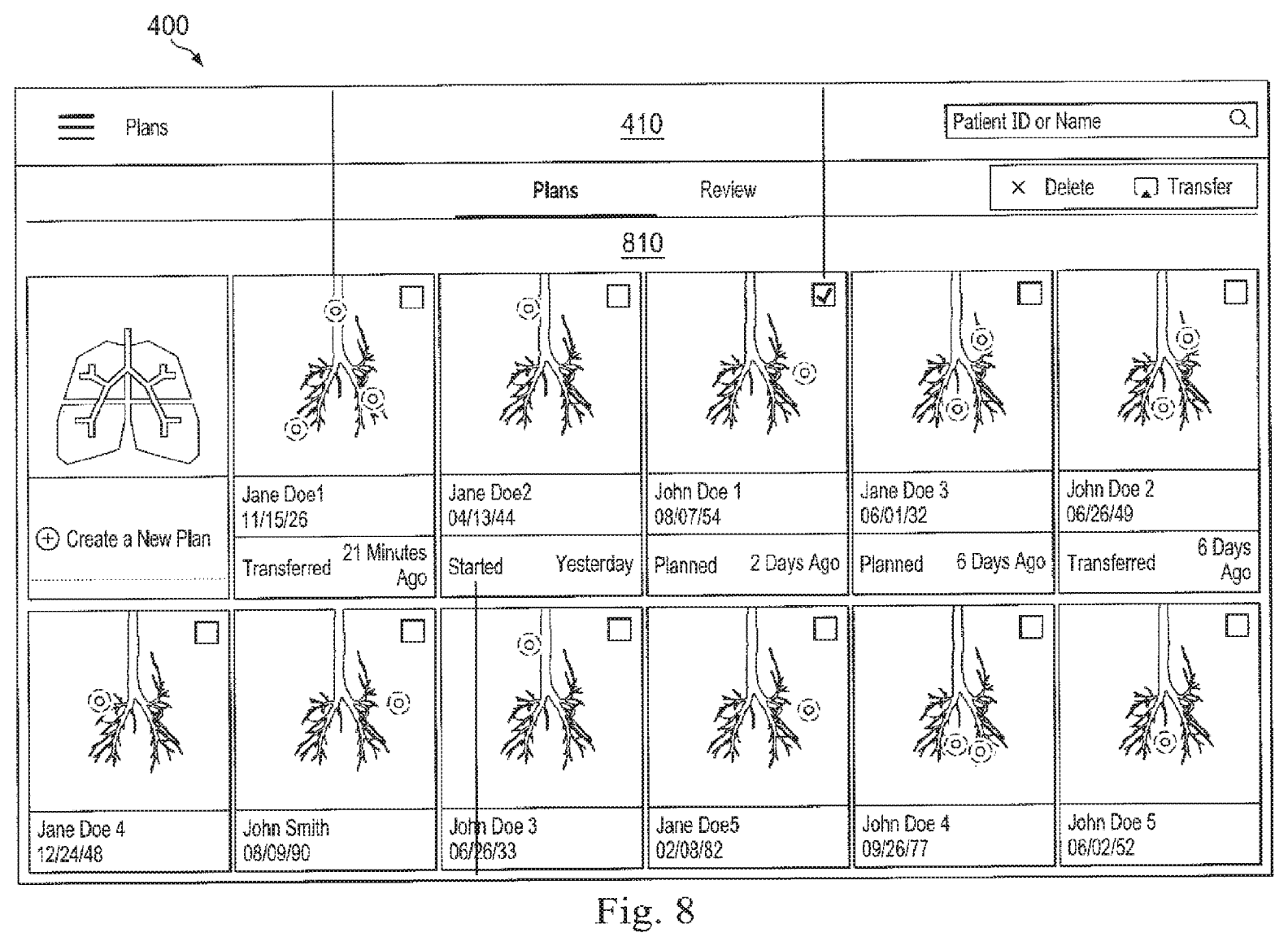

FIG. 8 illustrates graphical user interface 400 in a management mode according to some embodiments. The management mode is used to manage available plans. The available plans may be stored locally, on an external drive, and/or may be available for download over a network. A selection grid 810 is displayed that includes a thumbnail representation of the plan (e.g., a rendering of the representation (e.g, model), planned route, target locations, and/or the like). Additionally or alternately, selection grid 810 may include patient data such as the patient name, date of birth, and/or the like. In some examples, a procedure being planned can be reloaded and viewed using the preview mode of graphical user interface 400. In some examples, a procedure being planned can be saved at any time and reloaded to continue work at a later time using the hybrid segmentation and planning mode of graphical user interface 400. Accordingly, selection grid 810 may include a status of each plan (e.g., transferred, planned, started, and/or the like) and/or an indicator of when the plan was last saved. In some examples, a selected plan may be reviewed, deleted, and/or transferred. In some embodiments, selection grid 810 may include an option to create a new plan. When the new plan is selected, graphical user interface 400 may proceed to the data selection mode described previously in FIG. 4.

Figure 9:
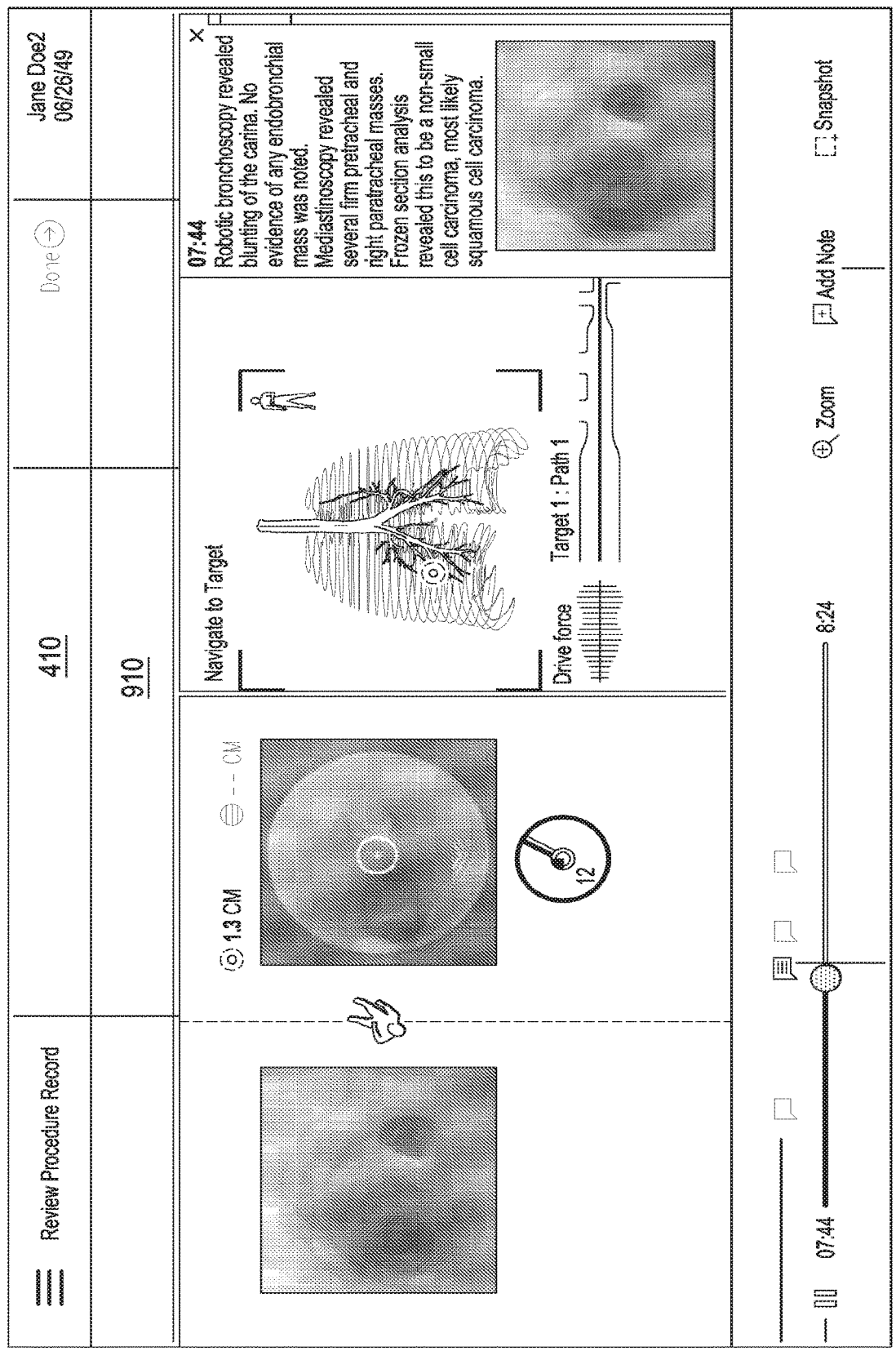
FIG. 9 is a simplified diagram of a graphical user interface in a review mode according to some embodiments.

FIG. 9 illustrates graphical user interface 400 in a review mode according to some embodiments. The review mode is used to review a record of a completed medical procedure. After a medical procedure is performed using a given plan, the record of the procedure may be saved and transferred to the planning workstation. In some embodiments, the recorded procedure file may include video of a live endoscopic image captured during the procedure, a correlated virtual endoscopic image, an anatomical representation (e.g, model) showing catheter movements during the procedure, notes taken by the clinician during the procedure, and/or the like. Accordingly, a viewer 910 may be displayed that includes playback controls (e.g., play, pause, zoom, and/or the like), snapshot controls, annotation and/or bookmark controls, and/or the like.

Figure 10:
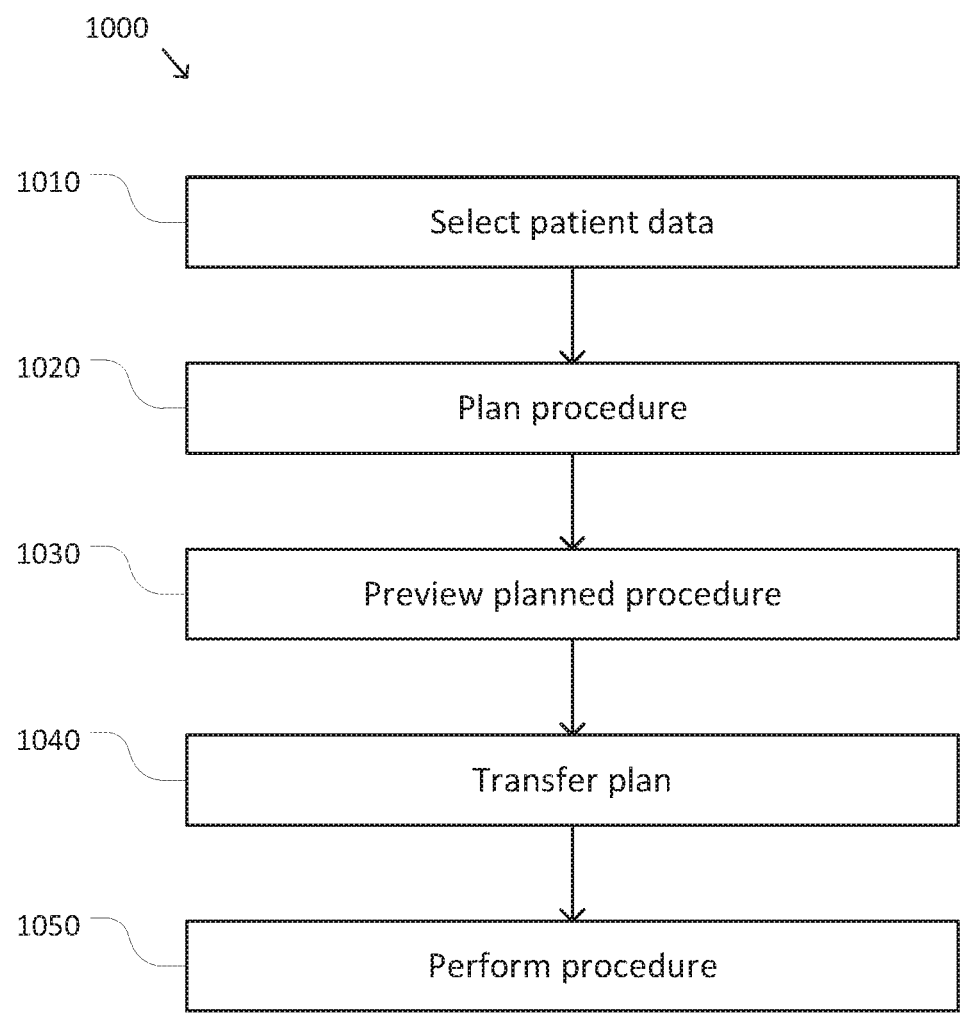
FIG. 10 is a simplified diagram of a method for planning a medical procedure according to some embodiments.

FIG. 10 is a simplified diagram of a method 1000 for planning a medical procedure according to some embodiments. According to some embodiments consistent with FIGS. 1-9, method 1000 may be used to operate a graphical user interface, such as graphical user interface 400, in a plurality of modes including a data selection mode, a hybrid segmentation and planning mode, a preview mode, a save mode, a management mode, and review mode. In some embodiments, the graphical user interface is interactive and may receive user inputs via a mouse, keyboard, touch, stylus, trackball, joystick, speech commands, virtual reality interface, and/or the like.

At a process 1010, data is selected via the graphical user interface in the data selection mode. According to some embodiments, selecting the data includes selecting a data source using a data source selector, such as data source selector 420, selecting a patient using a patient selector, such as patient selector 430, and selecting the data using a data selector, such as data selector 440. The selection may be confirmed by engaging a load button on the graphical user interface. Data can include imaging data, such as CT data and/or any other type of imaging or patient data.

At a process 1020, a medical procedure is planned via the graphical user interface in the hybrid segmentation and planning mode. According to some embodiments, the data selected at process 1010 includes image data that is segmented to generate an anatomical representation (e.g, model) based on extracted passageways. Concurrently during segmentation, the medical procedure is planned by receiving user inputs defining features of the plan, such as targets, hazards, and/or paths. In some examples, an interactive window, such as interactive window 541, may provide an interface for the user to add, modify, and/or delete features from the plan. When segmentation has progressed such that the representation (e.g, model) is ready for viewing, the interactive window may be used to view and/or interact with the representation (e.g, model). In some examples, a target may not have any extracted passageways close enough to draw a valid trajectory (e.g., a trajectory that is shorter than the maximum trajectory length) between the target and an extracted passageway. Accordingly, the user may manually identify and add a nearby passageway to the representation (e.g., model). An exemplary method for manually adding a connected passageway to the representation (e.g, model) is described in greater detail below with reference to FIG. 11.

At a process 1030, the planned medical procedure is previewed via the graphical user interface in the preview mode. According to some embodiments, previewing the medical procedure may include viewing a live simulated endoscope view, such as live simulated endoscope view 610, a virtual endoscope view, such as virtual endoscope view 620, an anatomical model view, such as anatomical model view 630, and/or a reduced model view, such as reduced model view 640. According to some embodiments, the reduced model view may include a control point, such as control point 650, to scroll back and forth through the preview of the medical procedure.

At a process 1040, the planned medical procedure is transferred to a medical instrument via the graphical user interface in a save mode. According to some embodiments, transferring the planned medical procedure may include installing a storage device that is compatible with the planning workstation and the medical instrument. In some examples, a message may be displayed via the graphical user interface to alert the user that compatibility is required. In some examples, the planned medical procedure may be saved during process 1040. In some examples, the planned medical procedure may be transferred to a robotic catheter system. In some examples, after process 1040, method 1000 may proceed to a process 1050 to perform the medical procedure in accordance with the plan.

Figure 11:
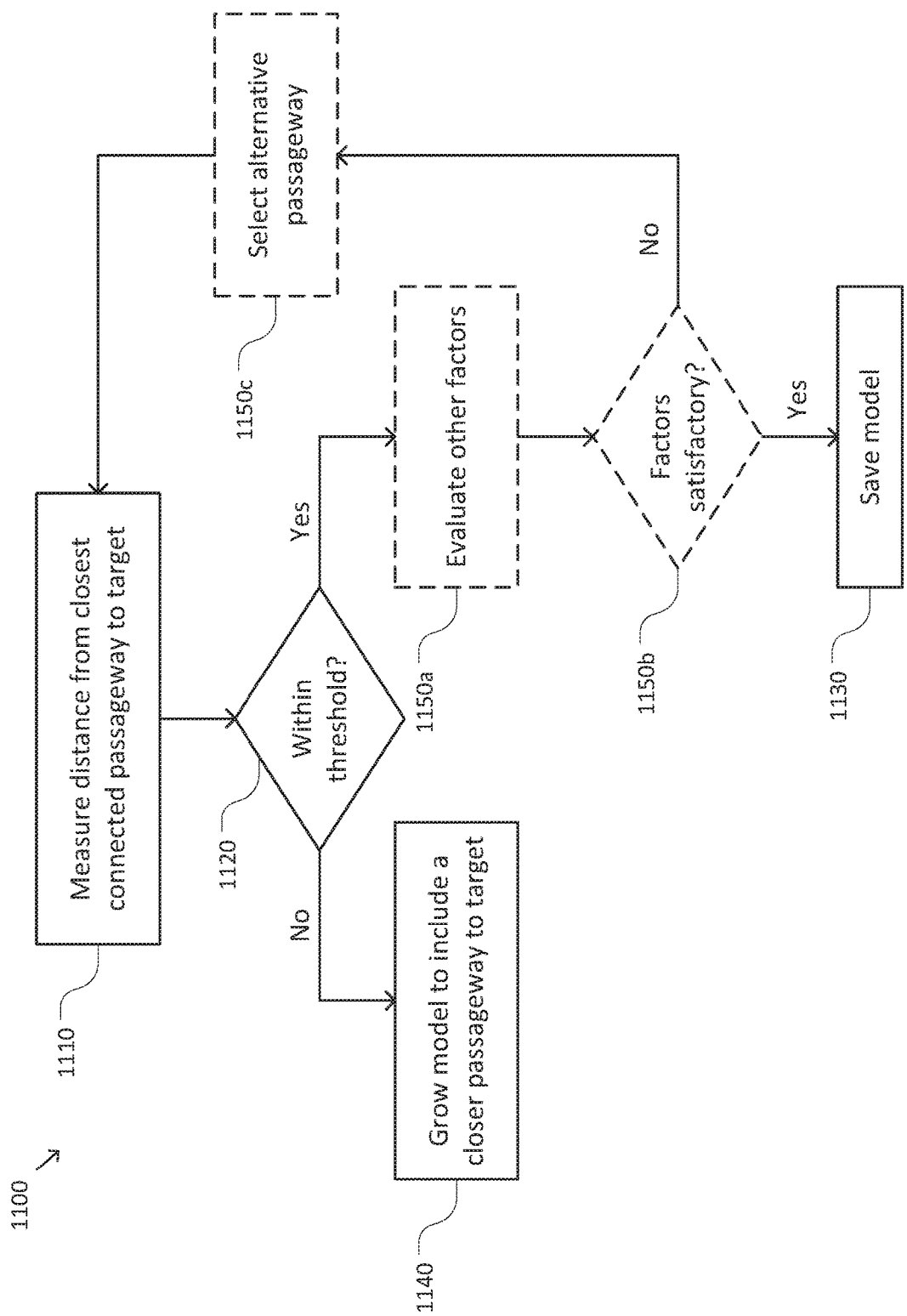
FIG. 11 is a simplified diagram of a method for modifying an anatomical representation (e.g., a model) to provide access to a target of a medical procedure according to some embodiments.

FIG. 11 is a simplified diagram of a method 1100 for modifying an anatomical model to provide access to a target of a medical procedure according to some embodiments. According to some embodiments, method 1100 may be performed using a graphical user interface, such as graphical user interface 400, in a hybrid segmentation and planning mode. In some examples, method 1100 may generally be performed after segmentation is complete and the anatomical model is available to be viewed and/or manipulated.

In general, the passageways of interest to a user are those that are continuously navigable by an instrument from a main passageway, such as the trachea, through various branches to an exit point at a passageway near the target. In some cases, automatic segmentation may not detect all such passageways. Accordingly, the set of passageways that are connected to the model generated by segmentation is incomplete. When the initial model does not provide satisfactory access to the target (e.g., when the closest exit point is not within a threshold distance, such as 3 cm, as previously described with respect to FIG. 5C), the user may desire to connect one or more passageways that are initially unconnected from the model. In some cases, automatic segmentation may detect passageways that are not of interest to the user, such as passageways that do not lead to the target. Method 1100 provides examples of techniques for identifying passageways of interest that were not detected by automatic segmentation and connecting the unconnected passageways to the model. Method 1100 further provides examples of techniques for trimming passageways from the model that are not of interest to the user.

At a process 1110, a distance between the target and the nearest connected passageway is measured. According to some embodiments, the distance may be measured automatically, e.g., in response to the user defining the target via the graphical user interface. In some examples, the distance may be measured via the graphical user interface by clicking on the target and the nearest connected passageway.

At a process 1120, it is determined whether the nearest connected passageway is within a predetermined threshold distance of the target. In some examples, the predetermined threshold distance may correspond to the maximum range of a medical tool used in the medical procedure, such as a biopsy needle. In some examples, the predetermined threshold distance may be a fixed value, such as 3 cm, and/or may be variable based on factors such as the type and/or model of the medical tool being used. If at process 1120, it is determined that the nearest connected passageway, based on the measured distance, is within the predetermined threshold distance, the model may be saved and method 1100 may terminate at process 1130 because the existing model provides satisfactory access to the target. When the nearest connected passageway, based on the measured distance, is not within the predetermined threshold distance, method 1100 may proceed to a process 1140 for identifying an unconnected passageway that is close to the target and growing the model to include the identified passageway, as described in greater detail below with reference to FIG. 12. Once the identified passageway has been connected to the model, method 1100 may repeat process 1110 and process 1120 until a passageway has been connected to the model that is within the predetermined threshold distance from the target.

In some embodiments, the distance between the target and the nearest connected passageway may not be the only consideration in determining if the model provides sufficient airways to reach a target. In some examples, other factors affecting an exit point from the closest airway to the target can be considered. Such factors can include satisfactory exit angle from the exit point, presence of tight radius bends that must be navigated through connecting airways to reach the exit point, diameter size of anatomical passageways and/or potential hazards between the exit point and the target. A different path through different airways may be selected based on these considerations. Thus, in an alternative embodiment, optional processes 1150a, 1150b, and 1150c can be completed to evaluate the other factors with respect to a selected passageway, determine whether the other factors are satisfactory, and select an alternative passageway when the other factors are unsatisfactory.

Figure 12:
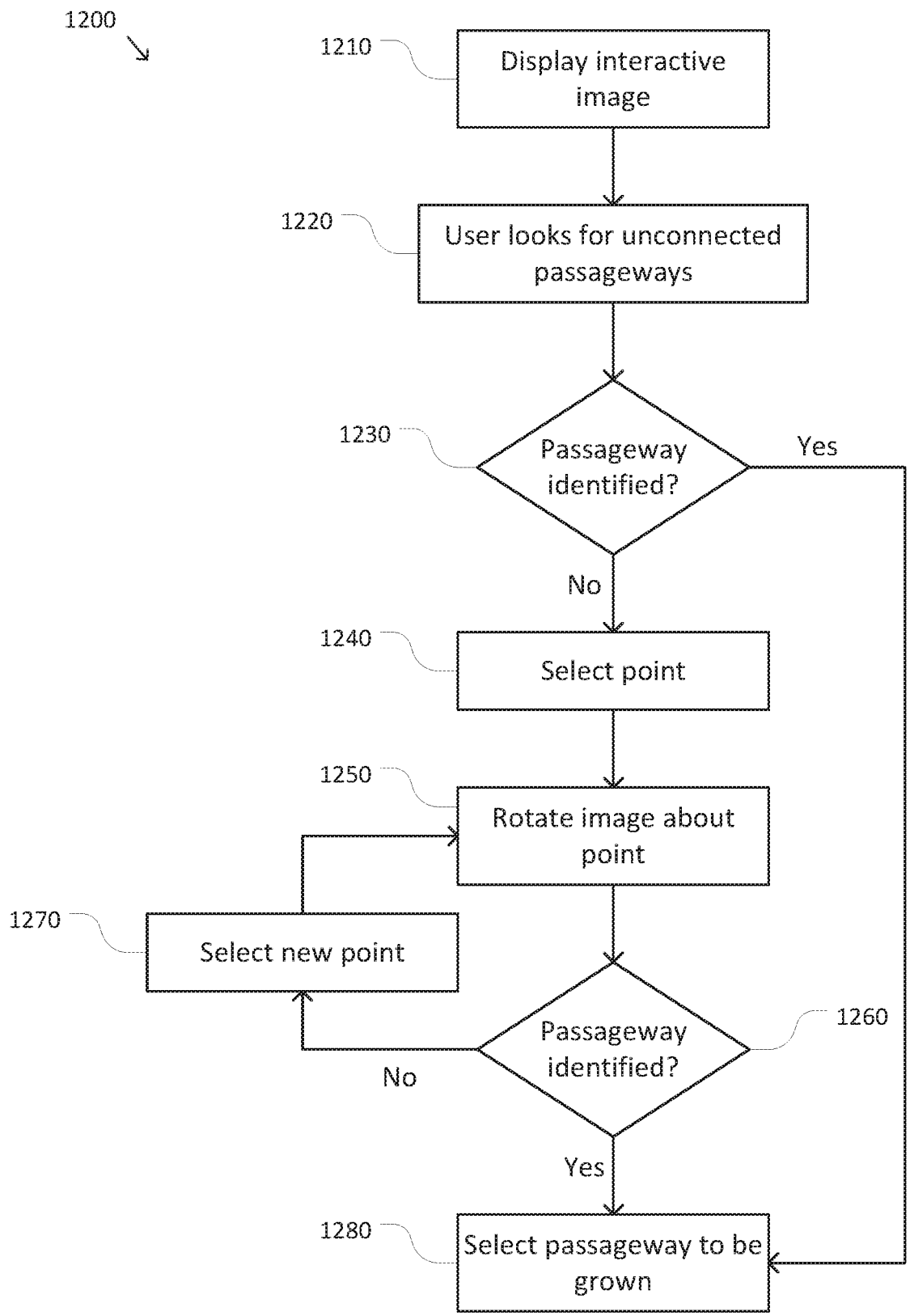
FIG. 12 is a simplified diagram of a method for growing an anatomical representation (e.g., a model) to provide access to a target of a medical procedure according to some embodiments.

FIG. 12 is a simplified diagram of a method 1200 for growing an anatomical model to provide access to a target of a medical procedure according to some embodiments. At a process 1210, an interactive image is displayed via a graphical user interface, such as graphical user interface 400. The interactive image depicts image data, connected passageways within the image data, and the target within the image data. At a process 1220, a user input is received to identify at least a part of an unconnected passageway that is closer to the target than the nearest connected passageway. In one example, the anatomical model can be grown using method 1200 based on detected identification of unconnected passageways adjacent to or near the connected passageways of the model and progressively working towards the target in a "forward" approach. In alternate examples, method 1200 can be used to grow the anatomical model based on detected identification of unconnected passageways adjacent to or near the target and progressively working towards the connected passageways of the model in a "backward' approach.

At a process 1230, when a suitable unconnected passageway is not identified in the initially displayed interactive image, the interactive image may be searched by iteratively rotating the interactive image and determining whether the unconnected passageway is visible. At a process 1240, a rotation point is defined in the graphical user interface by selecting a point in the image data (e.g., by double clicking the point). In some examples, the rotation point is displayed by placing crosshairs on the interactive image. In one example, the rotation point is chosen as a point along the closest connected airway to the target. In another example the rotation point is chosen as a point on the target. In further examples, the rotation point can be any point in the interactive image. At a process 1250, the interactive image is rotated about the rotation point. In some examples, the rotation point provides 360 degree rotation in three dimensions about the rotation point. At a process 1260, it is determined whether an unconnected passageway is identified in the interactive image. When an unconnected passageway is not identified, a new rotation point is selected at a process 1270 and the interactive image is rotated about the new rotation point in order to identify an unconnected passageway. Processes 1240-1270 may be repeated until an unconnected passageway is identified.

When an unconnected passageway is identified in the interactive image at process 1230 or process 1260, a user input may be received that identifies the unconnected passageway (e.g., a click and/or a tap) at a process 1280 and the unconnected passageway is connected to the model. In some embodiments, the unconnected passageway may be connected to the model automatically, using segmentation software to trace the passageway to a connection point with the model. When process 1280 is complete, method 1200 may return to method 1100 to determine whether the newly connected passageway provides satisfactory access to the target. Processes 1110-1150 may be repeated until satisfactory access to the target is achieved According to some embodiments, an unconnected passageway is partially identified when rotating the interactive image about the rotation point during process 1250. After rotating the interactive image to a state where the unconnected passageway is partially identified, it can be helpful to limit the rotation to rotation about an axis of rotation, rather than unconstrained 3D rotation about the rotation point. The axis of rotation is defined in the graphical user interface by drawing a line between the rotation point and a second point, such as the target location. Limiting the rotation to an axis of rotation may enhance usability relative to rotation about the rotation point alone. Consistent with such embodiments, searching for the unconnected passageway may proceed by iteratively repeating processes 1240-1270 using any combination of rotation points (when unconstrained rotation is desired) and axes of rotation (when limited rotation is desired).

Beginning with a point of rotation can provide some advantages to beginning with an axis of rotation. For example, if the user was to initially provide an axis of rotation and a given unconnected passageway is positioned in an orientation that is orthogonal to the axis of rotation, the user would not see any variation in the appearance of the unconnected passageway when rotating the interactive image, i.e. the unconnected passageway would appear as a circle and when rotating about the selected axis of rotation, the unconnected passageway would always appear as a circle. Using a single point of rotation would provide 360 degrees of rotation in three dimensions. Thus, regardless of the initial orientation of the unconnected passageway, the user would eventually rotate the interactive image in a manner where the unconnected passageway would be visible. Additionally, selecting a new axis of rotation can prove difficult. The user would have no guidance in how to draw a new line. However, changing a point of rotation is simple in that it is only selecting a single point. The rotation point could be selected at a position close to a connected passageway but, if that proves to be an insufficient point of rotation, the rotation point could be easily moved to be at the target.

In another example, referring again to FIG. 11 at process 1140, the model can alternatively be grown when the user draws a line from the closest connected passageway to the target. Using automated techniques, structures that appear to correspond to unconnected passageways may be detected, and the closest such structure may be connected to the model. The user can iteratively continue drawing a line from the most recently connected passageway to the target while additional unconnected passageways are detected and connected to the model, until the closest connected passageway falls within the threshold established in process 1120. In one example, when a passageway that is unacceptable to the user is connected to the model, the user may select the airway and erase or delete it from the model At any time during segmentation and/or during growth of the model, the model may be trimmed. In some examples, one or more connected passageways may be determined to be extraneous. For example, a connected passageway may be determined to lead far from the target and/or otherwise serve little and/or no purpose relevant to the medical procedure. In some examples, it may be desirable to disconnect and delete extraneous passageways from the model. For example, disconnecting the extraneous passageways may reduce visual clutter and/or may improve performance (e.g., improve load times, rendering times, and/or the like) by reducing the size of the model. Consequently, a trimming tool may be provided to the user via graphical user interface. For example, the trimming tool may be selected via a tool selector, such as tool selector 524. When the trimming tool is enabled and a user input is received that identifies an extraneous passageway (e.g., a user click and/or tap) the passageway may be disconnected and deleted from the model. In some examples, the passageway may be disconnected at the point identified by the user. In some examples, the passageway may be disconnected at the nearest point of connection to the model. In some examples, the identified passageway may be disconnected along with any sub-branches of the identified passageway. According to some embodiments, trimming may be performed at any time during methods 1100 and/or 1200, and/or as a standalone process independent from methods 1100 and/or 1200.

Figure 13:
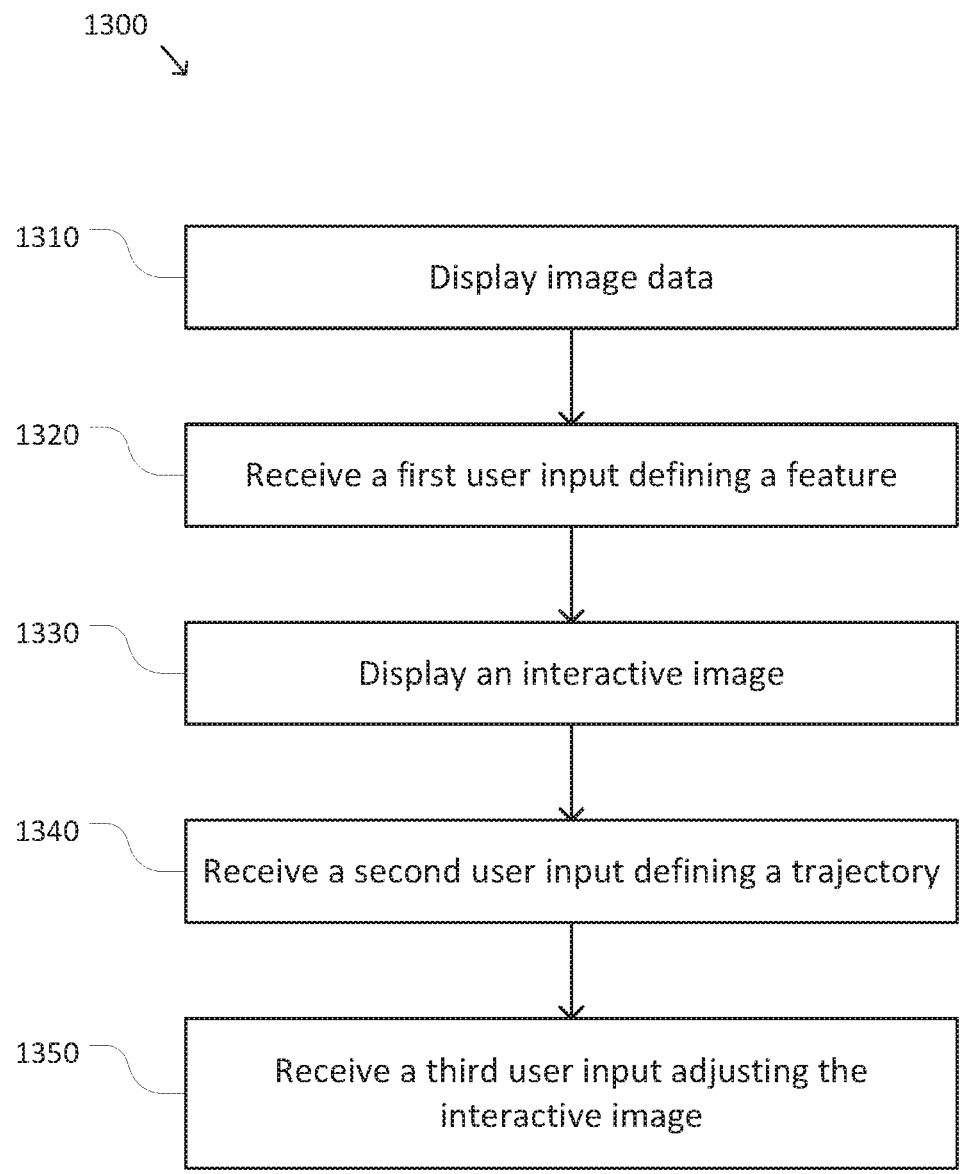
FIG. 13 is a simplified diagram of a method for planning a medical procedure using a graphical user interface according to some embodiments.

FIG. 13 is a simplified diagram of a method 1300 for planning a medical procedure using a graphical user interface according to some embodiments. According to some embodiments consistent with FIGS. 4-9, method 1300 may be performed using graphical user interface 400 in the hybrid segmentation and planning mode, as described in FIGS. 5A-5G. In some examples, method 1300 and/or various processes thereof may be performed before, during, and/or after segmentation of image data to generate a model.

At a process 1210, an interactive window, such as interactive window 541, is provided for a user to create a plan for a medical procedure. The interactive window may be displayed via a display system and may interactivity via a user interface such as a mouse, trackball, joystick, touch screen, natural user interface (e.g., voice, gestures), augmented/virtual reality interface, and/or the like. According to some embodiments, the interactive window may be displayed in conjunction with one or more other views, such as a tool selector (e.g., tool selector 524), a selection sidebar (e.g. selection sidebar 542), a control frame (e.g. control frame 510), and/or the like.

At a process 1310, image data is displayed via the graphical user interface. In some examples, the image data may correspond to raw image data of a patient (e.g., CT data). The image data may be previously selected in a data selection mode of the graphical user interface. In some examples, the image data may be displayed concurrently while the image data is being segmented using a background segmentation process. Segmentation data generated by the segmentation process (e.g., airways detected in the image data) may be overlaid on the image data. For example, the image data may be displayed in a first color palette, such as greyscale, and the segmentation data may be displayed in a contrasting color, such as pink. As segmentation of the image data proceeds, the displayed segmentation data may be updated to reflect the segmentation progress.

At a process 1320, a first user input is received that defines one or more features of the plan within the displayed image data. According to some embodiments, the one or more features of the plan may include a target of the medical procedure, a hazard of the medical procedure, and/or the like. In some examples, the target may be defined using an object placement tool with a suitable shape (e.g., a circle tool and/or a 3D ellipse tool) provided by the graphical user interface. In some examples, the hazard may be defined using a hazard fence placement tool with a suitable shape (e.g., a 3D circular disk, a conic hazard fence, and/or a hemispherical hazard fence) and/or suitable control points for defining the hazard fence. Examples of hazards may include vulnerable portions of the anatomy (e.g., lung pleura, blood vessels, large bullae, and/or the heart), and/or excessive bend in an anatomical passageway (e.g., a bend that is too tight to accommodate passage of a medical instrument, such as a biopsy needle).

At a process 1330, an interactive image is displayed via the graphical user interface. The interactive image includes the image data, connected anatomical passageways detected by segmentation of the image data, and the one or more features defined during process 1320. The connected anatomical passageways form a tree in which each branch is reachable from a main passageway, such as a trachea. Accordingly, the connected anatomical passageways are accessible to a medical instrument inserted via the main passageway. A user may interact with the interactive image via a user interface such as a mouse, trackball, joystick, touch screen, natural user interface (e.g., voice, gestures), augmented/virtual reality interface, and/or the like. According to some embodiments, the interactive image may be displayed in conjunction with one or more other views, such as a tool selector (e.g., tool selector 524), a selection sidebar (e.g. selection sidebar 542), a control frame (e.g. control frame 510), and/or the like.

At a process 1340, a second user input is received that identifies at least a part of a trajectory of the medical procedure within the interactive image. In some examples, the trajectory may be identified by connecting the target to a closest passageway among the connected anatomical passageways. For example, the second user input received can include a line drawn between the target and the closest passageway via a line tool provided by the graphical user interface.

At a process 1350, a third user input is received that adjusts one or more aspects of the interactive image based at least partly on the defined trajectory. According to some embodiments, process 1350 may generally correspond to method 1200 for growing the anatomical model, in which case the third user input may include one or more user inputs received during method 1200. For example, process 1350 may include determining a distance represented by the trajectory, e.g. a distance between the closest passageway and the target. Consistent with such examples, adjusting the interactive image may include connecting an unconnected passageway to the connected passageways when the distance is greater than a predetermined threshold (e.g., 3 cm). The unconnected passageway may be connected by receiving a fourth user input identifying an unconnected passageway that is closer to the target than the nearest passageway and using automated techniques to connect the identified passageway. In some examples, adjusting the interactive image may include determining an exit angle based on the trajectory (e.g., an angle at which a medical instrument punctures a lumen of the passageway when accessing the target from the passageway) and receiving the third user input to manipulate a control provided by the graphical user interface, such as a slider, to alter the position of an exit point along the passageway. In some examples, the control may provide continuous control over the position of the exit point and/or may provide real-time updated metrics associated with the selected exit point, such as the corresponding exit angle.

FIGS. 14A-14F are further simplified diagrams of the graphical user interface 400 in a branch labeling mode according to some embodiments. In this example, the branch labeling mode is applied to lung anatomy, although in further examples, the graphical user interface 400 is used to label any suitable anatomical structures. Lungs include a right lung and a left lung, where each lung is divided into lobes, which in turn can be divided into segments and lobules. Within each lobe are various anatomical structures including a set of anatomical passageways 1402 which can include a plurality of branches 1403. In the example of FIGS. 14A-15E, the branch labeling mode may be used to identify and label which lobe an individual branch 1403 may belong. In alternative embodiments, the branch labeling mode is used to identify and label which lung, segment, and/or lobule and individual branch 1403 may belong. In the branch labeling mode, the graphical user interface 400 provides a mechanism for a user to assign labels to the branches 1403 reflecting a section 1404 of the lung (e.g., lobe) to which the respective branch 1403 belongs. In an exemplary embodiment, the branch labeling mode is used to aid in registration of an airway model to human anatomy to provide navigation during an image guided biopsy procedure. Further details on registration can be found in 62/486,879, which has been previously incorporated by reference.

Branch labeling may operate on a 3D model, such as that described above, or any other suitable model of the anatomical passageways 1402. The model may be created from imaging data including CT data, MM data, OCT data, x-ray data, and/or other types of imaging or patient data as previously described. In some embodiments, the 3D model includes the set of anatomical passageways 1402 and other anatomical structures such as ribs, blood vessels, tumors, lesions, and/or organs (e.g. heart). In the illustrated embodiments, the 3D model includes lung branches 1403 and lung pleura 1405, although further embodiments include any type of suitable anatomical passageways 1402 and surrounding structure. The graphical user interface 400 displays the elements of the 3D model and the display of individual elements (e.g., the lung pleura 1405) may be hidden or displayed to improve clarity.

In some examples, the graphical user interface 400 automates aspects of the labeling process including label selection. Furthermore in some examples, the graphical user interface 400 automates aspects of label verification including identifying unlabeled branches 1403 and/or identifying conflicts in user input. In these examples and others, the graphical user interface 400 may accelerate the planning of a medical procedure by providing a user with an expedited process for identifying branches.

Figure 14A:
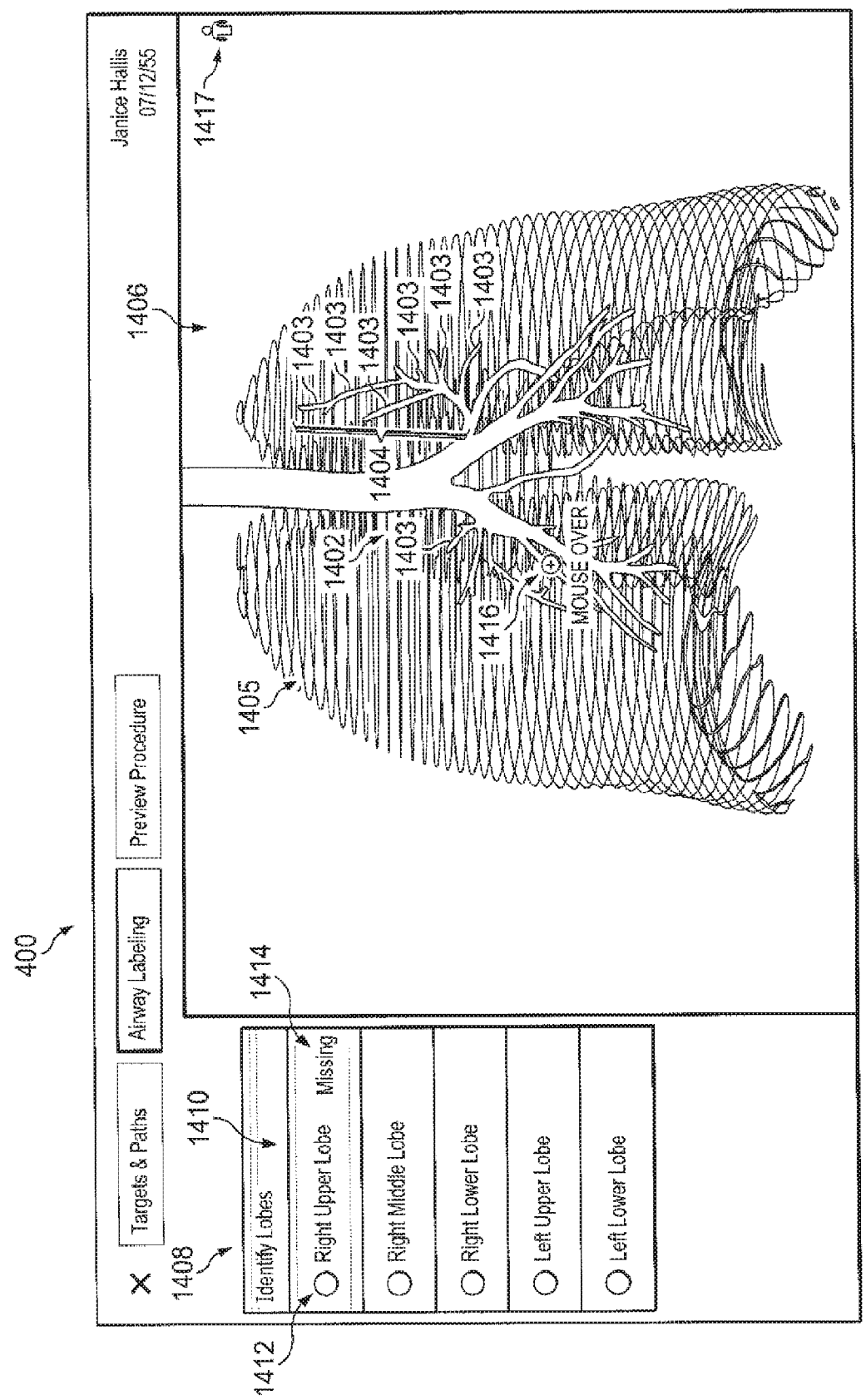
FIGS. 14A-14F are simplified diagrams of a graphical user interface in a branch labeling mode according to some embodiments.

FIG. 14A illustrates an example of the graphical user interface 400 in the branch labeling mode prior to labeling the section/lobe 1404 of any of the branches 1403. In some embodiments, the graphical user interface 400 includes an interactive window 1406 for viewing, selecting, labeling, and/or otherwise interacting with the model of the anatomical passageways 1402. The interactive window 1406 may display an image of the model that represents the anatomical passageways 1402 and surrounding anatomy (e.g., lung pleura 1405) as 3D renderings, wireframes, cross sections, and/or other suitable representation. In one such embodiment, the interactive window 1406 represents the branches 1403 by centerlines.

In some embodiments, the graphical user interface 400 includes a label tool 1408 for selecting labels to assign to branches of the model. The label tool 1408 may be represented as a palette, header, footer, sidebar, menu, message bar, dropdown menu, pop-up window, and/or other suitable representation. In some embodiments, the label tool 1408 displays a list 1410 of labels to be applied. The label tool 1408 may indicate a currently-selected label using highlighting, color, font, outlining, emphasis, and/or other suitable indicators. The label tool 1408 may also display a status indicator 1412 for each label indicating a status such as whether or not the label has been applied. The status indicator 1412 may indicate whether a label has been applied to more than one branch, and in one such embodiment, the status indicator 1412 displays a single checkmark to indicate a label has been applied to a single branch and displays two checkmarks to indicate that the label has been applied to more than one branch. Additionally or in the alternative, the label tool 1408 may display a set of interactive objects 1414 (e.g., push buttons, checkboxes, radio buttons, text-based buttons, etc.) for setting attributes of the respective label. For example, a user may select an interactive object 1414 to indicate that the branch to which the label corresponds is missing and not present in the model and/or the anatomy.

The graphical user interface 400 is operable to receive user input and display a cursor 1416 responsive to the user input. When the cursor 1416 is positioned within a boundary of the label tool, the graphical user interface 400 may receive user input to select a label from the list 1410, activate or deactivate an interactive object 1414, and/or take other suitable action. When the cursor 1416 is positioned within the interactive window 1406, the graphical user interface 400 may receive user input to select a branch of the model, manipulate (e.g., rotate, pan, zoom, etc.) the image of model and/or image data of the surrounding anatomy, and/or take other suitable action. In an example, the graphical user interface 400 makes a selection in response to a first mouse button within the interactive window 1406 and rotates the perspective shown in the interactive window 90° in response to a second mouse button. When rotating the perspective, the graphical user interface 400 may also rotate a patient orientation indicator 1417 that represents the perspective of the model and surrounding anatomy being displayed in the interactive window 1406 relative to a patient.

When a label is selected and the cursor 1416 is positioned over a branch 1403 in the interactive window 1406, the graphical user interface 400 may indicate that the branch 1403 may be labeled by changing a representation of the cursor 1416, a representation of the branch 1403 or a plurality of branches extending from the selected branch in the interactive window 1406, and/or providing other suitable indication. Additionally or in the alternative, when a label is selected and the cursor 1416 is positioned in the interactive window 1406 but not over any branch 1403, the graphical user interface 400 may indicate that cursor is not over a branch by changing a representation of the cursor 1416 and/or providing other suitable indication.

Figure 14B:
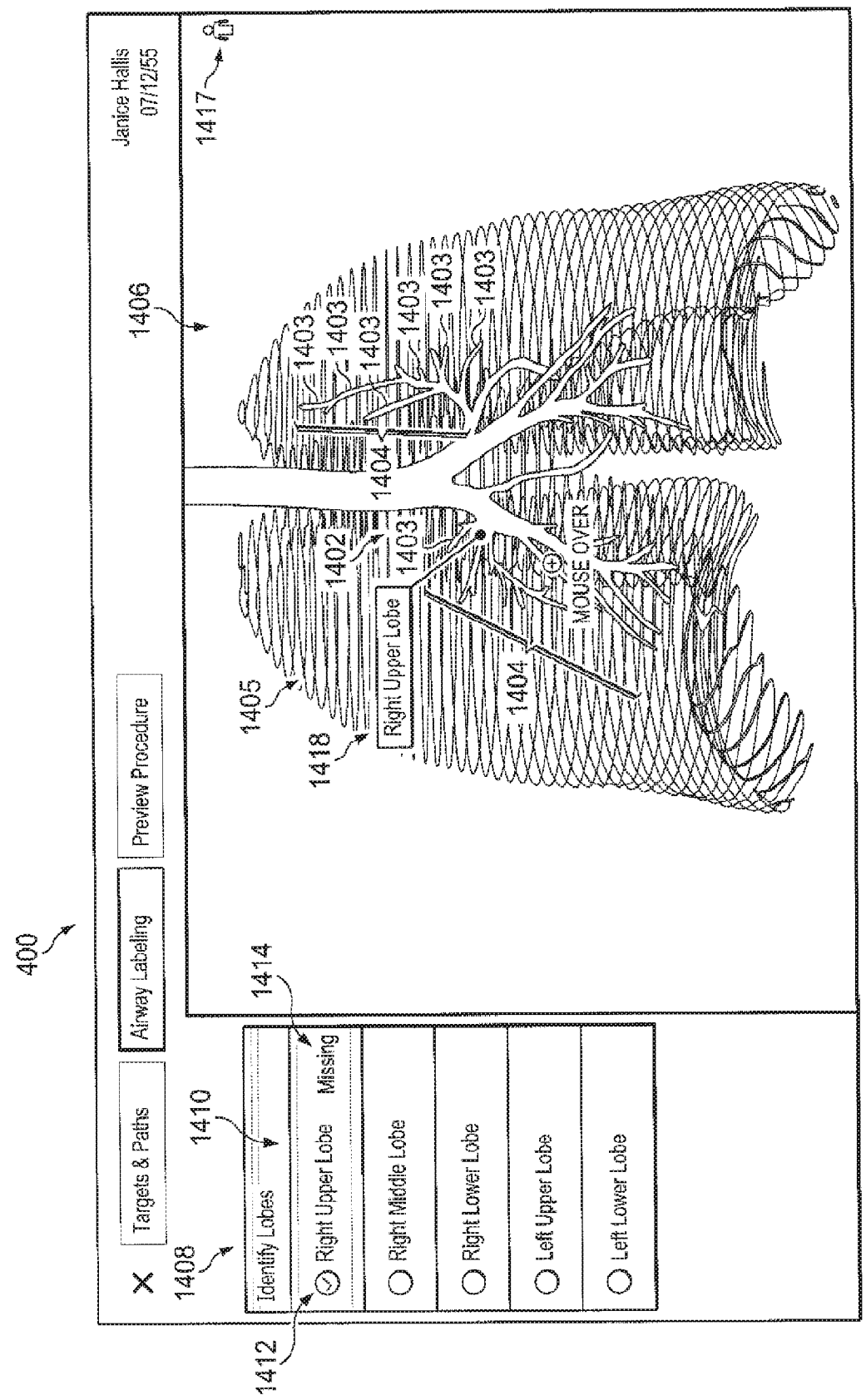

Examples of the graphical user interface 400 responding to user input are described with reference to FIGS. 14B-14F. FIG. 14B illustrates an example of applying a label to a branch 1403 of the anatomical passageways 1402 via the graphical user interface 400. In some embodiments, the label tool 1408 of the graphical user interface 400 automatically selects the first label to apply. The label tool 1408 may select the first label from those labels in the list 1410 that have not already been applied to at least one branch. The label tool 1408 may also provide an indication, such as those described above, that the first label has been selected. The user may override this automatic selection by selecting a different label via the label tool 1408. In the example illustrated in FIGS. 14A-14F, the labels are indicative of lung lobes. It should be understood that the labels can be indicative of other sections of the lungs including left or right lung, lung segments, and/or lung lobules.

The graphical user interface 400 may then receive a user selection of a branch 1403 via the interactive window 1406 and, in response, may assign the selected label to the selected branch 1403. Selecting a single branch 1403 may cause the graphical user interface 400 to identify other branches 1403 connected to the selected branch and assign the label to a plurality of branches 1403 as a whole. In some examples, a label indicator 1418 is displayed in the interactive window 1406, such as a flag, a marker, a text box, and/or other suitable indicator that represents the assigned label and the corresponding branch 1403 or plurality of branches 1403. The representation of the branch 1403 or plurality of branches 1403 in the interactive window 1406 may be colored, outlined, emphasized, deemphasized, or otherwise modified to indicate that the label has been assigned. The graphical user interface 400 may also update the respective status indicator 1412 in the label tool 1408 to indicate that the label has been assigned to at least one branch. In the illustrated example, a first branch 1403 is selected by the user and labeled as "Right Upper Lobe". The graphical user interface 400 highlights all branches connected to the first branch 1403 up to a main trunk (e.g. trachea of the lung) with a first color. All highlighted branches are effectively identified and labeled as belonging to the "Right Upper Lobe" section/lobe 1404 at this point.

Figure 14C:
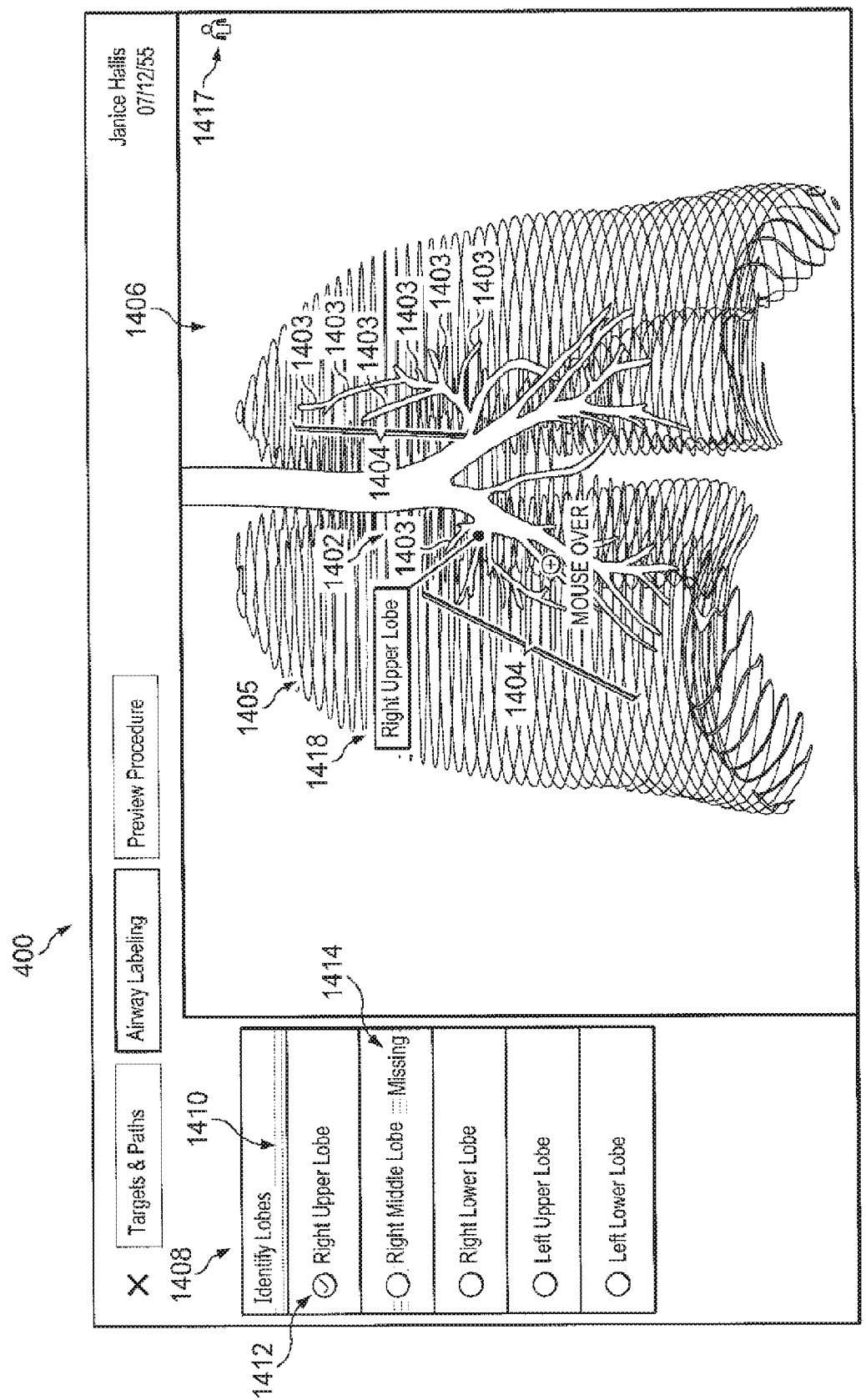

As depicted in FIG. 14C, when a label is applied to a branch 1403 or a plurality of branches 1403, the label tool 1408 may automatically select the next label to be applied in the list 1410. In some embodiments, the label tool 1408 selects the next label based on the arrangement of the branches in the anatomical passageways 1402. For example, a middle lobe label may be selected after assigning an upper lobe label because the upper lobe is proximate to the middle lobe in the anatomical passageways 1402. In some embodiments, the label tool 1408 selects from those labels in the list 1410 that have not yet been applied to any branch. For example, a lower lobe label may be selected after assigning an upper lobe label if the middle lobe label has already been used to label a branch. By automatically selecting the next label, in these embodiments and others, the user may continue selecting branches without moving the cursor out of the interactive window 1406.

Figure 14D:
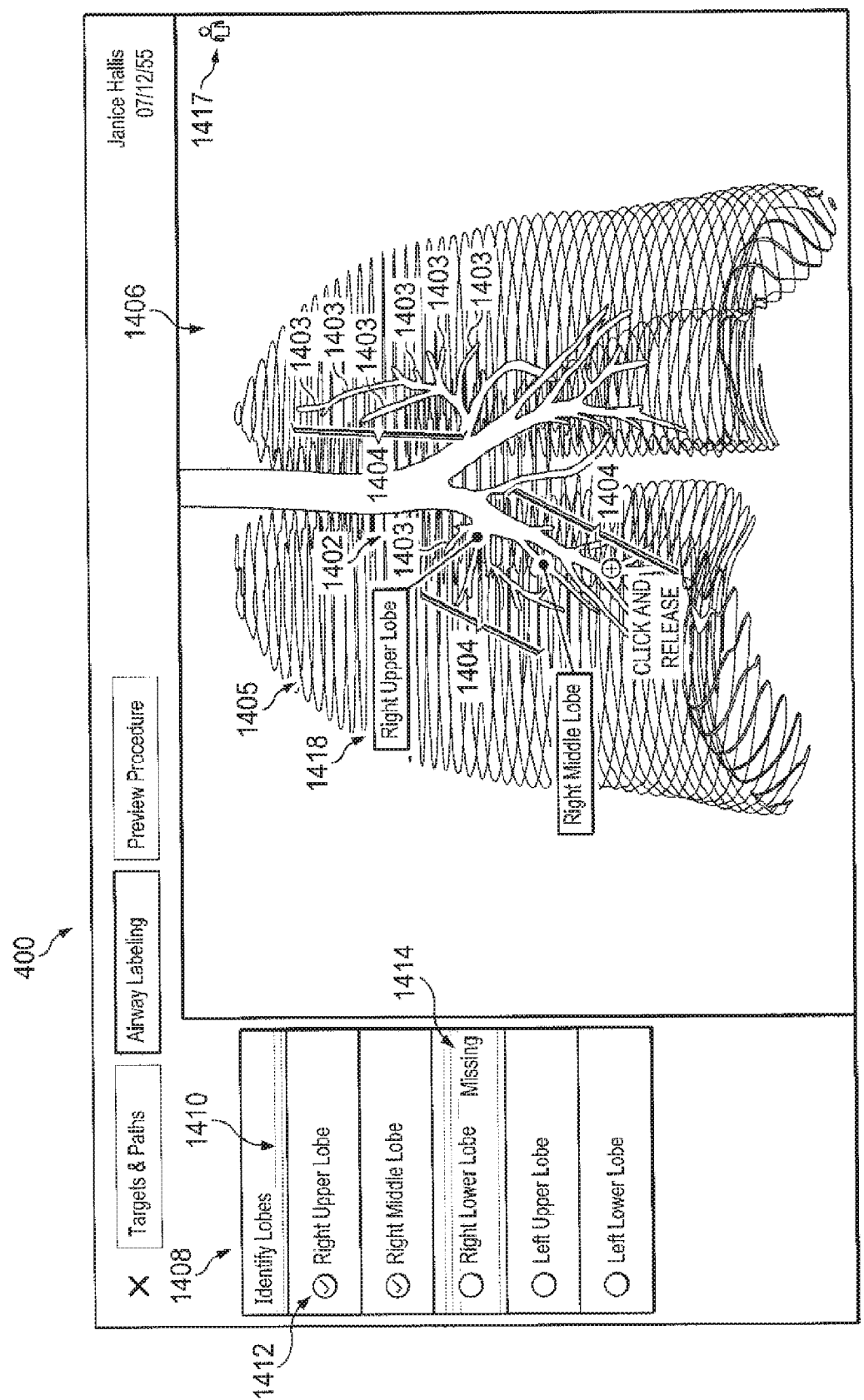

The process of selecting labels and branches may be repeated. As explained above in the context of FIG. 14B, in an example, a first branch 1403 is selected by the user and labeled as "Right Upper Lobe". As a result, all branches connected to the first branch 1403 up to a main trunk are also labeled as "Right Upper Lobe." In response, the graphical user interface 400 selects the next label, "Right Middle Lobe," as shown in FIG. 14C. Referring to FIG. 14D, a user selects a second branch 1403 to assign the label "Right Middle Lobe." The graphic user interface 400 assigns the label to and alters the color of all branches 1403 that are descendants of the second branch (e.g. child branches that stem from the second branch or are distal to and connected to the second branch) with a second color, identifying and labeling the descendant branches as belonging to a right middle lobe. In one example, when the second branch 1403 is selected, all descendant branches are highlighted with the second color and a portion of proximal/parent connected branches reflect a change in color up to a main trunk of the previously identified section/lobe 1404. In one embodiment, a plurality of branches 1403 may overlap, potentially belonging to two separate sections/lobes 1404. The overlapping branches can be highlighted in a separate specific color reflecting the overlap. This process is repeated for a "Right Lower Lobe" using a third color to identify and label branches distal to a third user selected branch within the right lower lobe. The process can again be repeated for a "Left Upper Lobe" and "Left Lower Lobe" until all the branches 1403 have been identified and labeled as belonging to a section/lobe 1404 as shown in FIG. 14E.

Figure 14E:
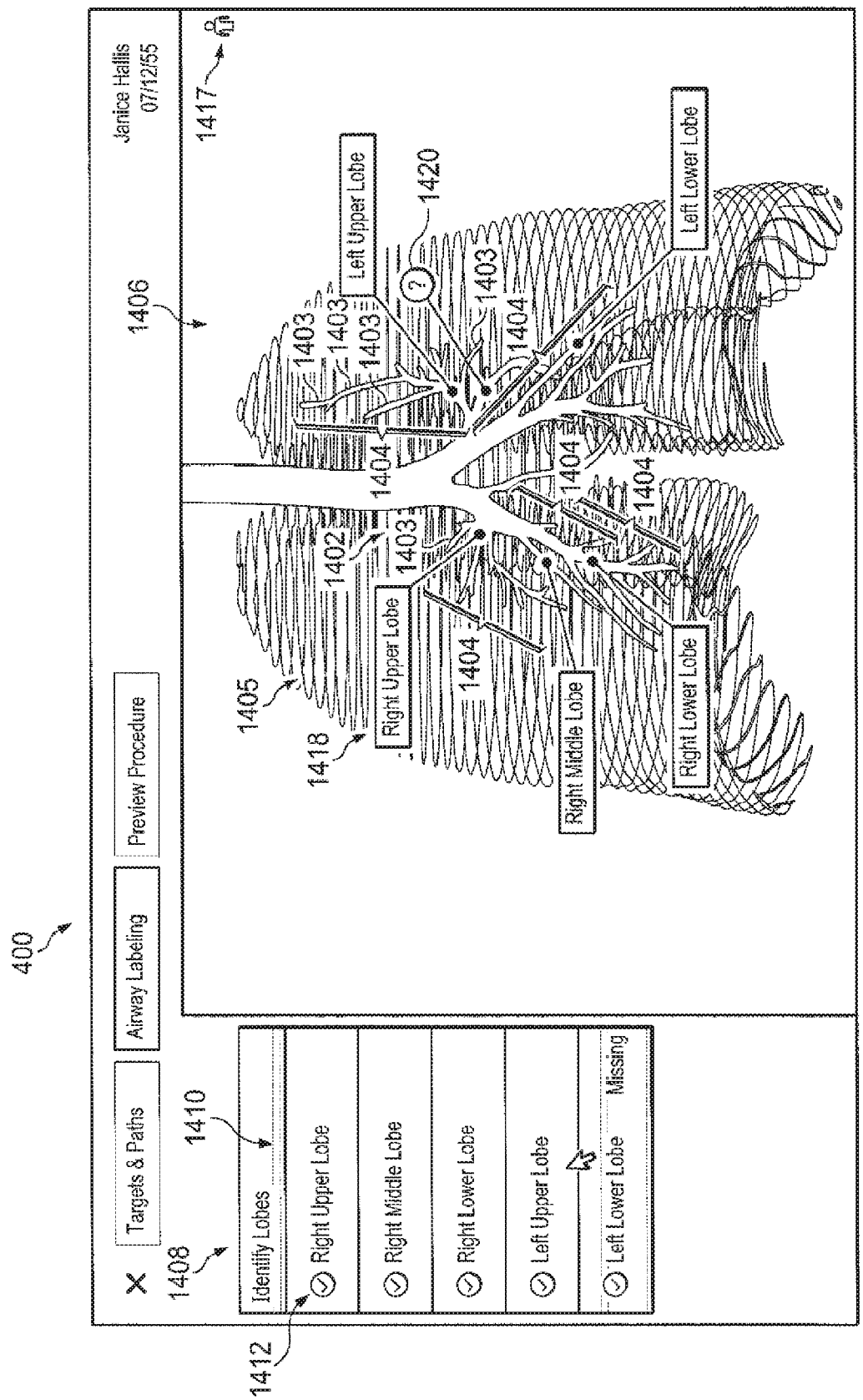
Figure 14F:
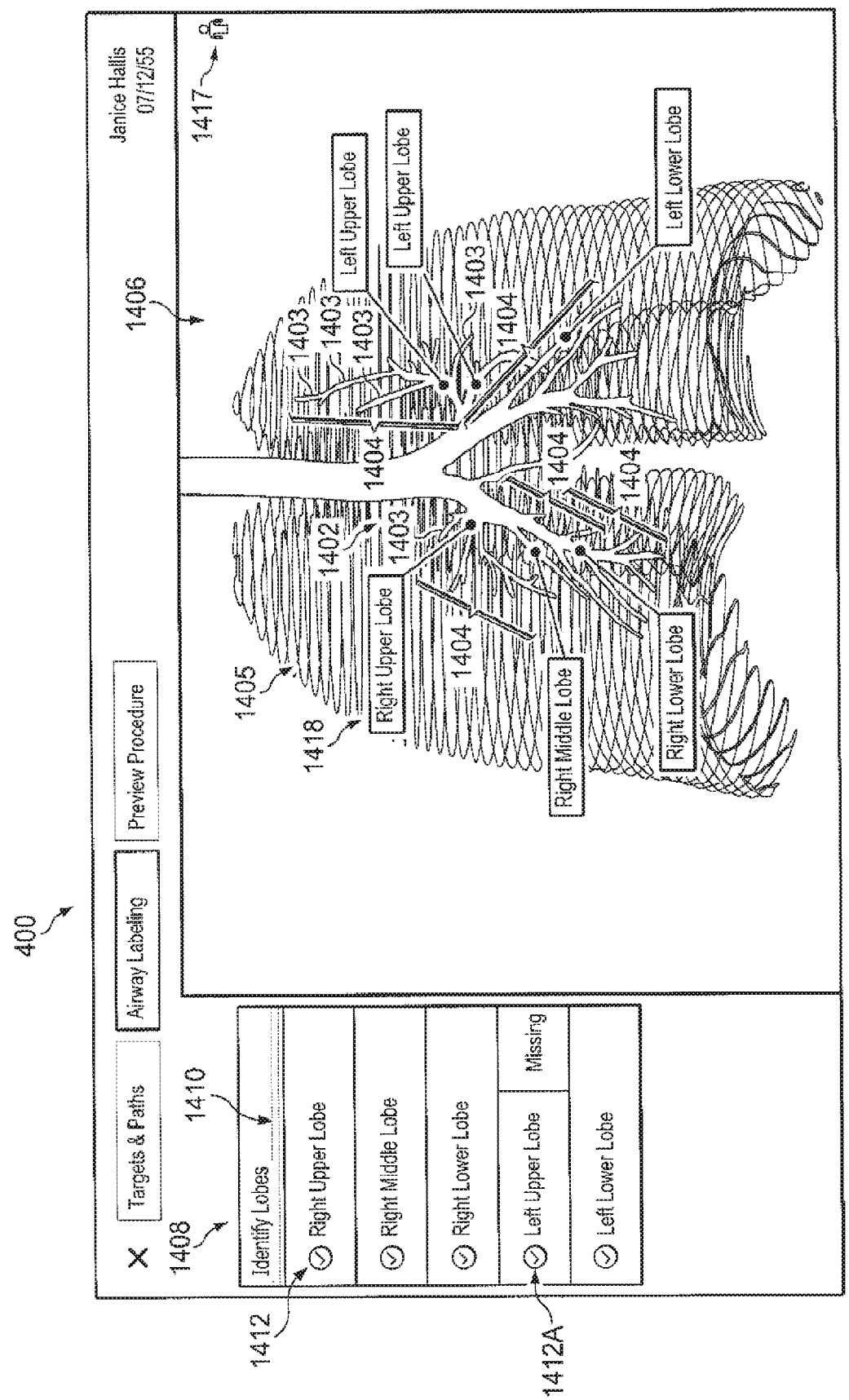

As depicted in FIG. 14E, to assist the user, in some embodiments, the graphical user interface 400 indicates in the interactive window 1406 those branches 1403 in the anatomical passageways 1402 that do not yet have a label. The graphical user interface 400 may use indicators 1420 such as flags, highlighting, outlines, color, line weight, and/or other suitable indicator to indicate unlabeled branches 1403. In one such example, the graphical user interface 400 displays a question mark flag with a connector extending to an unlabeled branch 1403. In some embodiments, the graphical user interface 400 indicates the remaining unlabeled branches for the user's reference when it detects that each label has been applied to at least one branch 1403. When the user selects a label and selects an unlabeled branch, the label may be applied to the branch 1403 and/or the section/lobe 1404 to which it belongs, and the indicator 1420 may be removed, as shown in FIG. 14F. In examples where unlabeled branch detection is performed when each label has been applied to at least one branch, applying a label to an unlabeled branch may result in the label being applied to more than one branch. As a result, the graphical user interface 400 may update the corresponding status indicator accordingly. In the examples of FIG. 14E, status indicator 1412A is updated to display a pair of checkmarks because the left upper lobe has been assigned to more than one section/lobe 1404. In a further example where unlabeled branch detection is performed when all labels have been applied to at least one branch, the graphical user interface 400 removes the unlabeled branch indicator 1420 when a label is deleted from a branch and it is no longer the case that all labels have been applied to at least one branch.

Figure 15A:
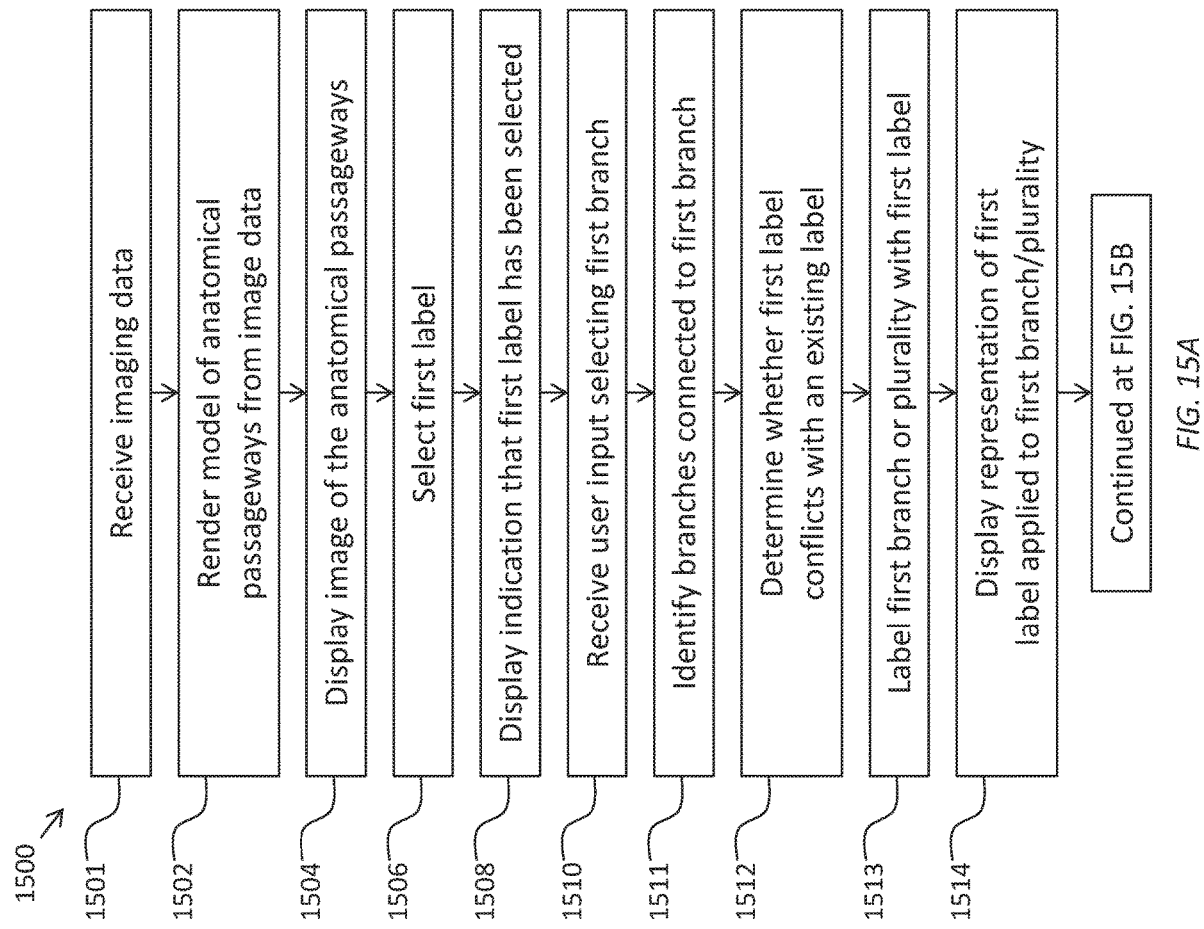
FIGS. 15A and 15B are simplified diagrams of a method of applying a label to a branched model of anatomical passageways according to some embodiments.
Figure 15B:
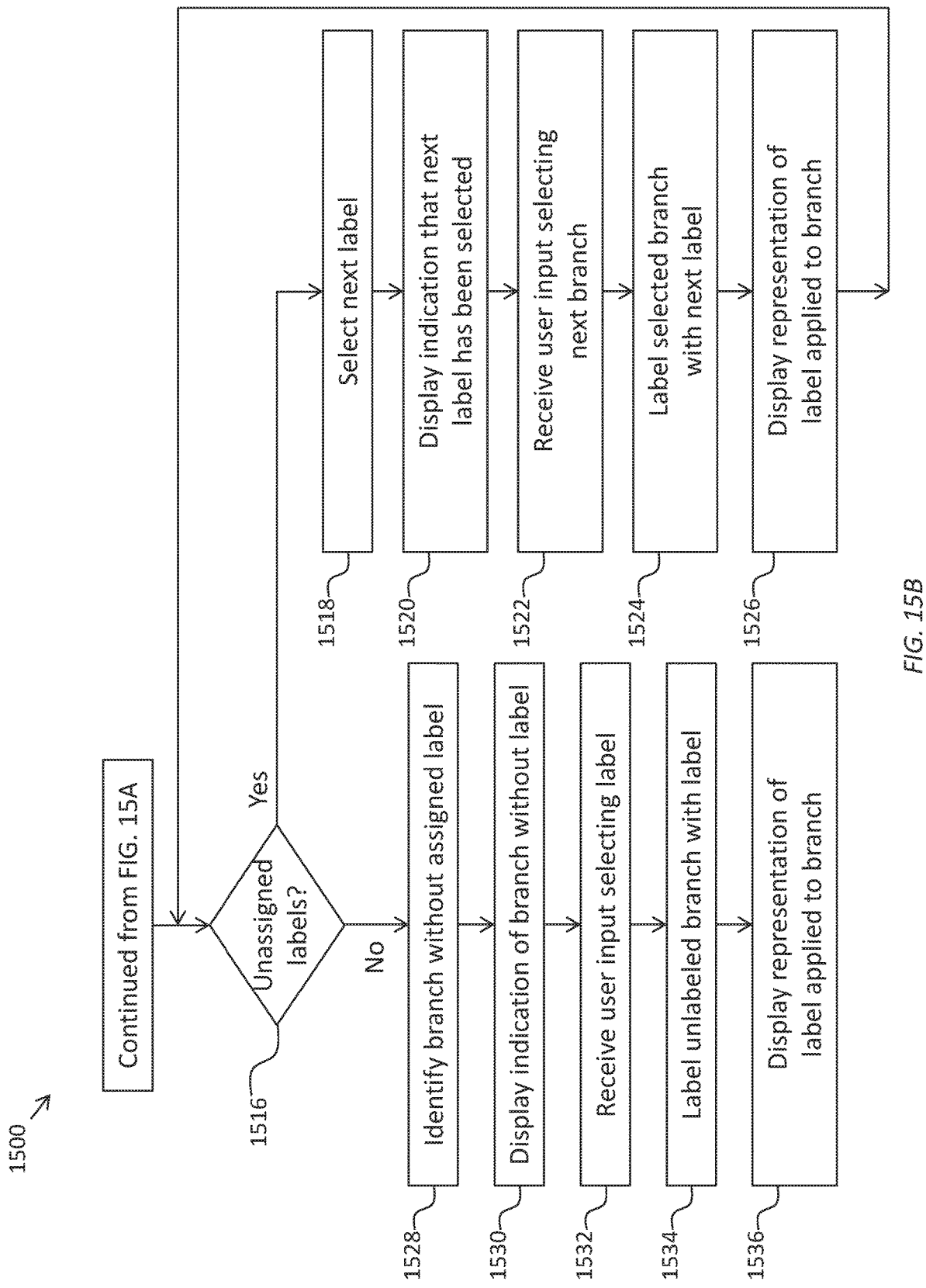

FIGS. 15A and 15B are simplified diagrams of a method 1500 for planning a medical procedure according to some embodiments. According to some embodiments consistent with FIGS. 14A-14F, method 1500 may be used to operate a graphical user interface, such as graphical user interface 400, in a branch labeling mode.

At process 1501 of FIG. 15A, imaging data such as CT data of a patient is received. At process 1502, a model of the patient anatomy is rendered from the image data. The model may include a set of anatomical passageways 1402 and/or other anatomical structures such as organs, blood vessels, tumors, lesions, etc. In particular, the anatomical passageways 1402 may include branches 1403 and/or other suitable structure.

At process 1504, an image of the model is displayed via the graphical user interface 400. According to some embodiments, the image of the model is displayed in an interactive window 1406 that includes representations of the anatomical passageways 1402 and of the surrounding anatomy (e.g., lung pleura 1405). These elements of the surrounding anatomy may be individually displayed or hidden to provide a frame of reference and improve clarity.

At process 1506, a first label is selected. The first label may be selected automatically and/or in response to a first user input received by a label tool 1408 of the graphical user interface. The user input may be provided via any suitable input mechanism including a mouse, keyboard, touch, stylus, trackball, joystick, speech commands, virtual reality interface, and/or the like. At process 1508, an indication that the first label has been selected is displayed by a label tool 1408 of the graphical user interface.

At process 1510, the graphical user interface 400 may receive a second user input selecting a first branch 1403 for the first label. The second user input may select the first branch 1403 via the interactive window 1406 in which the model is displayed. At process 1511, in some examples, the graphical user interface 400 identifies other branches 1403 connected to the first branch 1403 so that a plurality of branches 1403 may be labeled in a single process. In an example, this includes identifying those branches 1403 that are descendants of the first branch 1403 (e.g., child branches that stem distally from the first branch) and including the descendants in the section/lobe 1404. In this way, a label may propagate downstream from the selected branch. In an example, this includes identifying antecedent branches 1403 (e.g., parents, grandparents, etc. that stem proximally from the first branch) up to a main branch. The main branch can be the trachea of the lung in initial cases or a main branch of a previously identified section/lobe 1404. In this way, a label can propagate upstream so that a user may label a subtree without necessarily selecting the root of the subtree.

At process 1512, the graphical user interface 400 determines whether the label conflicts with a previously selected label. For example, a user may label a child branch with a right upper lobe label. If the child branch includes a parent branch that was previously labeled with a left upper lobe label, the algorithm can recognize that the conflict between the child and the parent branch. The graphical user interface 400 may reject applying the current label and illustrate the conflict by highlighting the current label, the currently-selected branch, the previous label, and/or the previously-selected branch. The user may then be presented the option to correct the previous label or the current label. Once any conflict is resolved, at process 1513, the first branch 1403 and any other branches 1403 identified in process 1511 are labeled with the first label.

At process 1514, the graphical user interface displays a representation of the first label applied to the first branch 1403 and/or its respective section/lobe 1404. In some such examples, the graphical user interface displays a flag, a marker, a text box, and/or other suitable indicator in the interactive window 1406 to represent the first label. In some examples, the representation of the first branch 1403 and/or its section/lobe 1404 in the interactive window 1406 is colored, outlined, emphasized, deemphasized, or otherwise modified to indicate that the label has been assigned.

Referring now to FIG. 15B, at process 1516, it is determined whether the label tool 1408 has additional unassigned labels. If so, at process 1518, a next label is selected. The next label may be selected automatically from a set of unassigned labels based on the arrangement of the branches 1403 in the anatomical passageways 1402 and/or other suitable criteria. The next label may also be selected in response to a first user input received by the label tool 1408 of the graphical user interface. In some such examples, the user selection overrides the automatic selection. At process 1520, an indication that the first label has been selected is displayed by the label tool 1408 of the graphical user interface. At process 1522, the graphical user interface may receive a user input selecting a branch of the anatomical passageways for the label. In response, at process 1524, the selected branch is labeled with the label. At process 1526, the graphical user interface displays a representation of the label applied to the branch. Processes 1518-1526 may be performed substantially similar to processes 1506-1514.

At process 1528, the graphical user interface may identify a branch 1403 of the anatomical passageways 1402 that does not have an assigned label. This may be performed when it is determined that each label has been assigned to at least one branch in process 1516. At process 1530, the graphical user interface displays an indicator that identifies the unassigned branch in the interactive window 1406 such as a flag, a highlight, an outline, a color, line weight, and/or other suitable indicator. At process 1532, a user input is received selecting a label. This may be performed substantially similar to process 1506 and/or 1518. At process 1534, the selected label is applied to the unassigned branch and its respective section/lobe, and at process 1536, the graphical user interface displays a representation of the label applied to the branch and/or section/lobe. Processes 1534-1536 may be performed substantially similar to processes 1511-1514. This may be repeated until each branch is assigned a label.

Figure 16:
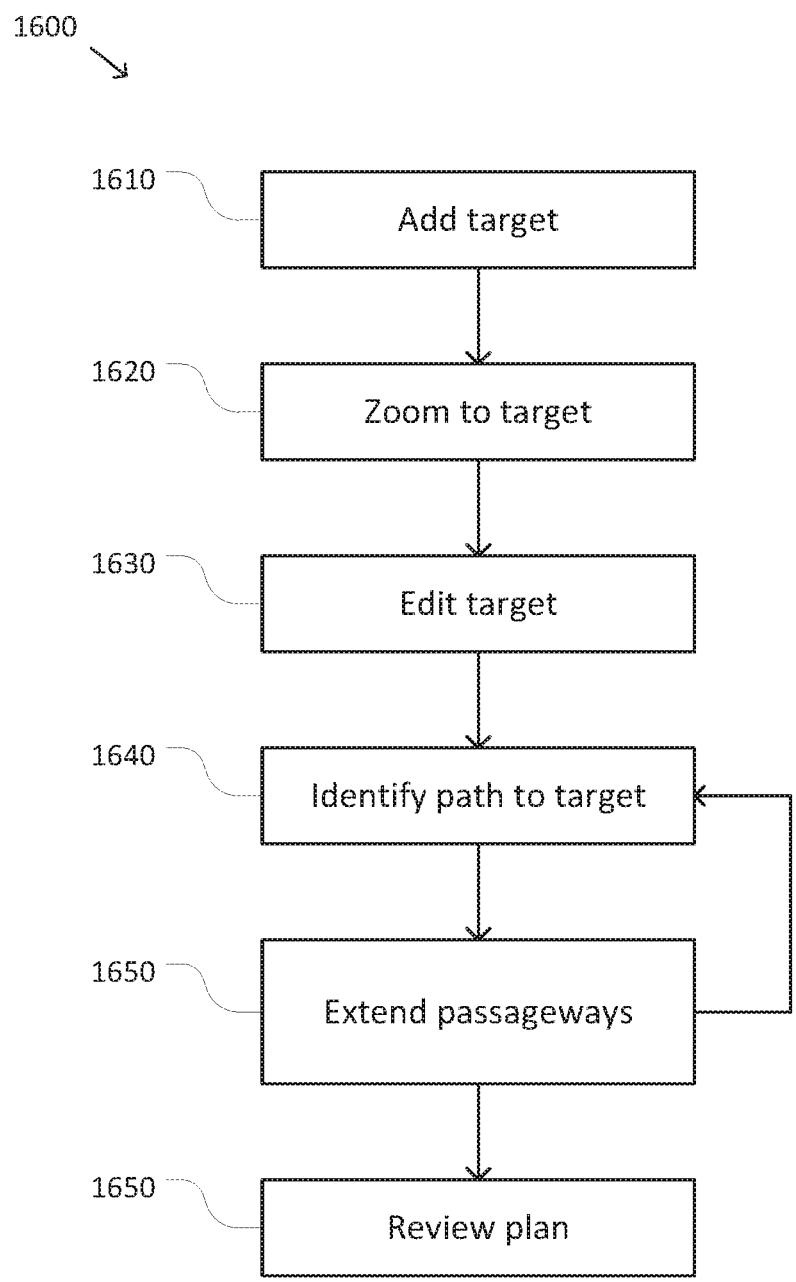
FIG. 16 is a simplified diagram of a method for planning a medical procedure according to some embodiments.

FIG. 16 is a simplified diagram of a method 1600 for planning a medical procedure according to some embodiments. FIGS. 17A-P are corresponding diagrams of graphical user interface 400 during the performance of method 1600 according to some embodiments. According to some embodiments consistent with FIGS. 1-15B, graphical user interface 400 may include features that generally correspond to similar features depicted in FIGS. 1-15B, such as interactive header 410, control frame 510, canvas frame 520, workspace 522, tool selector 524, interactive window 541, selection sidebar 542, image data 543, segmentation data 544, and/or the like. In some embodiments, graphical user interface 400 may include a mode selector 1712 (illustratively placed within interactive header 410) and/or a view selector 1714 (illustratively placed at the lower section of interactive window 541) for enabling and/or disabling various features of graphical user interface 400, including various features used during performance of method 1600.

At a process 1610, a target 1720 of the medical procedure is added via graphical user interface 400. Illustrative screenshots corresponding to process 1610 are depicted in FIGS. 17A and 17B. In some embodiments, target 1720 may generally correspond to target 550. As depicted in FIG. 17A, during addition of target 1720, a new target menu 1722 may be displayed in control frame 510. New target menu 1722 may display instructions for identifying, placing, adjusting, and/or otherwise configuring target 1720, controls for confirming and/or cancelling the addition of target 1720, and/or the like. When target 1720 has been added, target data 1724 may be displayed in control frame 510. As depicted in FIG. 17B, target data 1724 may include metrics associated with target 1720 (e.g., size metrics), controls (e.g., controls to delete, rename, and/or edit target 1720), and/or the like.

At a process 1620, an operator may optionally zoom to target 1720 (and/or other portions of image data 543) view graphical user interface 400. Illustrative screenshots corresponding to process 1610 are depicted in FIGS. 17C-17E. Graphical user interface 400 may provide one or more options for zooming to target 1720, including a non-synchronized zoom, a synchronized zoom, an auto-zoom, and/or the like. FIG. 17C depicts a zoom performed when a synchronized zoom feature of graphical user interface 400 is not enabled, and FIG. 17D depicts a zoom performed when the synchronized zoom feature is enabled. When the synchronized zoom feature is not enabled, zooming in and/or out of the image displayed in interactive window 541 is not accompanied by a matching zoom effect in the thumbnail images displayed in selection sidebar 542. Conversely, when the synchronized zoom feature is enabled, zooming in and/or out of the image displayed in interactive window 541 is accompanied by a matching zoom effect in the thumbnail images displayed in selection sidebar 542. FIG. 17E depicts a zoom performed using an auto-zoom feature of graphical user interface 400. Using the auto-zoom features causes target 1720 to be automatically centered and/or magnified in the image displayed in interactive window 541. The auto-zoom feature may or may not be accompanied by a matching zooming effect in the thumbnail images displayed in selection sidebar 542.

At a process 1630, an operator may optionally edit target 1720. An illustrative screenshot corresponding to process 1630 is depicted in FIG. 17F. As depicted in FIG. 17F, during editing of target 1720, an edit target menu 1726 may be displayed in control frame 510. Edit target menu 1726 may display instructions for editing target 1720, controls for confirming and/or cancelling the editing of target 1720, and/or the like. In some embodiments, the operator may modify attributes of target 1720 (e.g., the size, position, and/or the like) via interactive window 541 and/or via selection sidebar 542.

At a process 1640, a path 1730 to target 1720 is identified via graphical user interface 400. Illustrative screenshots corresponding to process 1640 are depicted in FIGS. 17G-17I. As depicted in FIG. 17G, path data 1732 corresponding to a selected path may be displayed in control frame 510. Path data 1732 may include metrics associated with path 1730 (e.g., distance between the endpoint of the path and target 1720, exit angle at the endpoint of the path, and/or the like), controls (e.g., controls to delete, rename, and/or edit path 1730), and/or the like. In some embodiments, one or more alerts associated with the path may be displayed via graphical user interface 400. For example, as depicted in FIG. 17G, an alert 1734 is displayed when the distance between the endpoint of the path and the nearest point of target 1720 exceeds a predetermined threshold. Similarly, as depicted in FIG. 17H, an alert 1736 is displayed when the exit angle at the endpoint of the path exceeds a predetermined threshold. In some embodiments, an endpoint slider 1738 may be displayed in control frame 510 to allow the operator to adjust the position of the endpoint along the path. In this regard, the operator may determine a position of the endpoint that is in compliance with the predetermined thresholds associated with the distance to target 1720 and/or the exit angle.

At a process 1650, one or more passageways are optionally extended via graphical user interface 400. For example, the one or more passageways may be extended when an acceptable path to target 1720 is not identified at process 1640. Illustrative screenshots corresponding to process 1650 are depicted in FIGS. 17J-17M. As depicted in FIG. 17J, an instruction panel 1740 may be displayed in control frame 510 to provide instructions for extending the one or more passageways. As depicted in FIG. 17K, the operator may draw a path extension 1742 via interactive window 541. Path extension 1742 may subsequently be rendered, as depicted in FIG. 17L. In some embodiments, path extension 1742 may be rendered in a different color, texture, pattern, and/or the like to distinguish path extension 1742 from portions of the path determined by segmentation. As depicted in FIG. 17M, the updated path to target 1720 may be in compliance with the predetermined thresholds associated with the distance to target 1720 and/or the exit angle, such that alerts 1734 and/or 1736 are no longer displayed with path data 1732.

At a process 1660, the plan for the medical procedure is reviewed via graphical user interface 400. An illustrative screenshot corresponding to process 1660 is depicted in FIG. 17N. The features depicted in FIG. 17N generally correspond to those of the preview mode of graphical user interface 400 as depicted in FIG. 6. Consistent with such embodiments, FIG. 17N depicts a virtual endoscopic view 620, a global anatomical model view 630, and a reduced anatomical model view 640. As depicted in FIG. 17N, global anatomical model view 630 includes controls, e.g., to allow the operator to pan, zoom, and/or rotate the model view and/or select among different types of images (e.g., CT images). Likewise, reduced anatomical model view 640 includes controls to start and/or pause playback of the plan for the medical procedure, to export the current plan, and/or the like. In some embodiments, an information panel 1750 may be displayed to provide information associated with the plan, such as metrics associated with the distance to target 1720.

Some examples of control units, such as control unit 130 may include non-transient, tangible, machine readable media that include executable code that when run by one or more processors (e.g., processor 140) may cause the one or more processors to perform the processes of methods 1000-1300 and/or method 1500 to render graphical user interface 400. Some common forms of machine readable media that may include the processes of methods 1000-1300, method 1500, and/or the instructions for rendering graphical user interface 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A planning workstation comprising:
   a display system; and
   a user input device;
   wherein the planning workstation is configured to:
   display image data via the display system;
   receive a first user input via the user input device;
   display via the display system a target of a medical procedure within the displayed image data identified based at least on the first user input;
   display an interactive image via the display system, the interactive image comprising the image data, a plurality of connected anatomical passageways, and the identified target, the target being disposed external to the plurality of connected anatomical passageways;
   receive a second user input via the user input device;
   display via the display system a defined trajectory identified based at least on the second user input, the defined trajectory extending between the target and an exit point along a connected passageway of the plurality of connected anatomical passageways nearest the target;
   receive a third user input via the user input device; and
   adjust the defined trajectory in the interactive image based at least on the third user input.

2. The planning workstation of claim 1, wherein the user input device includes a touchscreen of the display system.

3. The planning workstation of claim 1, wherein the planning workstation is configured to:
   determine a distance represented by the adjusted trajectory;
   determine whether the distance is greater than a predetermined threshold;
   receive a fourth user input via the user input device;
   identify an unconnected passageway that is closer to the target than the connected passageway based at least on the fourth user input; and
   connect the unconnected passageway to the plurality of connected anatomical passageways.

4. The planning workstation of claim 3, wherein the planning workstation is further configured to receive a fifth user input via the user input device, and rotate the interactive image to identify the unconnected passageway in the interactive image based at least on the fifth user input.

5. The planning workstation of claim 4, wherein the interactive image is rotated about one or more user-defined rotation points.

6. The planning workstation of claim 1, wherein the planning workstation is configured to determine an exit angle based on the defined trajectory, and wherein adjusting the defined trajectory comprises adjusting the exit angle by altering a position of the exit point along the connected passageway.

7. The planning workstation of claim 1, wherein the planning workstation is further configured to receive a fourth user input via the user input device, and display via the display system a hazard of the medical procedure within the displayed image data based on the fourth user input.

8. The planning workstation of claim 7, wherein the hazard corresponds to at least one of a vulnerable portion of a patient anatomy or an excessive bend in one or more of the plurality of connected anatomical passageways.

9. The planning workstation of claim 7, wherein the hazard is displayed using a hazard fence that includes at least one of a circular disk, a conic hazard fence, or a hemispherical hazard fence.

10. A method for planning a procedure with planning workstation comprising:
- displaying image data via a display system;
- receiving a first user input via a user input device;
- displaying via the display system a target of a medical procedure within the displayed image data identified based at least on the first user input;
- displaying an interactive image via the display system, the interactive image comprising the image data, a plurality of connected anatomical passageways, and the identified target, the target being disposed external to the plurality of connected anatomical passageways;
- receiving a second user input via the user input device;
- displaying via the display system a defined trajectory identified based at least on the second user input, the defined trajectory extending between the target and an exit point along a connected passageway of the plurality of connected anatomical passageways nearest the target;
- receiving a third user input via the user input device; and
- adjusting the defined trajectory in the interactive image based at least on the third user input.

11. The method of claim 10, wherein the user input device includes a touchscreen of the display system.

12. The method of claim 10, further comprising:
- determining a distance represented by the adjusted trajectory;
- determining whether the distance is greater than a predetermined threshold;
- receiving a fourth user input via the user input device;
- identifying an unconnected passageway that is closer to the target than the connected passageway based at least on the fourth user input; and
- connecting the unconnected passageway to the plurality of connected anatomical passageways.

13. The method of claim 12, further comprising:
- receiving a fifth user input via the user input device; and
- rotating the interactive image to identify the unconnected passageway in the interactive image based at least on the fifth user input.

14. The method of claim 13, wherein the interactive image is rotated about one or more user-defined rotation points.

15. The method of claim 10, further comprising:
- determining an exit angle based on the defined trajectory, wherein adjusting the defined trajectory comprises adjusting the exit angle by altering a position of the exit point along the connected passageway.

16. The method of claim 10, further comprising:
- receiving a fourth user input via the user input device; and
- displaying via the display system a hazard of the medical procedure within the displayed image data based on the fourth user input.

17. The method of claim 16, wherein the hazard corresponds to at least one of a vulnerable portion of a patient anatomy or an excessive bend in one or more of the plurality of connected anatomical passageways.

18. The method of claim 16, wherein the hazard is displayed using a hazard fence that includes at least one of a circular disk, a conic hazard fence, or a hemispherical hazard fence.

19. A non-transitory machine readable medium storing a plurality of instructions which, when executed by one or more processors, cause the one or more processors to perform:
- displaying image data via a display system;
- receiving a first user input via a user input device;
- displaying via the display system a target of a medical procedure within the displayed image data identified based at least on the first user input;
- displaying an interactive image via the display system, the interactive image comprising the image data, a plurality of connected anatomical passageways, and the identified target, the target being disposed external to the plurality of connected anatomical passageways;
- receiving a second user input via the user input device;
- displaying via the display system a defined trajectory identified based at least on the second user input, the defined trajectory extending between the target and an exit point along a connected passageway of the plurality of connected anatomical passageways nearest the target;
- receiving a third user input via the user input device; and
- adjusting the defined trajectory in the interactive image based at least on the third user input.

20. The non-transitory machine readable medium of claim 19, wherein the user input device includes a touchscreen of the display system.

* * * * *

UNITED STATES PATENT AND TRADEMARK OFFICE
CERTIFICATE OF CORRECTION

PATENT NO. : 11,571,262 B2
APPLICATION NO. : 16/496034
DATED : February 7, 2023
INVENTOR(S) : Bai Wang et al.

It is certified that error appears in the above-identified patent and that said Letters Patent is hereby corrected as shown below:

In the Specification

Column 13, Line 10, change "MM" to -- MRI --

Column 34, Line 55, change "MM" to -- MRI --

Column 40, Line 53, change "17l" to -- 17I --

Signed and Sealed this
Twenty-eighth Day of March, 2023

Katherine Kelly Vidal
*Director of the United States Patent and Trademark Office*